US012692538B2

(12) United States Patent
Ippodrino et al.

(10) Patent No.: US 12,692,538 B2
(45) Date of Patent: Jul. 28, 2026

(54) MOLECULAR FINGERPRINTING METHODS TO DETECT AND GENOTYPE DNA TARGETS THROUGH POLYMERASE CHAIN REACTION

(71) Applicant: ULISSE BIOMED S.P.A., Udine (IT)

(72) Inventors: Rudy Ippodrino, Trieste (IT); Bruna Marini, Trieste (IT); Alice Avian, Trieste (IT); Marco Mocenigo, Trieste (IT); Nicola Foschi, Forli (IT); Elisabetta Mauro, San Michele Al Tagliamento (IT); Michele Montrone, Turin (IT)

(73) Assignee: ULISSE BIOMED S.P.A., Udine (IT)

( * ) Notice: Subject to any disclaimer, the term of this patent is extended or adjusted under 35 U.S.C. 154(b) by 907 days.

(21) Appl. No.: 16/625,660

(22) PCT Filed: Jun. 20, 2017

(86) PCT No.: PCT/IT2017/000125
§ 371 (c)(1),
(2) Date: Dec. 20, 2019

(87) PCT Pub. No.: WO2018/235109
PCT Pub. Date: Dec. 27, 2018

(65) Prior Publication Data
US 2020/0123598 A1 Apr. 23, 2020

(51) Int. Cl.
*C12Q 1/6848* (2018.01)
*C12Q 1/6853* (2018.01)
*C12Q 1/6858* (2018.01)
*C12Q 1/70* (2006.01)

(52) U.S. Cl.
CPC ......... *C12Q 1/6848* (2013.01); *C12Q 1/6853* (2013.01); *C12Q 1/6858* (2013.01); *C12Q 1/708* (2013.01); *C12Q 2525/119* (2013.01); *C12Q 2525/301* (2013.01); *C12Q 2527/107* (2013.01); *C12Q 2537/143* (2013.01); *C12Q 2537/163* (2013.01); *C12Q 2563/173* (2013.01); *C12Q 2565/10* (2013.01); *G01N 2800/50* (2013.01)

(58) Field of Classification Search
CPC .... C12Q 1/6848; C12Q 1/6853; C12Q 1/708; C12Q 2525/119; C12Q 2525/301; C12Q 2527/107; C12Q 2537/143; C12Q 2537/163; C12Q 2563/173; C12Q 2565/10; C12Q 1/6858
See application file for complete search history.

(56) References Cited

U.S. PATENT DOCUMENTS 6,297,365 B1 10/2001 Adams et al.
7,745,473 B2 * 6/2010 Sugiyama ............... A61P 35/00
514/397

8,980,562 B1 3/2015 Manna
2008/0112973 A1 * 5/2008 Lowy ...................... A61P 31/12
435/235.1
2015/0072351 A1 * 3/2015 Park ...................... C12Q 1/686
435/6.12
2015/0079637 A1 3/2015 Makarov et al.

FOREIGN PATENT DOCUMENTS

WO WO-2010/075413 A1 7/2010

OTHER PUBLICATIONS

Gundry et al. Nucleic Acids Research 2008; 36: 3401-3408. (Year: 2008).*
Chagné. Methods in Molecular Biology 2015; 1245: 151-159. (Year: 2015).*
Kaltenboeck et al. Advances in Clinical Chemistry 2005; 40: 219-259. (Year: 2005).*
Wittwer et al. BioTechniques 1997; 22: 130-138 (Year: 1997).*
Jaakola et al. Food Chemistry 2010; 123: 494-500. (Year: 2010).*
Lieveld et al., "A high resolution melting (HRM) technology-based assay for cost-efficient clinical detection and genotyping of herpes simplex virus (HSV)-1 and HSV-2," Journal of Virological Methods, vol. 248, pp. 181-186, 2017.
Gelaye et al., "A novel HRM assay for the simultaneous detection and differentiation of eight poxviuses of medical and veterinary importance," Scientific Reports, vol. 7, p. 42892, 2017.
Tsakogiannis et al., "Duplex Real-time PCT assay and SYBR green I melting curve analysis for molecular identification of HPV genotypes 16, 18, 31, 35, 51 and 66," vol. 29, No. 1, pp. 13-18, 2015.
International Search Report and Written Report for PCT/IT2017/000125, mailed Mar. 14, 2018.

* cited by examiner

*Primary Examiner* — Angela M. Bertagna
(74) *Attorney, Agent, or Firm* — MARSHALL, GERSTEIN & BORUN LLP

(57) ABSTRACT

A molecular fingerprinting method is disclosed to detect and genotype pathogen DNA targets in a sample through polymerase chain reaction (PCR) and High Resolution Melting (HRM) analysis. The PCR mixture used comprises two or more pairs of amplification primers designed to generate amplicons with different melting temperatures from each other to discriminate, in the HRM analysis, each amplicon by observing its specific melting temperature. The method further comprises monitoring, during the HRM analysis, the change in the signal emission resulting from the temperature-induced denaturation of the double-stranded amplicons into two single-stranded DNAs, due to the release of an intercalating molecule or compound. Discrimination and genotyping of different strains of the same pathogen, different pathogens belonging to separated genus and genetic variations in the sample can be determined through a reader analysing the signal variation; the result of which are obtained through a graphic interface connected to the reader.

18 Claims, 3 Drawing Sheets
Specification includes a Sequence Listing.

MOLECULAR FINGERPRINTING METHODS TO DETECT AND GENOTYPE DNA TARGETS THROUGH POLYMERASE CHAIN REACTION

FIELD OF THE INVENTION

Embodiments of the present disclosure relate to primers, oligonucleotides, chemical components and methods for a multiplex Polymerase Chain Reaction (PCR) analysis able to discriminate and genotype different strains of the same pathogen, different pathogens belonging to separated genus and genetic variations in a single reaction. In particular, embodiments of the present disclosure relate to primers, oligonucleotides, methods and conditions to detect and characterize different strains of pathogens responsible for sexually transmitted diseases, such as, but not limited to, high-risk human papilloma virus (HPV), through PCR using High Resolution Melting (HRM) technology in one multiplex assay.

BACKGROUND OF THE INVENTION

Polymerase Chain Reaction (PCR) is a robust technique used for diagnostic applications worldwide. PCR consists of a primer extension reaction that amplifies specific nucleic acids in vitro. The reaction exploits a thermostable DNA polymerase and it is based on several cycles including different temperature steps, that allow DNA denaturation, primer annealing, and polymerase-mediated elongation of the target DNA.

PCR can be combined with fluorescent dyes able to intercalate with double stranded DNA, or fluorescently-labelled DNA probes; in this way, the signal derived from newly synthesized amplicons can be quantitatively acquired in real-time through fluorescence acquisition.

High Resolution Melting (HRM) is an additional post-PCR analysis step that further characterizes the amplicons by studying thermal denaturation of double-stranded DNA. This occurs through the analysis of amplicon disassociation (melting) behaviour in a ramp of temperatures usually ranging from 65° C. to 95° C., with a fluorescence acquisition rating of 0.1° C./sec or less. This method allows to discriminate sequence variations and features among different amplicon, and even single nucleotide polymorphisms (SNPs) can be observed.

HRM is used in diagnostics, for example in the context of genetic tests able to identify SNPs in polymorphic alleles and it has been proposed for a variety of applications including pathogen detection.

Nowadays HRM analysis requires highly pure extracted DNA: this restricts its application mostly to high-income settings where DNA extraction is automatized.

Moreover, to achieve high specificity, HRM is performed in PCR reactions requiring target-dedicated primers and probe sets, that are not usually a quite affordable reagent. Nevertheless, HRM has an enormous unexplored potential for useful applications also in low-income settings, such as the characterization of human pathogens.

It is well known that Human Papillomavirus (HPV) is the main cause of cervical cancer. This tumour is the second most frequent tumour in women with more than 500,000 cases worldwide[1] and it is mostly determined by persistent infection of high risk HPV (HR-HPV) genotypes; approximately 20 cancer-associated HR-HPV have been described so far, being HPV16 and HPV18 the most frequent (70% of all invasive cervical cancer)[2,3]. Effective cervical cancer screening programs have reduced the incidence and the mortality of this tumor[4]; initially screening was performed with the Papanicolau test (Pap test), a cytological test able to identify precancerous cells after collection of cervical specimen by endocervical brush, and after plating and staining the specimen on a microscopic slide. This technique shows a very high positive predictive value but it has poor average sensibility[5] and low negative predictive value.

Current studies indicate that HPV DNA testing is more efficient for the prevention of invasive cervical cancer than the Pap test screening alone, given the higher negative predictive value of the HPV DNA test[6-8]. In addition, given the variability of positive predictive values for cancer development among different HR-HPV genotypes, HPV genotyping is useful for the triage of HPV-positive patients, both in cervical cancer and in other HPV-related cancers (such as ano-genital and oropharyngeal tumours)[9-13]. It might as well discriminate the transient infections from the persistent ones, being the latter the true risk factor for cancer transformation. Finally, genotyping test might represent an important tool for vaccine monitoring and herd immunity in population study, to assess the variation of the prevalence of each genotype in vaccinated and not-vaccinated population[14].

Nowadays the most diffused tests can be classified into two groups[15]:

1. Signal amplification assays, such as the Digene® HPV test based on Hybrid Capture® 2 (HC2, Qiagen) technologies, and the Cervista® HPVHR assay. The HC2 is based on a non-radioactive signal-amplification method based on the hybridization of 13 labelled HR-HPV-specific RNA probes to the target HPV DNA; the DNA-RNA hybrid is recognized by a specific antibody conjugated to alkaline phosphatase and adsorbed to the bottom of microwells. Enzyme activity, measured through a chemiluminescent signal, is directly proportional to the amount of target DNA. Cervista® HPV-HR assay exploits a fluorescence-resonance energy transfer (FRET)-based technology and there are two probes for each HPV type; it can detect 14 HR-HPV.

These techniques are quantitative and have a low false-positive rate but they do not provide any HPV genotyping information and they require dedicated instruments.

2. Nucleic Acid Amplification Assays, based on Real Time PCR method; among these tests, COBAS 4800 HPV test (by Roche) is the most diffused and exploits several primers and probe pairs in a fully automated system, and provide genotyping information for HPV16 and HPV18. This test, as the Qiagen, is considered the golden standard, and it has a very high sensitivity.

Other PCR-based tests include the Papillocheck® (Greiner Bio-One) capable to detect and genotype 24 HPV with 28 probes spotted on a DNA chip; after PCR the hybridization is performed on a microarray chip that is automatically scanned and analysed.

The Linear Array HPV Genotyping (Roche) is a PCR-based assay coupled with reverse line blot hybridization, able to discriminate 37 HPV; however, the test is time-consuming and it can provide equivocal results also due to easy cross-hybridization. Cepheid HPV is the only test present on the market able to use directly PreservCyt samples in a ready-to-use cartridge that then undergo a dedicated PCR run in modular machines.

All these tests require dedicated instruments and are not affordable enough for a widespread diffusion especially in developing countries.

PCR multiplexing is often a tricky analysis due to the use of several primer set that lead to fluorescence aspecific amplification signals (such as ones derived from primer dimers formation). This can be limited thanks to fluorescently-labelled probes (e.g. Taqman probes, Life Technologies), that ensures a higher specificity compared to intercalating dyes that does not make distinction between amplicons. However, fluorescently-labelled probes dramatically increase the cost of the assay, affect test robustness and more than one fluorescence channel is required; this means that the tests can be executed only by dedicated instruments with peculiar specificities.

There is therefore a need to improve molecular fingerprinting methods to detect DNA targets through polymerase chain reaction (PCR), which overcome at least one of the drawbacks in the art.

One aim of the present disclosure is to provide molecular fingerprinting methods to detect DNA targets or genotypes through PCR.

In particular, one aim of the present disclosure is to discriminate pathogens, in particular viral Human Papillomavirus genotypes through a specific HRM analysis in a single reaction.

One further aim of the present disclosure is to increase the amplification of specific PCR amplicons only, reducing aspecific signal emission, e.g. fluorescent, background.

One further aim of the present disclosure is to avoid primer dimers.

Still one further aim of the present disclosure is to provide primers, oligonucleotides, chemical components and methods for a multiplex PCR that overcome aspecific fluorescence signal problems as above discussed.

Yet one further aim of the present disclosure is to set each real-time PCR machine for a correct and precise melting analysis required to genotype the pathogen.

SUMMARY OF THE INVENTION

According to embodiments, a molecular fingerprinting method to detect and genotype DNA targets in a sample through Polymerase Chain Reaction (PCR) is provided. The method of the present disclosure is able to discriminate and genotype different strains of the same pathogen, different pathogens belonging to separated genus and genetic variations in a single reaction. In one embodiment, the method includes:

providing a PCR reaction mixture comprising an amplification buffer comprising an intercalating molecule or compound incorporated into the double-stranded amplicon and emitting a detectable signal;
   performing PCR amplification using said PCR reaction mixture and said sample;
   performing, at the end of the PCR amplification, a High Resolution Melting (HRM) analysis on the PCR reaction mixture and the sample previously subjected to PCR amplification;
wherein the PCR reaction mixture comprises two or more pairs of amplification primers for amplifying, in a multiplex approach, two or more target nucleic acids,
wherein said amplification primers are designed in order to generate amplicons with a different melting temperature each other in order to discriminate, in the HRM analysis, each amplicon by observing the specific melting temperature of each amplicon, wherein the method further comprises monitoring, during the HRM analysis, the change in the signal emission resulting from the temperature-induced denaturation of the double-stranded amplicons into two single-stranded DNA, due to the release of the intercalating molecule or compound,
wherein the method further comprises determining discrimination and genotyping of different strains of the same pathogen, different pathogens belonging to separated genus and genetic variations in the sample, through a reader analysing the signal variation and obtaining the result of the analysis through a graphic interface connected to said reader.

According to further embodiments, a diagnostic kit to detect and genotype DNA targets is provided, comprising a PCR reaction mixture that can be used to perform PCR amplification and a subsequent a HRM analysis on the PCR reaction mixture previously subjected to real-time PCR. In one embodiment, the PCR reaction mixture comprises two or more pairs of amplification primers for amplifying, in a multiplex approach, two or more target nucleic acids,
wherein said primers are designed in order to generate amplicons with a different melting temperature each other in order to discriminate, in the HRM analysis, each amplicon by observing the specific melting temperature of each amplicon.

According to still further embodiments, amplification primers are provided for performing a molecular fingerprinting method to detect and genotype DNA targets through PCR, wherein the method is able to discriminate and genotype different strains of the same pathogen, different pathogens belonging to separated genus and genetic variations in a single reaction. In one embodiment, the amplification primers are provided for amplifying in a multiplex approach two or more target nucleic acids in a PCR amplification, wherein said primers are designed in order to generate amplicons with a different melting temperature each other in order to discriminate, in a HRM analysis following the PCR amplification, each amplicon by observing the specific melting temperature of each amplicon.

According to yet further embodiments, an apparatus to perform a molecular fingerprinting method for detection and genotyping of DNA targets in a sample through PCR is provided. The method is able to discriminate and genotype different strains of the same pathogen, different pathogens belonging to separated genus and genetic variations in a single reaction. In one embodiment, the apparatus includes:

a PCR reaction mixture comprising an amplification buffer comprising an intercalating molecule or compound incorporated into the double-stranded amplicon and emitting a detectable signal;
   a PCR amplification device configured for using said PCR reaction mixture and said sample;
   a device for performing a HRM analysis on the PCR reaction mixture and the sample previously subjected to PCR amplification;
wherein the PCR reaction mixture comprises two or more pairs of amplification primers for amplifying in a multiplex approach two or more target nucleic acids,
wherein said primers are designed in order to generate amplicons with a different melting temperature each other in order to discriminate, in the HRM analysis, each amplicon by observing the specific melting temperature of each amplicon;
   monitoring means for monitoring, during the HRM analysis, the change in the signal emission resulting from the temperature-induced denaturation of the double-stranded amplicons into two single-stranded DNA, due to the release of the intercalating molecule or compound, a reader analysing the signal variation for determining discrimination and genotyping of different strains of the same pathogen, different pathogens belonging to separated genus and genetic variations in the sample, so that the result of the analysis can be obtained through a graphic interface connected to said reader.

According to embodiments, combinable with all embodiments described herein, the DNA target that can be detected and genotyped is a pathogen DNA target.

Advantageously, the proposed technique exploits common DNA intercalating molecules or compounds, such as for instance intercalating dyes, that are much more affordable than fluorescently-labelled probes.

Moreover, according to the present disclosure, the post-PCR HRM analysis does not require a dedicated instrument but it can also be performed in any thermocycler with a HRM resolution of at least 0.1° C./sec or less. In this context primer design is crucial and the primers designed according to the present disclosure are found to be fully successful in ensuring the highest specificity for each single target, given the multiplex assay format.

In advantageous embodiments, the melting fingerprinting technology according to the present disclosure has been applied to successfully improve the detection of HPV DNA, the main cause of cervical cancer.

Advantageously, embodiments described herein may use specific buffer and condition, specific DNA primers and innovative hybrid primers.

Embodiments described herein allow to discriminate, for example, viral HPV genotypes through a specific HRM analysis.

Advantageously, embodiments described herein allow to detect up to 37 HPV types, including for instance 6, 11, 16, 18, 26, 31, 33, 35, 39, 40, 42, 45, 51, 52, 53, 54, 55, 56, 58, 59, 61, 62, 64, 66, 67, 68, 69, 70, 71, 72, 73 (MM9), 81, 82 (MM4), 83 (MM7), 84 (MM8), IS39, CP6108. The viral genome amplification reaction can be coupled to the amplification of a DNA loading control target (human beta-globin gene for example).

Other pathogens that can be detect according to the present disclosure include for instance other pathogens than HPV responsible for sexually transmitted diseases, such as the *bacterium Treponema pallidum* subspecies pallidum, responsible for the syphilis infection, the *bacterium Neisseria gonorrhoeae*, responsible for the gonorrhoea infection, the *bacterium Chlamydia Trachomatis*, responsible for the chlamydia infection, and the HIV virus.

Embodiments described herein also provide a melting calibrator that is required to set each real-time PCR machine for a correct and precise melting analysis required to genotype the pathogens.

Embodiments described herein according to the present disclosure fully solve the above-mentioned issues of the tests and methods of the prior art, and further provide at least the following advantages:

novel sample type can be used: embodiments of the present disclosure can work using DNA extracted directly from different sample types as the vaginal and cervical mucus (i.e. a crude sample), a biological sample that the women can easily self-collect with no invasiveness and no pain;

affordability: embodiments of the present disclosure are much affordable compared to the afore-mentioned tests and methods of the prior art, because they do not use dozens of expensive labelled-probes but a unique intercalating molecule or compound, e.g. an intercalating dye can be provided; moreover the genotyping does not require incubation and reverse blot steps but it can be performed in a single short PCR reaction (for instance in less than 50 minutes);

open-accessibility: embodiments of the present disclosure can be executed by any real-time PCR machine and do not require a dedicated and specific instrument;

single-channel: result of embodiments of the present disclosure can be provided through the analysis of a single signal, e.g. fluorescence, channel, in contrast to the afore-mentioned tests and methods of the prior art, where more than one channel is used. The selected channel can be chosen among those embedded in any real-time PCR machine and this makes embodiments of the present disclosure suitable for any real-time PCR machines.

These and other features, aspects and advantages of the present disclosure will become better understood with reference to the following description, the drawings and appended claims. The drawings, which are incorporated in and constitute a part of this specification, are used to illustrate embodiments of the present subject matter and, together with the description, serve to explain the principles of the disclosure.

The various aspects and features described in the present disclosure can be applied, individually, wherever possible. These individual aspects, for instance the aspects and features described in the attached dependent claims, can be made subject of divisional patent applications.

It is noted that anything found to be already known during the patenting process is understood not to be claimed and to be the subject of a disclaimer.

BRIEF DESCRIPTION OF THE DRAWINGS

So that the manner in which the above recited features of the present invention can be understood in detail, a more particular description of the invention, briefly summarized above, may be had by reference to embodiments. The accompanying drawings relate to embodiments of the disclosure and are described in the following.

DETAILED DESCRIPTION OF THE EMBODIMENTS

Figure 1:
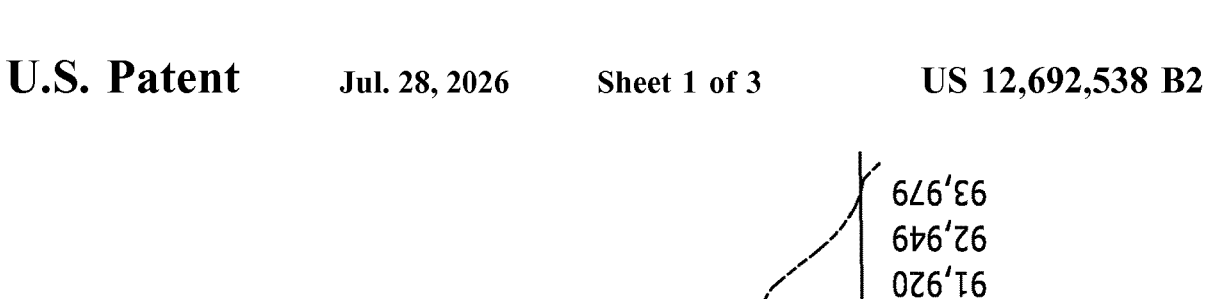
FIG. 1 is a graph showing the performance of the system presented in this invention with particular reference to the quality of melting curve. The black melting plot shows a better performance with a lower initial fluorescence background compared to melting curves obtained with standard PCR buffer (grey graph)

Reference will now be made in detail to the various embodiments of the invention, using the attached figures. Generally, only the differences with respect to individual embodiments are described. Each example is provided by way of explanation of the invention and is not meant as a limitation of the invention. For example, features illustrated or described as part of one embodiment can be used on or in conjunction with other embodiments to yield yet a further embodiment. It is intended that the present invention includes such modifications and variations.

Before describing these embodiments, it shall be also clarified that the present description is not limited in its application to details of the construction and disposition of the components as described in the following description using the attached drawings. The present description can provide other embodiments and can be obtained or executed in various other ways. It shall also be clarified that the phraseology and terminology used here is for the purposes of description only, and cannot be considered as limitative.

All the percentages and ratios indicated refer to the weight of the total composition (for example indicated as % w/w), unless otherwise indicated. All the measurements are made, unless otherwise indicated, at 25° C. and atmospheric pressure. All the temperatures, unless otherwise indicated, are expressed in degrees Centigrade.

All the ranges reported here shall be understood to include the extremes, including those that report an interval "between" two values. Furthermore, all the ranges reported here shall be understood to include and describe the punctual values included therein, and also all the sub-intervals. Moreover, all the ranges are intended as such that the sum of the values comprised therein, in the final composition, gives 100%, in particular considering that the person of skill will know how to choose the values of the ranges so that the sum does not exceed 100%.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, it will be readily apparent to one of ordinary skill in the art in light of the teachings herein that certain changes and modifications may be made thereto without departing from the spirit and scope of the appended claims. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. To the extent such publications may set out definitions of a term that conflicts with the explicit or implicit definition of the present disclosure, the definition of the present disclosure controls. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Embodiments of the present disclosure generally relate to molecular fingerprinting method to detect and characterize DNA targets in a sample through PCR is provided. The method of the present disclosure is able to discriminate and genotype different strains of the same pathogen, different pathogens belonging to separated genus and genetic variations in a single reaction. In one embodiment, the method includes:

providing a PCR reaction mixture comprising an amplification buffer comprising an intercalating molecule or compound incorporated into the double-stranded amplicon and emitting a detectable signal;

performing PCR amplification using said PCR reaction mixture and said sample;

performing, at the end of the PCR amplification, a HRM analysis on said PCR reaction mixture and said sample previously subjected to PCR amplification;

wherein the PCR reaction mixture comprises two or more pairs of amplification primers for amplifying in a multiplex approach two or more target nucleic acids, wherein said amplification primers are designed in order to generate amplicons with a different melting temperature each other in order to discriminate, in the HRM analysis, each amplicon by observing the specific melting temperature of each amplicon, wherein the method further comprises monitoring, during the HRM analysis, the change in the signal emission resulting from the temperature-induced denaturation of the double-stranded amplicons into two single-stranded DNA, due to the release of the intercalating molecule or compound, wherein the method further comprises determining discrimination and genotyping of different strains of the same pathogen, different pathogens belonging to separated genus and genetic variations in the sample, through a reader analysing the signal variation and obtaining the result of the analysis through a graphic interface connected to said reader.

According to embodiments, combinable with all embodiments described herein, the DNA target that can be detected and genotyped is a pathogen DNA target.

Advantageously, using the embodiments described herein, it is possible to detect and discriminate:

different types of a specific pathogen (e.g. the 14 different high risk HPV strains);

different pathogens (e.g. different pathogens responsible for sexually transmitted diseases, such as HPV, syphilis infection, gonorrhoea infection, HIV);

different alleles of a cell gene (e.g. different mutations of the human BRCA gene);

different allele of several cell genes (e.g. different mutations of BRCA gene, of K-RAS gene or other genes).

Advantageously, the sample can be a crude sample. The crude sample can be vaginal or cervical mucus, other bodily fluids, saliva, blood, urine, biopsies, formalin-fixed paraffin-embedded (FFPE) tissue, cells, fine needle aspiration biopsies or similar. The crude sample can be diluted prior to performing the PCR amplification and HRM analysis.

According to possible embodiments, combinable with all embodiments described herein, the signal variation between an input and an output signal can be detected in a circuit comprised in the reader, wherein said variation is a function of the presence, amount, genotype of different strains of the same pathogen, different pathogens belonging to separated genus and genetic variations present in the sample.

According to embodiments, combinable with all embodiments described herein, performing PCR amplification using said PCR reaction mixture includes amplifying the target purified nucleic acid using said PCR reaction mixture to generate an amplicon or amplification product.

According to embodiments, combinable with all embodiments described herein, the amplification primers are sufficiently complementary to the target nucleic acid to hybridize therewith and trigger polymerase-mediated synthesis.

In one specific embodiment, combinable with all embodiments described herein, the amplification primers are designed to amplify specifically pathogen DNA targets (e.g. HPV genotypes) producing corresponding amplicons, each from 38 to 1500 base pairs (bps).

In one further specific embodiment, combinable with all embodiments described herein, the amplification primers are designed to amplify an amplicon wherein the melting peak of the amplicon is between 68 and 95° C.

In still another embodiment, combinable with all embodiments described herein, each amplification primer is present in the PCR reaction mixture at a final concentration range from 50 to 1000 nanomolar (nM).

According to embodiments, combinable with all embodiments described herein, the PCR reaction mixture comprises the amplification primers and the amplification buffer.

According to embodiments, the amplification buffer is comprised in a diagnostic kit that is part of the present disclosure.

In one embodiment, combinable with all embodiments described herein, besides the above mentioned two or more pairs of amplification primers, the PCR reaction mixture comprises a DNA polymerase. The DNA polymerase is comprised in said amplification buffer. The DNA polymerase is an enzyme that polymerizes new DNA strands. For instance, heat resistant or heat stable polymerase can be used, since it is more likely to remain intact during the high-temperature DNA denaturation process. One example of heat resistant or heat stable polymerase that can be used in embodiments described herein is taq polymerase. Moreover, the polymerase that can be used in association with embodiments described herein is a hot-start polymerase. In a possible implementation, the hot-start polymerase can be (Hot Start) @Taq DNA Euroclone, (Hot Start) Phire Thermo Scientific, (Hot Start) Phusion Thermo Scientific, or (Hot Start) Gold Taq polymerase Sigma.

In one further embodiment, combinable with all embodiments described herein, the PCR reaction mixture may further comprise deoxynucleoside triphosphates (dNTPs) or analogues. dNTPs or analogues are comprised in said amplification buffer. dNTPs or analogues are used to provide the building blocks from which the DNA polymerase synthetizes a new DNA strand. dNTPs can be substituted by functional analogues like adenine, cytosine, guanine, thymine, uracil, orotidine, inositate, xanthylate.

As above described, the PCR reaction mixture comprises said intercalating molecule or compound, being incorporated into the double-stranded amplicon or amplification product and emitting fluorescence or any other detectable signal. The intercalating molecule or compound can be comprised in said amplification buffer.

In particular, according to embodiments, the intercalating molecule can be any sensor or reporter molecule emitting a signal that can be detected by a reader analysing an electric signal variation in terms of inductance, current, electric potential, in case of conductimetric, amperometric, voltammetric detection, or the presence of light at specific wavelengths, in case of a fluorescence/chemiluminescence detection, or light scattering and/or refraction/diffraction phenomena, in case of a plasmonic optical detection.

For instance, in some implementations the intercalating molecule or compound can be an intercalating dye emitting fluorescence. According to possible implementations, specific DNA intercalating dye, at a final concentration range from 1 to 8 μM, can be one or more of the following dyes: SYTO-9, SYTO-13, SYTO-16, SYTO-64, SYTO-82, YO-PRO-1, SYTO-60, SYTO-62, TOTO-3, POPO-3, BOBO-3, doxorubicin-conjugated quantum dot nanoparticles or similar.

In yet another embodiment, combinable with all embodiments described herein, the PCR reaction mixture may further comprise a buffer solution. The buffer solution is comprised in said amplification buffer. The buffer solution provides a suitable chemical environment for optimum activity and stability of DNA polymerase. For instance, the buffer solution may comprise water, in particular deionized water, TrisHCl and/or KCl and possibly in some cases MgCl$_2$.

In one embodiment, combinable with all embodiments described herein, the PCR reaction mixture may further comprise a pH stabilizer.

In one further embodiment, combinable with all embodiments described herein, the PCR reaction mixture may further comprise preservatives.

In still another embodiment, combinable with all embodiments described herein, the PCR reaction mixture may further comprise water.

In yet another embodiment, combinable with all embodiments described herein, the PCR reaction mixture may further comprise a source of monovalent or bivalent cations. The source of monovalent or bivalent cations is comprised in said amplification buffer. For example, a chloride containing monovalent ion or bivalent ions can be used. As a source of monovalent cations, potassium ions can be used. K$^+$ can be obtained from potassium salts, e.g. potassium chloride, in particular potassium chloride at a concentration of about 0.1 M. As source of bivalent cations magnesium or manganese ions can be used. Mg$^{2+}$ can be obtained from magnesium salts, e.g. magnesium chloride.

In one further embodiment, combinable with all embodiments described herein, the PCR reaction mixture may further comprise bovine serum albumin (BSA). The BSA is comprised in said amplification buffer.

In one further embodiment, combinable with all embodiments described herein, the PCR reaction mixture further comprises one or more detergents. In possible implementations, said detergent can be Nonidet-P40 at a concentration of about 0.5%.

In still another embodiment, combinable with all embodiments described herein, the PCR reaction mixture may further comprise additives. The additives can be comprised in some embodiments of the above-mentioned amplification buffer. In possible implementations, the additives that can be used are selected among one, more or all of additives in a group comprising: NP40, DMSO, TMAC (Tetramethylammonium Chloride), Acetamide, Triton, Formamide, Betaine,

*E. coli* ssDNA binding protein, Glycerol, L-Carnitine and Gelatine. Advantageously, in embodiments exploiting a fluorescence detection, the presence of additives can be important to avoid a high basal fluorescence background allowing an increased diagnostic sensitivity, specificity and accuracy (see FIG. 1). In some possible implementations, the additives may further comprise a gelatin, for example at a concentration of about 0.1%. In yet further possible implementations, the additives may further comprise an enhancer. For example, the enhancer can be L-Carnitin at a concentration of about 0.42M. In still further possible implementations, the additives may further comprise sugar alcohol, for example sorbitol at a concentration of about 25 mM.

According to embodiments, combinable with all embodiments described herein, amplifying the target purified nucleic acid using said PCR reaction mixture, to generate an amplicon or amplification product, includes thermocycling by performing a ramp of temperature steps. In one possible implementation, a ramp of temperature includes performing the following temperature steps:

> denaturation at 95-98° C. from 1 to 30 seconds;
> annealing in a range between 50° C. and 70° C. from 1 to 60 seconds;
> extension in a range between 60° C. and 75° C. from 0 second to 5 minutes.

In possible implementations, the number of cycles of thermocycling is of at least 30 cycles, for instance between 30 and 50 cycles. One possible example is 35 cycles.

In one possible implementation, hot-start polymerase can be used. Hot-start PCR avoids a non-specific amplification of DNA by inactivating the polymerase at lower temperatures, for instance through antibodies interaction, chemical modification or aptamer technology. Typically, a specific inhibitor, such as an aptamer-based inhibitor or specific antibodies can be used to block the polymerase at lower temperatures. If hot-start polymerase is used, an initial incubation step which ranges from 95° C. to 98° C. for 1 second to 10 minutes is performed. This initial incubation step is necessary for activation of polymerase.

According to embodiments, combinable with all embodiments described herein, the method includes, during thermocycling in the PCR amplification, performing the monitoring emission signal changing, e.g. fluorescence, resulting from the temperature-induced denaturation of the double-stranded amplicons or amplification products into two single-stranded DNA, due to the releasing of the intercalating molecule or compound, i.e. intercalating dye. The intercalating molecule or compound binds to DNA in the double-strand configuration. At each amplification cycle, amplicons are generated in which the intercalating molecule or compound binds in the extension step, during which the signal (e.g. fluorescence) is acquired.

Advantageously, the PCR reaction can occur in a real-time PCR machine, that allows monitoring the change in the signal, e.g. fluorescence, emission at each amplification cycle in the PCR amplification, in turn allowing quantification of the presence of amplicons and quantification, therefore, of the viral DNA in the amplification phase.

In other embodiments, the PCR amplification may occur in a thermocycling machine able to acquire said signal emission each 0.1° C./second or less.

According to embodiments, combinable with all embodiments described herein, the HRM analysis includes performing a ramp of temperature on the PCR reaction mixture previously subjected to PCR amplification. In one possible implementation, a ramp of temperature includes performing the following temperature steps:

> incubation at 95° C. from 1 seconds to 60 seconds
> incubation at 60° C. from 1 seconds to 2 minutes
> ramping up to 95° C. increasing the temperature 0.1° C./second or less, and performing said monitoring the change in the signal, e.g. fluorescence, emission resulting from the temperature-induced denaturation of the double-stranded amplicons or amplification products into two single-stranded DNA, due to the release of the intercalating molecule or compound, i.e. intercalating dye.

Figure 2:
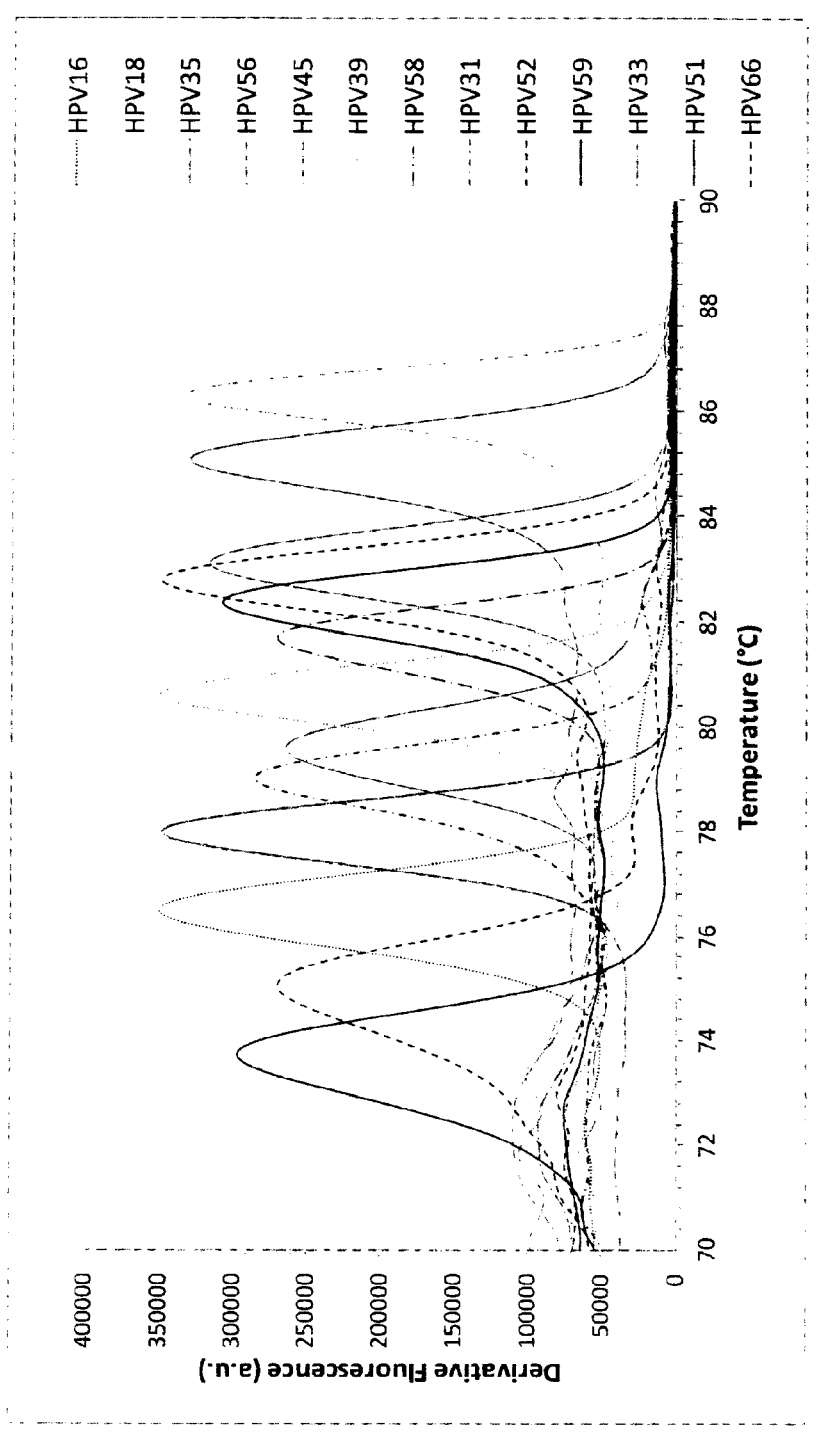
FIG. 2 is a graph showing Derivative Fluorescence vs. Temperature curves with specific primers designed to obtain different melting temperature for each HPV genotype, allowing simultaneous precise identification of the most common high risk genotypes.

Advantageously, monitoring the change in the signal, e.g. fluorescence, emission in the HRM analysis, during which the large quantity of viral amplicons generated after the plurality of amplification thermocycling, allows to analyse the melting features of such amplicons at different temperatures. At low temperature, e.g. 60° C., amplicons are all double-stranded and the maximum level of signal, e.g. fluorescence, is detected. By slowly increasing temperature, however, amplicons start to denaturate up to complete separation into two single-stranded DNA and at this point the signal, e.g. fluorescence, will not be generated anymore. For instance, the shape and development of the Derivative Fluorescence vs. Temperature curves, as shown in FIG. 2, that can be generated by the above-mentioned monitoring, change depending on the sequence. The present disclosure exploits this feature to discriminate the viral genotype, because the primes used are designed such as to generate amplicons with a specific and different melting temperature each. In other words, the amplification primers designed according to the present disclosure allow to amplify amplicons with a precise and specific melting temperature fingerprint each.

Therefore, according to advantageous embodiments using a real-time PCR machine, after monitoring the change in in the signal, e.g. fluorescence, emission at each amplification cycle in the real-time PCR, it will be possible to know if the analysed sample is infected or not by a pathogen or a group of pathogens, e.g. a virus, and also by which one of the possible genotypes that can be detected.

Moreover, according to the present disclosure, after monitoring the change in in the signal, e.g. fluorescence, emission in the HRM analysis it will be possible to know, in the case that a sample is infected, also exactly the specific genotype or strain of the pathogen infecting the sample, or which exact pathogen of the group of pathogens.

The overall result is therefore that it will be possible, in advantageous embodiments using the real-time PCR, to know, via the real-time PCR, if a patient if positive or not to a specific pathogen, or a group of pathogens and, when positive, to know, via HRM analysis, the genotype or strain of pathogen that is infecting the patient or to know the specific pathogen from the detected group of pathogens.

Figure 3:
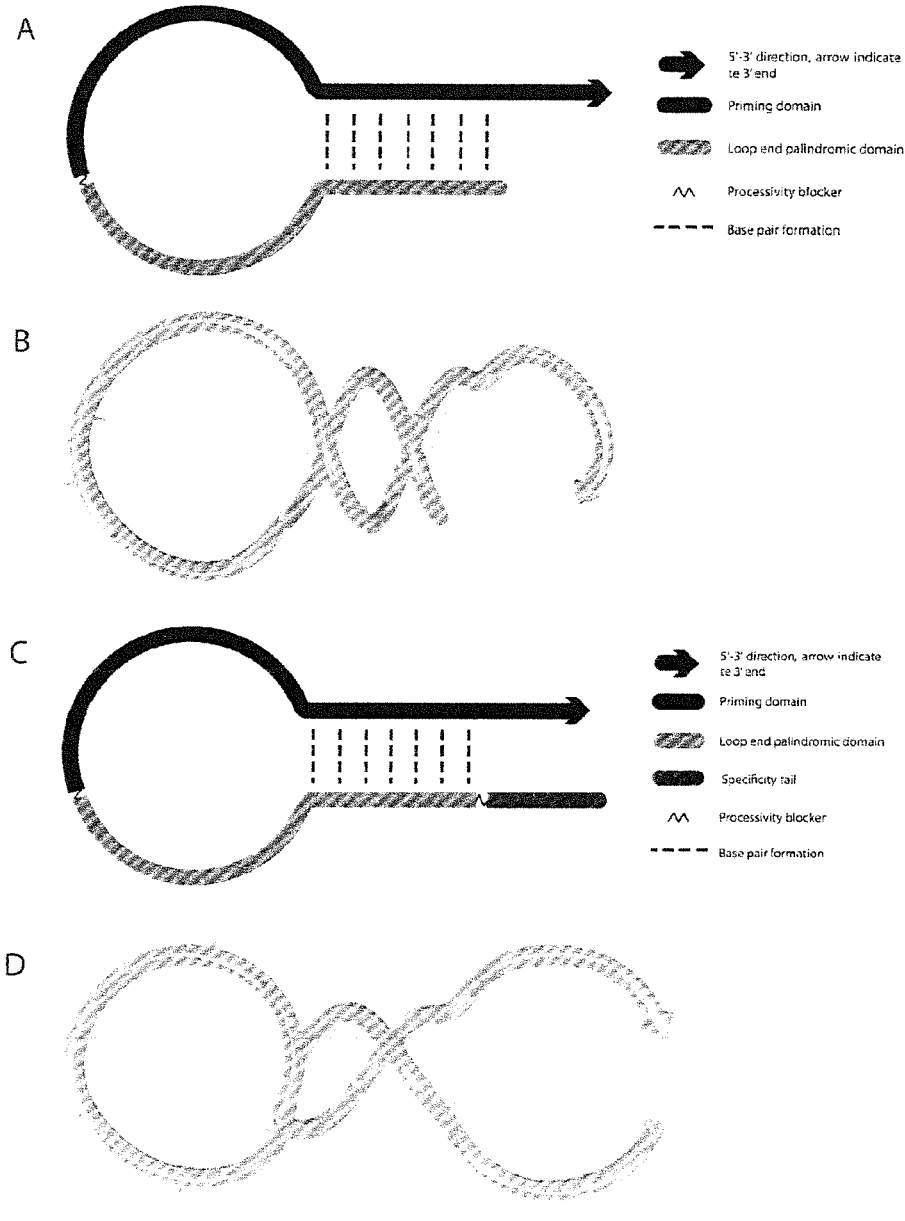
FIG. 3 shows hybrid primers structures, in schematic and 3D-structures, with (A and B) and without (C and D) the 5' fidelity tail.

In still further embodiments described using FIG. 3, which are combinable with all embodiments described herein, in case a formation of primer dimers causes aspecific fluorescent background, one or more of the above-mentioned amplification primers are specific stem-loop hybrid primers designed to reduce the formation of primer dimers. These specific stem-loop hybrid primers are therefore specific variants of the amplification primers described above and used in the PCR reaction mixture. Advantageously, said particular stem-loop hybrid primers are included in amplification reaction to avoid primer dimers and aspecific primer interactions with off target template sequences. These stem-loop hybrid primers enable to design amplicons with a very specific predicted melting temperature, facilitating the amplicon temperature melting-dependent design, due to their chemical composition that impedes both the DNA polymerase adding supplementary DNA bases and primer heterodimer formation. These stem-loop hybrid primers are DNA oligonucleotides that differ from standard primers in terms of structure and chemical composition.

The stem-loop hybrid primers according to embodiments described herein act through two distinct mechanisms: a competitive mechanism that protects the primer from both aspecific interactions and self-interaction; and a DNA polymerase stop-system that allows to generate only the desired amplicon with the predicted melting features. The oligonucleotides of the stem-loop hybrid primers are structured in 4 domains: 1) a priming portion, 2) a loop portion, 3) a competitive palindromic portion and 4) a 5' fidelity tail (see FIG. 3).

According to embodiments, the priming portion 1) is a sequence present in the actual primer sequence that is complementary to the target sequence and it may range from 15 to 60 bases. The target sequence is a DNA sequence present in the pathogen genome that has at least 50% of identity with the priming portion.

According to embodiments, the loop portion 2) can contain from 30% to 90% of the priming portion bases and it forms a stable and unique hairpin structure. The loop portion contains a number of nucleotides (adenine, cytosine, timine, guanine, uracil, orotidine, inosinate, xanthylate) or DNA base analogue, in order to form a stable loop structure. Juxtaposed to the 5' of the priming portion, the sequence of the loop portion contains a DNA polymerase stopping site (processivity blocker). This stopping site can be modulated by the presence of at least one 1,2-Dideoxyribose, or an equivalent abasic nucleotide, preceded or followed by at least one 1,2-Dideoxyribose or at least one polyethylen glycol. The stopping site can be formed even by only PEG (polyethylene glycol) molecules in a structure which has the space-filling of at least 2 nucleotides. In this embodiment, several members of PEG family are suitable, but the preferential molecule is triethylene glycol (TEG).

According to embodiments, the competitive palindromic portion 3) is complementary to the sequence of the priming portion. The competitive palindromic portion is at least one nucleotide shorter than the priming sequence. The 5' end of the competitive palindromic portion contains a DNA polymerase stopping site (processivity blocker) composed as described above with reference to the loop portion 2).

According to embodiments, the 5' fidelity tail length ranges from 1 to 1000 nucleotides, it contains bases or bases analogues (adenine, cytosine, timine, guanine, uracil, orotidine, inosinate, xanthylate) and is complementary or partially complementary to the downstream region of the target sequence.

In still further embodiments, in case a formation of primer dimers causes aspecific fluorescent background, decoy oligonucleotides can be employed in the PCR reaction mixture as above-described, in order to decrease the aspecific signal due to primer-dimer formations. Decoy oligonucleotides generally are oligonucleotide fragments able to bind to and block transcription and respectively translation factors. In these embodiments, decoy oligonucleotides range from 10 to 100 nucleotides, and are complementary for at least 50% to the specific amplification primers as above described. Decoys oligonucleotides are defined by a 3' overhang on one side and by a 5' blunt extremity on the other side. The difference between the melting temperature of each decoy oligonucleotide and the relative paired primer does not exceed 2° C.

Decoy oligonucleotides can be advantageous since they can prevent the amplification primers from aspecific interaction that create free 3' OH groups, accessible by polymerase, because their sequence is complementary to the amplification primers, their melting temperature is slightly lower and they do not create structures that expose free 3' OH groups.

According to embodiments, combinable with all embodiments described herein, PCR amplification can be for instance performed in a PCR thermocycler.

According to further embodiments, combinable with all embodiments described herein, PCR amplification can be typically performed in a real-time PCR machine, for instance a real-time PCR thermocycler.

Since, according to the present disclosure, the same sample is first subjected to the PCR amplification and then to HRM analysis, the whole method can be performed in a single apparatus, in particular a real-time PCR machine.

According to possible embodiments, the PCR amplification and detection can be performed simultaneously by means of Real Time PCR in any setup known in the art, including quantitative Real time PCR allowing assessment of the pathogenic load in the infected sample, followed by HRM analysis, performed in the same real-time PCR machine.

However, in other embodiments, the two operations, i.e. PCR amplification and HRM analysis, can also be performed in separate and distinct apparatuses coupled or associated each other, for instance a typical thermocycler for the PCR amplification and then a real-time PCR configured for HRM analysis.

For example, in possible implementations, the detection can be performed using a dedicated PCR device, also in portable format, containing a specific Peltier module coupled with a fluorescence optical reader or other appropriate reading device, able to perform HRM analysis.

In still further implementations, the detection via the PCR amplification can be performed using a dedicated PCR device containing for instance a specific Peltier module coupled to a read-out device different than a fluorescent read-out device, for instance a chemiluminescent or electrochemical read-out device, a conductimetric, amperometric, voltammetric read-out device, plasmonic optical red-out device or any other suitable read-out device.

Embodiments described herein can be used for diagnostic purposes. In particular, in the following, specific ranges of the reagents present in the two possible implementations of the PCR reaction mixture are described, that can be used for diagnostic purposes. Subsequently, specific ranges are described that can be used for specific detection of the HPV DNA.

In particular, the method and diagnostic kit containing the above-mentioned PCR reaction mixture according to the present disclosure can be used to detect clinical pathogens present in the sample, preferably blood borne pathogens including their genetic sequences.

In one embodiment, a possible first amplification buffer for diagnostic purposes comprises the dNTPs, the source of mono or bivalent cations, the buffer solution, the BSA, the Hot Start DNA polymerase, the intercalating molecule or compound. For instance, one specific implementation of the first amplification buffer comprises:

a) dNTPs (final concentration range: from 0.05 mM to 0.3 mM)
  b) MgCl$_2$ (final concentration range: from 0.3 mM to 4 mM)

15 c) TrisHCl buffer solution (final concentration range: from 10 mM to 50 mM; pH from 6.00 to 10.00)

d) KCl (final concentration range: from 10 mM to 50 mM)

e) BSA (final concentration range: from 0.005 to 0.05 mg/ml)

f) Hot Start polymerase g) SYTO-9 (final concentration range: from 1 μM to 8 μM).

In another possible embodiment, a possible alternative second amplification buffer for diagnostic purposes is provided, that comprises the dNTPs, the source of mono or bivalent cations, the buffer solution, BSA, the hot start DNA polymerase, the intercalating molecule or compound and the above mentioned additives. By the addition of additives, the second amplification buffer can be used as a PCR enhancer buffer providing increased diagnostic sensitivity, specificity and accuracy as above discussed. For instance, one specific implementation of the alternative second amplification buffer comprises:

a) dNTPs (final concentration range: from 0.05 mM to 0.5 mM)

b) MgCl₂ (final concentration range: from 0.3 mM to 4 mM)

c) TrisHCl buffer solution (final concentration range: from 10 mM to 50 mM; pH from 6.00 to 10.00)

d) KCl (final concentration range: from 10 mM to 50 mM)

e) BSA (final concentration range: from 0.005 to 0.05 mg/ml)

f) Hot start polymerase g) SYTO-9 (final concentration range: from 1 μM to 8 μM)

h) TMAC (Tetramethylammonium Cloride) (final concentration range: from 10 mM to 100 mM)

i) Acetamide (final concentration range: from 0% to 5%)

j) Formamide (final concentration range: from 0% to 5%)

k) Betaine (final concentration range: from 0 μM to 3 mM)

l) Gelatine (final concentration range: from 0.01 mg/ml to 1 mg/ml).

In the embodiments of methods and diagnostic kit described herein for diagnostic purposes, since different PCR machine, i.e. different thermocycler models, may generate different curves and in particular different melting peaks, a calibrator is provided to set each real-time PCR machine for a correct and precise melting analysis required to genotype the pathogen. Indeed, some variations might occur due to machine type, efficiency due to maintenance status or acquisition settings, and the calibrator allows the adjustment of the observed measurements in a specific machine. The calibrator can be composed by synthetic oligonucleotides corresponding to the amplicons generated by the specific primers of the PCR reaction mixture according to the present disclosure. Advantageously, a machine-specific calibrator can be loaded in PCR runs periodically to check the effective melting temperature of the amplicons of a particular thermocycler machine, and compare it with the expected melting temperature.

Further embodiments described herein for diagnostic purposes provide primers for obtaining combinations of melting temperature, in order to increase the number of targets detectable in the same assays. The limit of the number of targets simultaneously detectable in a single well of a PCR machine is generally defined by the capability of the system to distinguish and resolve two proximal peaks. However, according to embodiments described herein, it is possible to increase the number of targets detectable in the same assays, providing two or more sets of primers that are specific for the same DNA targets. According to embodiments, a first set of primers is present in a PCR reaction mixture in one well, at least a second set is present in another well. Each set of primers comprises primers each recognizing one specific DNA target. The DNA targets recognized by the first set of primers are the same as the DNA targets recognized by the second set of primers and the melting temperature of an amplicon generated by a primer of one set of primers recognizing a specific DNA target is different from the melting temperature of an amplicon generated by a primer of the other set of primers recognizing said specific DNA target.

As indicated in the table below as an example, 3 targets are identified by two primer sets: Target #1 is recognized by set A and B, Target #2 is recognized by set C and D, Target #3 is recognized by set E and F. The PCR reaction mixture aliquoted in the well 1 contains primer sets A, C and E; the PCR reaction mixture aliquoted in the well 2 contains primer sets B, D and F.

| Target | Well 1 | Well 2 |
|---|---|---|
| Target#1 | Primer set A | Primer set B |
| Target#2 | Primer set C | Primer set D |
| Target#3 | Primer set E | Primer set F |

For each target DNA, HRM data will be collected for each well; hence each target DNA will be defined not by one single melting peak, but for several melting peaks, one for each well, as indicated in the table below as an example:

| Target | $T_m$ well 1 | $T_m$ well 2 |
|---|---|---|
| Target#1 | 70° C. | 71° C. |
| Target#2 | 70° C. | 82° C. |
| Target#3 | 74° C. | 70° C. |

These embodiments allow the discrimination of more targets DNA thanks to the exponential increase in the number of possible combinations of the two or more melting temperatures that will be revealed, representing each of them a variable; thus, each target DNA will be precisely defined according multiple variables.

If x is the number of possible peaks distinguishable in a single well, the number of targets distinguishable in this embodiment is $x^a$, where a is the number of sets of primers used for each target, and consequently the number of wells used for each sample.

This variant is particularly useful when the application aims at differentiating high number different targets (such as it occurs in HPV genotyping, where 40 genotypes can be simultaneously analysed and defined by the embodiments according to the present disclosure).

In the following, embodiments of methods and diagnostic kit according to the present disclosure are described for specific use for HPV diagnosis, using specific primers.

In one embodiment, methods and diagnostic kit of the present disclosure are used to detect Human Papillomavirus DNA in clinical samples and to discriminate different genotypes by HRM analysis.

According to one embodiment, the methods and diagnostic kit, in addition to any of the afore-described combination of reagents required for carrying out DNA amplification by PCR, includes specific primers for each genotype of HPV are included from SEQ ID NO: 20 to SEQ ID NO: 616 and from SEQ ID NO: 655 to SEQ ID NO: 706 provided in the sequence listing attached hereto. The afore-mentioned specific primers for HPV diagnosis are characterized by the following features:

1) difference in melting temperature of different primers does not exceed 30° C.

2) primers amplify HPV genotypes producing amplicons from 40 to 1500 bps.

3) primers amplify an amplicon wherein the melting peak of the amplicon is between 68 and 95° C.

4) each primer is present in the PCR reaction mixture at a final concentration range from 50 to 1000 nM.

In yet further embodiments, one further set of normalizing primers can be provided, for the amplification of human genomic DNA, said amplification of human genomic DNA serving as an internal PCR validation control and/or control for normalization of the amplified pathogen, e.g. HPV, DNA obtained according to any of the embodiments described herein. An example of such pair of normalizing primers targeting a fragment from the human beta-globin gene is provided in SEQ ID NOs: 617-631 of the sequence listing attached hereto.

In a preferred embodiment of the diagnostic kit for HPV diagnosis, specific primers for the 13 most frequent high risk HPV serotypes are provided in the PCR reaction mixture of the present disclosure, that have the sequences SEQ ID NO: 591 to SEQ ID NO: 616 of the sequence listing attached hereto.

In one embodiment, a specific amplification buffer for HPV diagnosis comprises the following reagents with concentration expressed as ranges:

a) dNTPs (final concentration range: from 0.05 mM to 0.5 mM)

b) $MgCl_2$ (final concentration range: from 0.3 mM to 4 mM)

c) TrisHCl buffer solution (final concentration range: from 10 mM to 50 mM; pH from 7.00 to 10.00)

d) KCl (final concentration range: from 10 mM to 50 mM)

e) BSA (final concentration range: from 0.005 mg/ml to 0.05 mg/ml)

f) Hot start polymerase g) SYTO-9 (final concentration range: from 1 μM to 8 μM).

One example of possible specific concentration values of the reagents is the following:

a) dNTPs (final concentration 0.2 mM)

b) $MgCl_2$ (final concentration 0.75 mM)

c) TrisHCl buffer solution (final concentration 30 mM: and pH 9.0)

d) KCl (final concentration 50 mM)

e) BSA (final concentration 10 μg/ml)

f) Hot Start polymerase g) SYTO-9 (final concentration 4 μM).

In another possible embodiment, a further alternative possible specific amplification buffer for HPV diagnosis, providing increased diagnostic sensitivity, specificity and accuracy comprises the following reagents with concentration expressed as ranges:

a) dNTPs (final concentration range: from 0.05 mM to 0.3 mM)

b) $MgCl_2$ (final concentration range: from 0.3 mM to 4 mM)

c) TrisHCl buffer solution (final concentration range: from 10 mM to 50 mM; pH from 7.00 to 10.00)

d) KCl (final concentration range: from 10 mM to 50 mM)

e) BSA (final concentration range: from 0.005 mg/ml to 0.05 mg/ml)

f) Hot start polymerase g) SYTO-9 (final concentration range: from 1 μM to 8 μM)

h) TMAC (Tetramethylammonium Chloride) (final concentration range: from 10 mM to 100 mM)

i) Acetamide (final concentration range: from 0.5% to 5%)

j) Formamide (final concentration range: from 0.5% to 5%)

k) Betaine (final concentration range: from 100 μM to 3 mM)

l) Gelatine (final concentration range: from 0.01 mg/ml to 1 mg/ml).

One example of possible specific concentration values of the reagents of this further alternative amplification buffer is the following:

a) dNTPs (final concentration 0.15 mM)

b) $MgCl_2$ (final concentration 0.75 mM)

c) TrisHCl buffer solution (final concentration 30 mM; pH 9)

d) KCl (final concentration: 40 mM)

e) BSA (final concentration 10 μg/ml)

f) Hot start polymerase g) SYTO-9 (final concentration 2 μM)

h) TMAC (Tetramethylammonium Chloride, final concentration of 75 mM)

i) Acetamide (final concentration 3%)

j) Formamide (final concentration 1.5%)

k) Betaine (final concentration 0.5M)

l) Gelatine (final concentration 0.1 mg/mL).

Advantageously, the diagnostic HPV test based on the embodiments described herein can provide at least two important information about HPV testing and screening:

1) a diagnostic information: the amplification curves obtained by the PCR allow the detection of the first 14 high risk genotypes (HPV 16, 18, 31, 33, 35, 39, 45, 51, 52, 56, 58, 59, 66, and 68—Cit. IARC 2009) and thus give a diagnostic information. A sample is positive when the amplification curve occurs before 35 PCR cycles using a fluorescence threshold that range from 250.000 to 400.000. The present invention has been tested on positive samples (extracted DNA of 150 women with a CIN2+ cytology, according with Mejer guide lines, 2009). Clinical data showed that sensitivity of the diagnostic HPV test according to the embodiments described herein, intended as the sensitivity to detect High-Grade Squamous Intraepithelial Lesions (HSIL or CIN2/3 lesions, that are considered the clinical endpoint in the HPV diagnostics), is 98%. Sensitivity is the percentage of HPV-infected people with a diagnosed HSIL that are detected by the HPV test according to the embodiments described herein, divided by the total number of HPV-infected people with a diagnosed HSIL detected by conventional test (e.g. Pap test). The test specificity reaches almost the 100% and the test accuracy ranges from 0.93 to 0.98;

2) the melting fingerprinting analysis obtained by the HRM analysis allows the genotyping of all the above-mentioned 14 high risk HPV genotypes. Indeed, the HPV vaccine administration is changing the HPV genotypes prevalence among different populations, and some High Risk HPVs, once very rare, are becoming more frequent. Besides that, this information is also important in later, possible triage steps because different HPV genotypes have different capabilities to induce cancer development. Genotyping is also able to distinguish between transient infections, that are very common and spontaneously resolved, and persistent infection of a certain high risk HPV type, that can eventually lead to cancer.

According to still further embodiments, combinable with all embodiments described herein, methods and diagnostic kit according to the present disclosure can be used to detect and discriminate further different pathogens responsible for other sexually transmitted diseases, such as chlamydia infection, syphilis infection, or gonorrhoea infection, by using specific amplification primers according to SEQ ID NO: 1 to SEQ ID NO: 19 and from SEQ ID NO: 636 to SEQ ID NO: 654 of the sequence listing attached hereto in the PCR reaction mixture as above described.

While the foregoing is directed to embodiments of the invention, other and further embodiments of the invention may be devised without departing from the basic scope thereof, and the scope thereof is determined by the claims that follow.

BIBLIOGRAPHY

1. Munoz et al. HPV and the ethiology of human cancer. Vaccine (2006).
2. Herrero et al. Human Papillomavirus and oral cancer: The International Agency for Research on Cancer multicentre study. J Natl Cancer (2003).
3. de Villiers et al., Classification of Papillomavirus. Virology (2004).
4. Munoz et al., Epidemiologic classification of Human Papillomavirus Types associated with cervical cancer. N Engl J Med (2003).
5. Cuzick et al., Overview of the European and North American studies on HPV testing in primary cervical cancer screening. Int J Cancer (2006).
6. Clavel et al. Human papillomavirus testing in primary screening for the detection of high-grade cervical lesions: a study of 7932 women. Br. J. Cancer (2001).
7. Ronco et al. Efficacy of human papillomavirus testing for the detection of invasive cervical cancers and cervical intraepithelial neoplasia: a randomized controlled trial. Lancet Oncol. (2010).
8. Arbyn et al. Evidence regarding human papillomavirus testing in secondary prevention of cervical cancer. Vaccine (2012).
9. Dillner et al. Long term predictive values of cytology and human papillomavirus testing in cervical cancer screening: joint European cohort study. BMJ (2008).
10. Söderlund-Strand et al. Genotyping of human papillomavirus in triaging of low-grade cervical cytology. Am J Obstet Gynecol (2011).
11. Naucler et al. HPV type-specific risks of high-grade CIN during 4 years of follow-up: a population-based prospective study. Br. J. Cancer (2007).
12. Pierce Campbell et al. Long-term persistence of oral human papillomavirus type 16: the HPV Infection in Men (HIM) study. Cancer Prev Res (Phila) (2015).
13. Donà et al. Incidence, clearance and duration of cutaneous beta and gamma human papillomavirus anal infection. J Infect October (2016).
14. Dillner et al. Translational mini-review series on vaccines: monitoring of human papillomavirus vaccination. Clin. Exp. Immunol. (2007).
15. Poljak et al. Commercially available molecular tests for human papillomaviruses (HPV): 2015 update. J Clin Vir (2015).

---

The invention claimed is:

1. A molecular fingerprinting method to detect and geno-type at least two pathogen DNA targets in a sample through polymerase chain reaction (PCR), said method comprising:

(a) providing a PCR mixture comprising an amplification buffer comprising an intercalating molecule or compound capable of incorporating into a double-stranded amplicon and emitting a detectable signal; wherein the PCR mixture comprises two or more pairs of amplification primers for amplifying in a multiplex approach two or more pathogen DNA targets, wherein said PCR mixture comprises a melting temperature calibrator to periodically check the effective melting temperature of the amplicons produced in a particular thermocycler machine, and compare it with an expected melting temperature, wherein said calibrator is a synthetic oligonucleotide having the same melting temperature as an amplicon generated by an amplification primer pair of the PCR mixture, wherein said amplification primers are designed in order to generate amplicons with a different melting temperature from each other in order to discriminate one amplicon from other amplicons by observing the specific melting temperature of each amplicon, (b) performing PCR amplification of the pathogen DNA targets using said PCR mixture in said sample to produce double-stranded amplicons;

(c) performing a High Resolution Melting (HRM) analysis on the PCR mixture and the sample subjected to PCR amplification in step (b);

(d) monitoring the change in the signal emission resulting from temperature-induced denaturation of the double-stranded amplicons into two single-stranded DNAs due to the release of the intercalating molecule or compound, and (e) discriminating between pathogen DNA targets in the sample, through a reader analysing the change in signal emission from step (d) and obtaining the result of the analysis through a graphic interface connected to said reader.

2. The method according to claim 1, wherein said amplification primers are designed to amplify pathogen DNA targets to produce amplicons with a length between 38 to 1500 bp.

3. The method according to claim 1, wherein each of the amplification primers is designed to generate an amplicon, wherein the melting peak of the amplicon is between 68 and 95° C.

4. The method according to claim 1, wherein each amplification primer is present in the PCR mixture at a final concentration of 50 to 1000 nanomolar (nM).

5. The method according to claim 1, wherein the amplification buffer of the PCR mixture further comprises a DNA polymerase, deoxynucleoside triphosphates (dNTPs) or analogues, water, a source of monovalent or bivalent cations, and bovine serum albumin (BSA).

6. The method according to claim 5, wherein the amplification buffer of the PCR mixture further comprises one or more additives selected from the group consisting of: DMSO, TMAC (Tetramethylammonium Chloride), acetamide, a detergent, formamide, betaine, E. coli ssDNA binding protein, glycerol, L-Carnitine and gelatine.

7. The method according to claim 1, wherein performing PCR amplification using said PCR mixture includes amplifying the pathogen DNA targets using said PCR mixture to generate at least two amplicons, wherein amplifying the pathogen DNA targets includes thermocycling by repeatedly performing a ramp of temperature, wherein, during thermocycling in the PCR amplification, monitoring the change in the signal emission resulting from the temperature-induced denaturation of the double-stranded amplicons into two single-stranded DNAs, due to the release of the intercalating molecule or compound, is performed, wherein said ramp of temperature comprises performing the following temperature steps:

denaturation at 95-98° C. from 1 to 30 seconds;

annealing in a range between 50° C. and 70° C. from 1 to 60 seconds; and extension in a range between 60° C. and 75° C. from 0 seconds to 5 minutes.

8. The method according to claim 1, wherein performing HRM analysis includes performing a ramp of temperature for HRM on the PCR mixture subjected to PCR amplification in step (b) and, during the ramp of temperature, performing said monitoring the change in the signal emission resulting from the temperature-induced denaturation of the double-stranded amplicons into two single-stranded DNA, due to the release of the intercalating molecule or compound, wherein said ramp of temperature comprises includes performing the following temperature steps:

incubation at 95° C. from 1 second to 60 seconds;

incubation at 60° C. from 30 seconds to 2 minutes; and ramping up to 95° C. increasing the temperature 0.1° C./second or less.

9. The method according to claim 1, wherein the PCR amplification occurs in a real-time PCR machine or in a thermocycling machine able to acquire said signal emission each 0.1° C./second or less.

10. The method according to claim 1, wherein said PCR amplification is performed in a thermocycler or in a real-time PCR thermocycler, wherein, when the PCR amplification is performed in a thermocycler, HRM analysis is performed in a separate instrument, while when the PCR amplification is performed in a real-time PCR thermocycler, HRM analysis is performed in the same real-time PCR thermocycler.

11. The method according to claim 1, wherein two or more further sets of primers are used, wherein a first set of primers is present in a PCR mixture in one well, at least a second set of primers is present in a PCR mixture in another well, and wherein each set of primers comprises primers each recognizing one specific pathogen DNA target, wherein the pathogen DNA targets recognized by the first set of primers are the same as the pathogen DNA targets recognized by the second set of primers, wherein the melting temperature of an amplicon generated by a primer of one set of primers recognizing a specific pathogen DNA target is different from the melting temperature of an amplicon generated by a primer of the other set of primers recognizing said specific pathogen DNA target, and wherein each pathogen DNA target is defined by a single melting peak in each well.

12. The method according to claim 1, wherein each of the pathogens is responsible for a sexually transmitted disease or infection.

13. The method according to claim 12, wherein the pathogens are different types of human papilloma virus (HPV).

14. The method according to claim 13, wherein the amplification primers are selected from SEQ ID NO: 20 to SEQ ID NO: 616 and from SEQ ID NO: 655 to SEQ ID NO: 706.

15. The method according to claim 12, wherein the pathogens are selected from pathogens responsible for chlamydia, pathogens responsible for syphilis, or pathogens responsible for gonorrhoea.

16. The method according to claim 15, wherein said amplification primers include one or more primers selected from the following primers: SEQ ID NOs: 1-19 and SEQ ID NOs: 636-654.

17. The method according to claim 1, wherein a set of normalizing primers is further used for amplification of human genomic DNA serving as an internal PCR validation control and/or as a control for normalization of the amplified pathogen DNA obtained.

18. The method according to claim 17, wherein said amplified pathogen DNA targets include HPV DNA and a pair of said normalizing primers targets a fragment from the human beta-globin gene and is selected from the primers set forth in SEQ ID NO: 617 to SEQ ID NO: 629.

* * * * *

SEQUENCE LISTING

```
<160> NUMBER OF SEQ ID NOS: 706

<210> SEQ ID NO 1
<211> LENGTH: 23
<212> TYPE: DNA
<213> ORGANISM: Chlamydia trachomatis

<400> SEQUENCE: 1
tgcagttgat caactcatcg gtt                                        23

<210> SEQ ID NO 2
<211> LENGTH: 20
<212> TYPE: DNA
<213> ORGANISM: Chlamydia trachomatis

<400> SEQUENCE: 2
tgaagcgctc cggatagtga                                           20

<210> SEQ ID NO 3
<211> LENGTH: 20
<212> TYPE: DNA
<213> ORGANISM: Chlamydia trachomatis

<400> SEQUENCE: 3
tgaagcgctc cggatagtga                                           20

<210> SEQ ID NO 4
<211> LENGTH: 20
<212> TYPE: DNA
<213> ORGANISM: Chlamydia trachomatis
```

-continued

```
<400> SEQUENCE: 4
tcactatccg gagcgcttca                                          20

<210> SEQ ID NO 5
<211> LENGTH: 27
<212> TYPE: DNA
<213> ORGANISM: Chlamydia trachomatis

<400> SEQUENCE: 5
gggtgtttgt actagaggaa ttacctc                                 27

<210> SEQ ID NO 6
<211> LENGTH: 20
<212> TYPE: DNA
<213> ORGANISM: Chlamydia trachomatis

<400> SEQUENCE: 6
ggcgatttgc cttaaccca                                          20

<210> SEQ ID NO 7
<211> LENGTH: 23
<212> TYPE: DNA
<213> ORGANISM: Chlamydia trachomatis

<400> SEQUENCE: 7
ggaaggatgc tgtttgcaaa ctg                                     23

<210> SEQ ID NO 8
<211> LENGTH: 24
<212> TYPE: DNA
<213> ORGANISM: Chlamydia trachomatis

<400> SEQUENCE: 8
gcgtcttgct aatgtagacc ctgc                                    24

<210> SEQ ID NO 9
<211> LENGTH: 25
<212> TYPE: DNA
<213> ORGANISM: Chlamydia trachomatis

<400> SEQUENCE: 9
gactgttgct tcgaagatcc atgcg                                   25

<210> SEQ ID NO 10
<211> LENGTH: 24
<212> TYPE: DNA
<213> ORGANISM: Chlamydia trachomatis

<400> SEQUENCE: 10
ctcaaggaat agtcgctata gcgc                                    24

<210> SEQ ID NO 11
<211> LENGTH: 24
<212> TYPE: DNA
<213> ORGANISM: Chlamydia trachomatis

<400> SEQUENCE: 11
cgctcctctg aagtcttaag cttg                                    24

<210> SEQ ID NO 12
<211> LENGTH: 23
<212> TYPE: DNA
```

<213> ORGANISM: Chlamydia trachomatis

<400> SEQUENCE: 12
cgcaaatctg aaagcatggg aac                                    23

<210> SEQ ID NO 13
<211> LENGTH: 26
<212> TYPE: DNA
<213> ORGANISM: Chlamydia trachomatis

<400> SEQUENCE: 13
cctaaaggtg tttttctgg caacag                                  26

<210> SEQ ID NO 14
<211> LENGTH: 26
<212> TYPE: DNA
<213> ORGANISM: Chlamydia trachomatis

<400> SEQUENCE: 14
cccgctattc cattgaaaga ttttgg                                 26

<210> SEQ ID NO 15
<211> LENGTH: 26
<212> TYPE: DNA
<213> ORGANISM: Chlamydia trachomatis

<400> SEQUENCE: 15
cccgctattc cattgaaaga ttttgg                                 26

<210> SEQ ID NO 16
<211> LENGTH: 24
<212> TYPE: DNA
<213> ORGANISM: Chlamydia trachomatis

<400> SEQUENCE: 16
aggaattacc tcttccccag aaca                                   24

<210> SEQ ID NO 17
<211> LENGTH: 25
<212> TYPE: DNA
<213> ORGANISM: Chlamydia trachomatis

<400> SEQUENCE: 17
agcattagct catcccgatt gtcct                                  25

<210> SEQ ID NO 18
<211> LENGTH: 25
<212> TYPE: DNA
<213> ORGANISM: Chlamydia trachomatis

<400> SEQUENCE: 18
acaaatactc tcccatttct cccac                                  25

<210> SEQ ID NO 19
<211> LENGTH: 19
<212> TYPE: DNA
<213> ORGANISM: Chlamydia trachomatis

<400> SEQUENCE: 19
tggtgcgtat cccctccgc                                         19

<210> SEQ ID NO 20
<211> LENGTH: 20

<212> TYPE: DNA
<213> ORGANISM: Human Papillomavirus

<400> SEQUENCE: 20
tttagatttg gaacccgagg                                                        20

<210> SEQ ID NO 21
<211> LENGTH: 20
<212> TYPE: DNA
<213> ORGANISM: Human Papillomavirus

<400> SEQUENCE: 21
ttatgctggc agttccagac                                                        20

<210> SEQ ID NO 22
<211> LENGTH: 20
<212> TYPE: DNA
<213> ORGANISM: Human Papillomavirus

<400> SEQUENCE: 22
tgtttaatgc acaggaaggg                                                        20

<210> SEQ ID NO 23
<211> LENGTH: 20
<212> TYPE: DNA
<213> ORGANISM: Human Papillomavirus

<400> SEQUENCE: 23
taggtcgtgg tcagccatta                                                        20

<210> SEQ ID NO 24
<211> LENGTH: 20
<212> TYPE: DNA
<213> ORGANISM: Human Papillomavirus

<400> SEQUENCE: 24
tacaagcagt ccggaaagtg                                                        20

<210> SEQ ID NO 25
<211> LENGTH: 20
<212> TYPE: DNA
<213> ORGANISM: Human Papillomavirus

<400> SEQUENCE: 25
gtctaccagc gtgtcagtgg                                                        20

<210> SEQ ID NO 26
<211> LENGTH: 20
<212> TYPE: DNA
<213> ORGANISM: Human Papillomavirus

<400> SEQUENCE: 26
ggtggaagga ctggctatgt                                                        20

<210> SEQ ID NO 27
<211> LENGTH: 20
<212> TYPE: DNA
<213> ORGANISM: Human Papillomavirus

<400> SEQUENCE: 27
cggtgtatgt cctgttggaa                                                        20

<210> SEQ ID NO 28

-continued

```
<211> LENGTH: 20
<212> TYPE: DNA
<213> ORGANISM: Human Papillomavirus

<400> SEQUENCE: 28
ccttgcagcc tatacgtcct                                               20

<210> SEQ ID NO 29
<211> LENGTH: 20
<212> TYPE: DNA
<213> ORGANISM: Human Papillomavirus

<400> SEQUENCE: 29
cctcctgtgc ctgtgtctaa                                               20

<210> SEQ ID NO 30
<211> LENGTH: 20
<212> TYPE: DNA
<213> ORGANISM: Human Papillomavirus

<400> SEQUENCE: 30
cccttgcagt aacactacgc                                               20

<210> SEQ ID NO 31
<211> LENGTH: 20
<212> TYPE: DNA
<213> ORGANISM: Human Papillomavirus

<400> SEQUENCE: 31
catgtaagca atccggtacg                                               20

<210> SEQ ID NO 32
<211> LENGTH: 20
<212> TYPE: DNA
<213> ORGANISM: Human Papillomavirus

<400> SEQUENCE: 32
cagtggtcta gccttgggat                                               20

<210> SEQ ID NO 33
<211> LENGTH: 20
<212> TYPE: DNA
<213> ORGANISM: Human Papillomavirus

<400> SEQUENCE: 33
caccctgtcc tttgtgtgtc                                               20

<210> SEQ ID NO 34
<211> LENGTH: 20
<212> TYPE: DNA
<213> ORGANISM: Human Papillomavirus

<400> SEQUENCE: 34
atccagaagg tacagacggg                                               20

<210> SEQ ID NO 35
<211> LENGTH: 20
<212> TYPE: DNA
<213> ORGANISM: Human Papillomavirus

<400> SEQUENCE: 35
atccagaagg tacagacggg                                               20
```

-continued

```
<210> SEQ ID NO 36
<211> LENGTH: 20
<212> TYPE: DNA
<213> ORGANISM: Human Papillomavirus

<400> SEQUENCE: 36
agtgcttatg cagcaaatgc                                            20

<210> SEQ ID NO 37
<211> LENGTH: 20
<212> TYPE: DNA
<213> ORGANISM: Human Papillomavirus

<400> SEQUENCE: 37
aagctcggca ttggaaatac                                            20

<210> SEQ ID NO 38
<211> LENGTH: 19
<212> TYPE: DNA
<213> ORGANISM: Human Papillomavirus

<400> SEQUENCE: 38
tttcattgcc tgcacctgt                                             19

<210> SEQ ID NO 39
<211> LENGTH: 22
<212> TYPE: DNA
<213> ORGANISM: Human Papillomavirus

<400> SEQUENCE: 39
tttcagtacg aggtcttctc ca                                         22

<210> SEQ ID NO 40
<211> LENGTH: 23
<212> TYPE: DNA
<213> ORGANISM: Human Papillomavirus

<400> SEQUENCE: 40
tgtctttcat cgctactaga ggt                                        23

<210> SEQ ID NO 41
<211> LENGTH: 21
<212> TYPE: DNA
<213> ORGANISM: Human Papillomavirus

<400> SEQUENCE: 41
tgtctatagc ctccgtactg c                                          21

<210> SEQ ID NO 42
<211> LENGTH: 18
<212> TYPE: DNA
<213> ORGANISM: Human Papillomavirus

<400> SEQUENCE: 42
tggacctgtc aacccact                                              18

<210> SEQ ID NO 43
<211> LENGTH: 24
<212> TYPE: DNA
<213> ORGANISM: Human Papillomavirus

<400> SEQUENCE: 43
tattgtcact tgtaccgtct acac                                       24
```

-continued

<210> SEQ ID NO 44
<211> LENGTH: 20
<212> TYPE: DNA
<213> ORGANISM: Human Papillomavirus

<400> SEQUENCE: 44
tatgtgtccc gtcactacca                                                    20

<210> SEQ ID NO 45
<211> LENGTH: 22
<212> TYPE: DNA
<213> ORGANISM: Human Papillomavirus

<400> SEQUENCE: 45
tatggctgtt ctgaagtgga ag                                                 22

<210> SEQ ID NO 46
<211> LENGTH: 22
<212> TYPE: DNA
<213> ORGANISM: Human Papillomavirus

<400> SEQUENCE: 46
tatggctgtt ctgaagtgga ag                                                 22

<210> SEQ ID NO 47
<211> LENGTH: 24
<212> TYPE: DNA
<213> ORGANISM: Human Papillomavirus

<400> SEQUENCE: 47
tatggcaata ctgaagtgga aact                                               24

<210> SEQ ID NO 48
<211> LENGTH: 24
<212> TYPE: DNA
<213> ORGANISM: Human Papillomavirus

<400> SEQUENCE: 48
tatggcaata ctgaagtgga aact                                               24

<210> SEQ ID NO 49
<211> LENGTH: 24
<212> TYPE: DNA
<213> ORGANISM: Human Papillomavirus

<400> SEQUENCE: 49
tagaggttat actatcccca ctgc                                               24

<210> SEQ ID NO 50
<211> LENGTH: 23
<212> TYPE: DNA
<213> ORGANISM: Human Papillomavirus

<400> SEQUENCE: 50
tacgtgttct tgatgatctg caa                                                23

<210> SEQ ID NO 51
<211> LENGTH: 22
<212> TYPE: DNA
<213> ORGANISM: Human Papillomavirus

<400> SEQUENCE: 51
ggcagtattg ccagagttag ac                                                 22

-continued

```
<210> SEQ ID NO 52
<211> LENGTH: 28
<212> TYPE: DNA
<213> ORGANISM: Human Papillomavirus

<400> SEQUENCE: 52
gcagttttac aaatgaacaa tgtatgac                                        28

<210> SEQ ID NO 53
<211> LENGTH: 20
<212> TYPE: DNA
<213> ORGANISM: Human Papillomavirus

<400> SEQUENCE: 53
gcaacccacg tttcacttac                                                 20

<210> SEQ ID NO 54
<211> LENGTH: 21
<212> TYPE: DNA
<213> ORGANISM: Human Papillomavirus

<400> SEQUENCE: 54
gaccggtcga tgtatgtctt g                                               21

<210> SEQ ID NO 55
<211> LENGTH: 21
<212> TYPE: DNA
<213> ORGANISM: Human Papillomavirus

<400> SEQUENCE: 55
gacagcggtt atggcaattc t                                               21

<210> SEQ ID NO 56
<211> LENGTH: 20
<212> TYPE: DNA
<213> ORGANISM: Human Papillomavirus

<400> SEQUENCE: 56
gacagcgggt atggcaatac                                                 20

<210> SEQ ID NO 57
<211> LENGTH: 20
<212> TYPE: DNA
<213> ORGANISM: Human Papillomavirus

<400> SEQUENCE: 57
gacagcgggt atggcaatac                                                 20

<210> SEQ ID NO 58
<211> LENGTH: 22
<212> TYPE: DNA
<213> ORGANISM: Human Papillomavirus

<400> SEQUENCE: 58
ctatccccac cactactttg tg                                              22

<210> SEQ ID NO 59
<211> LENGTH: 26
<212> TYPE: DNA
<213> ORGANISM: Human Papillomavirus

<400> SEQUENCE: 59
```

```
ctacatttgt ctcacagctt acttct                                          26

<210> SEQ ID NO 60
<211> LENGTH: 21
<212> TYPE: DNA
<213> ORGANISM: Human Papillomavirus

<400> SEQUENCE: 60
cgttgtctat agcctccgta c                                               21

<210> SEQ ID NO 61
<211> LENGTH: 22
<212> TYPE: DNA
<213> ORGANISM: Human Papillomavirus

<400> SEQUENCE: 61
cgttggagtc tcatcatgtc tt                                              22

<210> SEQ ID NO 62
<211> LENGTH: 27
<212> TYPE: DNA
<213> ORGANISM: Human Papillomavirus

<400> SEQUENCE: 62
cgtcactacc attacaactt aatgttg                                         27

<210> SEQ ID NO 63
<211> LENGTH: 24
<212> TYPE: DNA
<213> ORGANISM: Human Papillomavirus

<400> SEQUENCE: 63
cccacttgat tgactactgt tact                                            24

<210> SEQ ID NO 64
<211> LENGTH: 22
<212> TYPE: DNA
<213> ORGANISM: Human Papillomavirus

<400> SEQUENCE: 64
cagatagtgg ctatggctgt tc                                              22

<210> SEQ ID NO 65
<211> LENGTH: 24
<212> TYPE: DNA
<213> ORGANISM: Human Papillomavirus

<400> SEQUENCE: 65
caccactata ctgactacat ggtg                                            24

<210> SEQ ID NO 66
<211> LENGTH: 23
<212> TYPE: DNA
<213> ORGANISM: Human Papillomavirus

<400> SEQUENCE: 66
attgctattg tcacttgtac cgt                                             23

<210> SEQ ID NO 67
<211> LENGTH: 27
<212> TYPE: DNA
<213> ORGANISM: Human Papillomavirus

<400> SEQUENCE: 67
```

-continued atggtataat aaacacgtgt gtatgtg                                          27

<210> SEQ ID NO 68
<211> LENGTH: 22
<212> TYPE: DNA
<213> ORGANISM: Human Papillomavirus

<400> SEQUENCE: 68
atcccagcaa aggatatttc gt                                               22

<210> SEQ ID NO 69
<211> LENGTH: 18
<212> TYPE: DNA
<213> ORGANISM: Human Papillomavirus

<400> SEQUENCE: 69
atcactatgc gccaacgc                                                    18

<210> SEQ ID NO 70
<211> LENGTH: 31
<212> TYPE: DNA
<213> ORGANISM: Human Papillomavirus

<400> SEQUENCE: 70
agtacattta aaatatttgt aagtggtgtt t                                     31

<210> SEQ ID NO 71
<211> LENGTH: 19
<212> TYPE: DNA
<213> ORGANISM: Human Papillomavirus

<400> SEQUENCE: 71
agctacaaaa tggccgctg                                                   19

<210> SEQ ID NO 72
<211> LENGTH: 20
<212> TYPE: DNA
<213> ORGANISM: Human Papillomavirus

<400> SEQUENCE: 72
acaggacgtt gcatagcatg                                                  20

<210> SEQ ID NO 73
<211> LENGTH: 26
<212> TYPE: DNA
<213> ORGANISM: Human Papillomavirus

<400> SEQUENCE: 73
aacattaagt tgtaatggta gtgacg                                           26

<210> SEQ ID NO 74
<211> LENGTH: 20
<212> TYPE: DNA
<213> ORGANISM: Human Papillomavirus

<400> SEQUENCE: 74
aaacctgttg taggtgggac                                                  20

<210> SEQ ID NO 75
<211> LENGTH: 24
<212> TYPE: DNA
<213> ORGANISM: Human Papillomavirus -continued

<400> SEQUENCE: 75
tttgtctcac agcttacttc tgaa                                                    24

<210> SEQ ID NO 76
<211> LENGTH: 21
<212> TYPE: DNA
<213> ORGANISM: Human Papillomavirus

<400> SEQUENCE: 76
ttacatctga actagccccc a                                                      21

<210> SEQ ID NO 77
<211> LENGTH: 25
<212> TYPE: DNA
<213> ORGANISM: Human Papillomavirus

<400> SEQUENCE: 77
tgttttaaaa cgaaagtttg cagga                                                  25

<210> SEQ ID NO 78
<211> LENGTH: 21
<212> TYPE: DNA
<213> ORGANISM: Human Papillomavirus

<400> SEQUENCE: 78
tgtattgcca tatccgctgt c                                                      21

<210> SEQ ID NO 79
<211> LENGTH: 22
<212> TYPE: DNA
<213> ORGANISM: Human Papillomavirus

<400> SEQUENCE: 79
tgtattgcca tatccactgt cc                                                     22

<210> SEQ ID NO 80
<211> LENGTH: 26
<212> TYPE: DNA
<213> ORGANISM: Human Papillomavirus

<400> SEQUENCE: 80
tgccttaaaa cgaaagtata cagaca                                                 26

<210> SEQ ID NO 81
<211> LENGTH: 16
<212> TYPE: DNA
<213> ORGANISM: Human Papillomavirus

<400> SEQUENCE: 81
tgccgccatt ttccgc                                                            16

<210> SEQ ID NO 82
<211> LENGTH: 25
<212> TYPE: DNA
<213> ORGANISM: Human Papillomavirus

<400> SEQUENCE: 82
tgcagtaaaa cgaaagttta caagc                                                  25

<210> SEQ ID NO 83
<211> LENGTH: 24
<212> TYPE: DNA
<213> ORGANISM: Human Papillomavirus -continued

<400> SEQUENCE: 83
tgcactaaaa cgaaagttta cagg                                          24

<210> SEQ ID NO 84
<211> LENGTH: 31
<212> TYPE: DNA
<213> ORGANISM: Human Papillomavirus

<400> SEQUENCE: 84
tgcaaaaact aaaacgaaag tatataggta g                                  31

<210> SEQ ID NO 85
<211> LENGTH: 29
<212> TYPE: DNA
<213> ORGANISM: Human Papillomavirus

<400> SEQUENCE: 85
tgcaaaaact aaaacgaaag tatatagct                                     29

<210> SEQ ID NO 86
<211> LENGTH: 25
<212> TYPE: DNA
<213> ORGANISM: Human Papillomavirus

<400> SEQUENCE: 86
tcttttaaaa cgaaagtttg cagga                                         25

<210> SEQ ID NO 87
<211> LENGTH: 21
<212> TYPE: DNA
<213> ORGANISM: Human Papillomavirus

<400> SEQUENCE: 87
tcagatagtg gctatggctg t                                             21

<210> SEQ ID NO 88
<211> LENGTH: 24
<212> TYPE: DNA
<213> ORGANISM: Human Papillomavirus

<400> SEQUENCE: 88
gttttaaaac gaaagtttgg gtgc                                          24

<210> SEQ ID NO 89
<211> LENGTH: 27
<212> TYPE: DNA
<213> ORGANISM: Human Papillomavirus

<400> SEQUENCE: 89
gtgttctaaa cgaaagtttt acaggta                                       27

<210> SEQ ID NO 90
<211> LENGTH: 25
<212> TYPE: DNA
<213> ORGANISM: Human Papillomavirus

<400> SEQUENCE: 90
gtgccctaaa cgaaagtat acaga                                          25

<210> SEQ ID NO 91
<211> LENGTH: 20
<212> TYPE: DNA

<213> ORGANISM: Human Papillomavirus

<400> SEQUENCE: 91
gtattgccat acccgctgtc                                                                      20

<210> SEQ ID NO 92
<211> LENGTH: 20
<212> TYPE: DNA
<213> ORGANISM: Human Papillomavirus

<400> SEQUENCE: 92
gtattgccat acccgctgtc                                                                      20

<210> SEQ ID NO 93
<211> LENGTH: 20
<212> TYPE: DNA
<213> ORGANISM: Human Papillomavirus

<400> SEQUENCE: 93
gtattgccat acccgctgtc                                                                      20

<210> SEQ ID NO 94
<211> LENGTH: 20
<212> TYPE: DNA
<213> ORGANISM: Human Papillomavirus

<400> SEQUENCE: 94
gtattgccat acccgctgtc                                                                      20

<210> SEQ ID NO 95
<211> LENGTH: 19
<212> TYPE: DNA
<213> ORGANISM: Human Papillomavirus

<400> SEQUENCE: 95
gtattgccat acccgctgt                                                                       19

<210> SEQ ID NO 96
<211> LENGTH: 20
<212> TYPE: DNA
<213> ORGANISM: Human Papillomavirus

<400> SEQUENCE: 96
gtatagccat acccgctgtc                                                                      20

<210> SEQ ID NO 97
<211> LENGTH: 25
<212> TYPE: DNA
<213> ORGANISM: Human Papillomavirus

<400> SEQUENCE: 97
ggttctaaaa cgaaagtatt tgggt                                                                25

<210> SEQ ID NO 98
<211> LENGTH: 25
<212> TYPE: DNA
<213> ORGANISM: Human Papillomavirus

<400> SEQUENCE: 98
ggtcctaaaa cgaaagtatg ctagt                                                                25

<210> SEQ ID NO 99
<211> LENGTH: 22

<212> TYPE: DNA
<213> ORGANISM: Human Papillomavirus

<400> SEQUENCE: 99
gcgcgctgcc gccattttcc gc                                              22

<210> SEQ ID NO 100
<211> LENGTH: 29
<212> TYPE: DNA
<213> ORGANISM: Human Papillomavirus

<400> SEQUENCE: 100
gcgcgcctac tatccccacc actactttg                                       29

<210> SEQ ID NO 101
<211> LENGTH: 30
<212> TYPE: DNA
<213> ORGANISM: Human Papillomavirus

<400> SEQUENCE: 101
gcgcgcaata ctgcaatgcg gatctacatt                                      30

<210> SEQ ID NO 102
<211> LENGTH: 23
<212> TYPE: DNA
<213> ORGANISM: Human Papillomavirus

<400> SEQUENCE: 102
gccttaaaac gaaagtatgg agg                                             23

<210> SEQ ID NO 103
<211> LENGTH: 25
<212> TYPE: DNA
<213> ORGANISM: Human Papillomavirus

<400> SEQUENCE: 103
gcatctaaaa cgaaagtttc taggc                                           25

<210> SEQ ID NO 104
<211> LENGTH: 22
<212> TYPE: DNA
<213> ORGANISM: Human Papillomavirus

<400> SEQUENCE: 104
gacagcggat atggcaatac tg                                              22

<210> SEQ ID NO 105
<211> LENGTH: 21
<212> TYPE: DNA
<213> ORGANISM: Human Papillomavirus

<400> SEQUENCE: 105
gaattgccat aaccgctgtc t                                               21

<210> SEQ ID NO 106
<211> LENGTH: 20
<212> TYPE: DNA
<213> ORGANISM: Human Papillomavirus

<400> SEQUENCE: 106
gaatagccat agccgctgtc                                                 20

<210> SEQ ID NO 107

-continued

```
<211> LENGTH: 22
<212> TYPE: DNA
<213> ORGANISM: Human Papillomavirus

<400> SEQUENCE: 107
gaacagccat agccactatc tg                                             22

<210> SEQ ID NO 108
<211> LENGTH: 20
<212> TYPE: DNA
<213> ORGANISM: Human Papillomavirus

<400> SEQUENCE: 108
ctattgccat agccgctgtc                                                20

<210> SEQ ID NO 109
<211> LENGTH: 23
<212> TYPE: DNA
<213> ORGANISM: Human Papillomavirus

<400> SEQUENCE: 109
ctactatccc caccactact ttg                                            23

<210> SEQ ID NO 110
<211> LENGTH: 27
<212> TYPE: DNA
<213> ORGANISM: Human Papillomavirus

<400> SEQUENCE: 110
cgcaatttaa aacgaaagtt actaggt                                        27

<210> SEQ ID NO 111
<211> LENGTH: 20
<212> TYPE: DNA
<213> ORGANISM: Human Papillomavirus

<400> SEQUENCE: 111
cccactagac tccgagtcat                                                20

<210> SEQ ID NO 112
<211> LENGTH: 22
<212> TYPE: DNA
<213> ORGANISM: Human Papillomavirus

<400> SEQUENCE: 112
cccaccccac tagattctaa gt                                             22

<210> SEQ ID NO 113
<211> LENGTH: 28
<212> TYPE: DNA
<213> ORGANISM: Human Papillomavirus

<400> SEQUENCE: 113
catcagttaa aacgaaagtt tctagtca                                       28

<210> SEQ ID NO 114
<211> LENGTH: 22
<212> TYPE: DNA
<213> ORGANISM: Human Papillomavirus

<400> SEQUENCE: 114
catattgcca tatccgctgt ct                                             22
```

-continued

```
<210> SEQ ID NO 115
<211> LENGTH: 22
<212> TYPE: DNA
<213> ORGANISM: Human Papillomavirus

<400> SEQUENCE: 115
cagaacagcc atagccacta tc                                           22

<210> SEQ ID NO 116
<211> LENGTH: 29
<212> TYPE: DNA
<213> ORGANISM: Human Papillomavirus

<400> SEQUENCE: 116
cagaaattaa aacgaaagta tttaggcag                                    29

<210> SEQ ID NO 117
<211> LENGTH: 23
<212> TYPE: DNA
<213> ORGANISM: Human Papillomavirus

<400> SEQUENCE: 117
cactaaaacg aaagtttgca gca                                          23

<210> SEQ ID NO 118
<211> LENGTH: 20
<212> TYPE: DNA
<213> ORGANISM: Human Papillomavirus

<400> SEQUENCE: 118
atattgccat agccgctgtc                                              20

<210> SEQ ID NO 119
<211> LENGTH: 20
<212> TYPE: DNA
<213> ORGANISM: Human Papillomavirus

<400> SEQUENCE: 119
atattgccat agccgctgtc                                              20

<210> SEQ ID NO 120
<211> LENGTH: 21
<212> TYPE: DNA
<213> ORGANISM: Human Papillomavirus

<400> SEQUENCE: 120
agtattgcca tatccgctgt c                                            21

<210> SEQ ID NO 121
<211> LENGTH: 21
<212> TYPE: DNA
<213> ORGANISM: Human Papillomavirus

<400> SEQUENCE: 121
agtattgcca tatccgctgt c                                            21

<210> SEQ ID NO 122
<211> LENGTH: 21
<212> TYPE: DNA
<213> ORGANISM: Human Papillomavirus

<400> SEQUENCE: 122
agtattgcca tatccgctgt c                                            21
```

-continued

```
<210> SEQ ID NO 123
<211> LENGTH: 22
<212> TYPE: DNA
<213> ORGANISM: Human Papillomavirus

<400> SEQUENCE: 123
agtattgcca tatccactgt cc                                              22

<210> SEQ ID NO 124
<211> LENGTH: 26
<212> TYPE: DNA
<213> ORGANISM: Human Papillomavirus

<400> SEQUENCE: 124
aggttctaaa acgaaagtat gtaggt                                          26

<210> SEQ ID NO 125
<211> LENGTH: 21
<212> TYPE: DNA
<213> ORGANISM: Human Papillomavirus

<400> SEQUENCE: 125
actaaaacga aagtttgccg c                                               21

<210> SEQ ID NO 126
<211> LENGTH: 23
<212> TYPE: DNA
<213> ORGANISM: Human Papillomavirus

<400> SEQUENCE: 126
acagcttact tctgaatcat ccc                                             23

<210> SEQ ID NO 127
<211> LENGTH: 24
<212> TYPE: DNA
<213> ORGANISM: Human Papillomavirus

<400> SEQUENCE: 127
aatactgcaa tgcggatcta catt                                            24

<210> SEQ ID NO 128
<211> LENGTH: 23
<212> TYPE: DNA
<213> ORGANISM: Human Papillomavirus

<400> SEQUENCE: 128
tctgctacac acactatgtt gtg                                             23

<210> SEQ ID NO 129
<211> LENGTH: 19
<212> TYPE: DNA
<213> ORGANISM: Human Papillomavirus

<400> SEQUENCE: 129
tcccgtatac tgtcgccat                                                  19

<210> SEQ ID NO 130
<211> LENGTH: 22
<212> TYPE: DNA
<213> ORGANISM: Human Papillomavirus

<400> SEQUENCE: 130
tagcactatc cacactactg ca                                              22
```

-continued

```
<210> SEQ ID NO 131
<211> LENGTH: 18
<212> TYPE: DNA
<213> ORGANISM: Human Papillomavirus

<400> SEQUENCE: 131
gtacactgcc gccatgtt                                            18

<210> SEQ ID NO 132
<211> LENGTH: 22
<212> TYPE: DNA
<213> ORGANISM: Human Papillomavirus

<400> SEQUENCE: 132
gctactacac acactgttct gt                                       22

<210> SEQ ID NO 133
<211> LENGTH: 19
<212> TYPE: DNA
<213> ORGANISM: Human Papillomavirus

<400> SEQUENCE: 133
gcgagcctcc attttgtga                                           19

<210> SEQ ID NO 134
<211> LENGTH: 20
<212> TYPE: DNA
<213> ORGANISM: Human Papillomavirus

<400> SEQUENCE: 134
gacagcgggt atggcaatac                                          20

<210> SEQ ID NO 135
<211> LENGTH: 20
<212> TYPE: DNA
<213> ORGANISM: Human Papillomavirus

<400> SEQUENCE: 135
gacagcggct atggcaatat                                          20

<210> SEQ ID NO 136
<211> LENGTH: 21
<212> TYPE: DNA
<213> ORGANISM: Human Papillomavirus

<400> SEQUENCE: 136
cctatgctcc catctctgct a                                        21

<210> SEQ ID NO 137
<211> LENGTH: 28
<212> TYPE: DNA
<213> ORGANISM: Human Papillomavirus

<400> SEQUENCE: 137
ccatatgtat tacagagtcc tcactatt                                 28

<210> SEQ ID NO 138
<211> LENGTH: 27
<212> TYPE: DNA
<213> ORGANISM: Human Papillomavirus

<400> SEQUENCE: 138
```

-continued

```
ccatatgtat tacagagtcc tcactat                                27

<210> SEQ ID NO 139
<211> LENGTH: 23
<212> TYPE: DNA
<213> ORGANISM: Human Papillomavirus

<400> SEQUENCE: 139
ccatatcact tcctgaccct atg                                    23

<210> SEQ ID NO 140
<211> LENGTH: 21
<212> TYPE: DNA
<213> ORGANISM: Human Papillomavirus

<400> SEQUENCE: 140
catgttactg ctgtcgctac a                                      21

<210> SEQ ID NO 141
<211> LENGTH: 23
<212> TYPE: DNA
<213> ORGANISM: Human Papillomavirus

<400> SEQUENCE: 141
cagtctattt gactgtcgct aca                                    23

<210> SEQ ID NO 142
<211> LENGTH: 20
<212> TYPE: DNA
<213> ORGANISM: Human Papillomavirus

<400> SEQUENCE: 142
cagcgggtat ggcaatacat                                        20

<210> SEQ ID NO 143
<211> LENGTH: 22
<212> TYPE: DNA
<213> ORGANISM: Human Papillomavirus

<400> SEQUENCE: 143
cagacagcgg atatggcaat at                                     22

<210> SEQ ID NO 144
<211> LENGTH: 21
<212> TYPE: DNA
<213> ORGANISM: Human Papillomavirus

<400> SEQUENCE: 144
attagtgggg gatgttggaa c                                      21

<210> SEQ ID NO 145
<211> LENGTH: 24
<212> TYPE: DNA
<213> ORGANISM: Human Papillomavirus

<400> SEQUENCE: 145
atccatattt gataccgagt gctc                                   24

<210> SEQ ID NO 146
<211> LENGTH: 25
<212> TYPE: DNA
<213> ORGANISM: Human Papillomavirus

<400> SEQUENCE: 146
```

-continued

```
atatttgata ccgagtgctc actac                              25

<210> SEQ ID NO 147
<211> LENGTH: 20
<212> TYPE: DNA
<213> ORGANISM: Human Papillomavirus

<400> SEQUENCE: 147
agtcctcccg tatactgtcg                                    20

<210> SEQ ID NO 148
<211> LENGTH: 19
<212> TYPE: DNA
<213> ORGANISM: Human Papillomavirus

<400> SEQUENCE: 148
agacagcggc tatggctat                                     19

<210> SEQ ID NO 149
<211> LENGTH: 21
<212> TYPE: DNA
<213> ORGANISM: Human Papillomavirus

<400> SEQUENCE: 149
actgttttgt gagcctccat t                                  21

<210> SEQ ID NO 150
<211> LENGTH: 18
<212> TYPE: DNA
<213> ORGANISM: Human Papillomavirus

<400> SEQUENCE: 150
tggtccagat tagatttg                                      18

<210> SEQ ID NO 151
<211> LENGTH: 19
<212> TYPE: DNA
<213> ORGANISM: Human Papillomavirus

<400> SEQUENCE: 151
tgagaaatgc attagatgg                                     19

<210> SEQ ID NO 152
<211> LENGTH: 21
<212> TYPE: DNA
<213> ORGANISM: Human Papillomavirus

<400> SEQUENCE: 152
ggaaatcctt tttctcaagg a                                  21

<210> SEQ ID NO 153
<211> LENGTH: 19
<212> TYPE: DNA
<213> ORGANISM: Human Papillomavirus

<400> SEQUENCE: 153
gccaggagaa aatactaga                                     19

<210> SEQ ID NO 154
<211> LENGTH: 15
<212> TYPE: DNA
<213> ORGANISM: Human Papillomavirus
```

-continued

```
<400> SEQUENCE: 154
ccaccaggtg gtgcc                                                     15

<210> SEQ ID NO 155
<211> LENGTH: 20
<212> TYPE: DNA
<213> ORGANISM: Human Papillomavirus

<400> SEQUENCE: 155
cagtgggcat ttgataatga                                               20

<210> SEQ ID NO 156
<211> LENGTH: 22
<212> TYPE: DNA
<213> ORGANISM: Human Papillomavirus

<400> SEQUENCE: 156
cagcaatgtc aaatattagt ga                                            22

<210> SEQ ID NO 157
<211> LENGTH: 22
<212> TYPE: DNA
<213> ORGANISM: Human Papillomavirus

<400> SEQUENCE: 157
aagctattga actgcagatg gc                                            22

<210> SEQ ID NO 158
<211> LENGTH: 19
<212> TYPE: DNA
<213> ORGANISM: Human Papillomavirus

<400> SEQUENCE: 158
tctagtattt tctcctggc                                                19

<210> SEQ ID NO 159
<211> LENGTH: 21
<212> TYPE: DNA
<213> ORGANISM: Human Papillomavirus

<400> SEQUENCE: 159
tccttgagaa aaaggatttc c                                             21

<210> SEQ ID NO 160
<211> LENGTH: 20
<212> TYPE: DNA
<213> ORGANISM: Human Papillomavirus

<400> SEQUENCE: 160
tcattatcaa atgcccactg                                               20

<210> SEQ ID NO 161
<211> LENGTH: 15
<212> TYPE: DNA
<213> ORGANISM: Human Papillomavirus

<400> SEQUENCE: 161
ggcaccacct ggtgg                                                    15

<210> SEQ ID NO 162
<211> LENGTH: 22
<212> TYPE: DNA
<213> ORGANISM: Human Papillomavirus
```

-continued

<400> SEQUENCE: 162
gccatctgca gttcaatagc tt                                              22

<210> SEQ ID NO 163
<211> LENGTH: 19
<212> TYPE: DNA
<213> ORGANISM: Human Papillomavirus

<400> SEQUENCE: 163
ccatctaatg catttctca                                                 19

<210> SEQ ID NO 164
<211> LENGTH: 18
<212> TYPE: DNA
<213> ORGANISM: Human Papillomavirus

<400> SEQUENCE: 164
tgtttcttcc caggctgc                                                  18

<210> SEQ ID NO 165
<211> LENGTH: 23
<212> TYPE: DNA
<213> ORGANISM: Human Papillomavirus

<400> SEQUENCE: 165
tggttgcaat atatatgcgt agc                                             23

<210> SEQ ID NO 166
<211> LENGTH: 20
<212> TYPE: DNA
<213> ORGANISM: Human Papillomavirus

<400> SEQUENCE: 166
tctgatgagg ggtcaaaagt                                                20

<210> SEQ ID NO 167
<211> LENGTH: 20
<212> TYPE: DNA
<213> ORGANISM: Human Papillomavirus

<400> SEQUENCE: 167
tcattatcaa atgcccactg                                                20

<210> SEQ ID NO 168
<211> LENGTH: 23
<212> TYPE: DNA
<213> ORGANISM: Human Papillomavirus

<400> SEQUENCE: 168
tcatgataaa aatgtacacg ggc                                             23

<210> SEQ ID NO 169
<211> LENGTH: 21
<212> TYPE: DNA
<213> ORGANISM: Human Papillomavirus

<400> SEQUENCE: 169
taaatgcagt gttggcagta c                                               21

<210> SEQ ID NO 170
<211> LENGTH: 19
<212> TYPE: DNA

-continued

<213> ORGANISM: Human Papillomavirus

<400> SEQUENCE: 170
gtttcttccc aggctgcta                                          19

<210> SEQ ID NO 171
<211> LENGTH: 19
<212> TYPE: DNA
<213> ORGANISM: Human Papillomavirus

<400> SEQUENCE: 171
gttcgtttgc ataggcctg                                          19

<210> SEQ ID NO 172
<211> LENGTH: 19
<212> TYPE: DNA
<213> ORGANISM: Human Papillomavirus

<400> SEQUENCE: 172
gttcgtttgc ataggcctg                                          19

<210> SEQ ID NO 173
<211> LENGTH: 19
<212> TYPE: DNA
<213> ORGANISM: Human Papillomavirus

<400> SEQUENCE: 173
gtcctttagc aaagtcgcc                                          19

<210> SEQ ID NO 174
<211> LENGTH: 24
<212> TYPE: DNA
<213> ORGANISM: Human Papillomavirus

<400> SEQUENCE: 174
gtatgattca ggtatgtaca ctgc                                    24

<210> SEQ ID NO 175
<211> LENGTH: 24
<212> TYPE: DNA
<213> ORGANISM: Human Papillomavirus

<400> SEQUENCE: 175
gtagaatacg aaaagggaaa tggg                                    24

<210> SEQ ID NO 176
<211> LENGTH: 18
<212> TYPE: DNA
<213> ORGANISM: Human Papillomavirus

<400> SEQUENCE: 176
gcgacacaga caataccg                                           18

<210> SEQ ID NO 177
<211> LENGTH: 16
<212> TYPE: DNA
<213> ORGANISM: Human Papillomavirus

<400> SEQUENCE: 177
gccactgcag ctacca                                             16

<210> SEQ ID NO 178
<211> LENGTH: 24

```
<212> TYPE: DNA
<213> ORGANISM: Human Papillomavirus

<400> SEQUENCE: 178
gcaagacaga tacttggctt atac                                      24

<210> SEQ ID NO 179
<211> LENGTH: 25
<212> TYPE: DNA
<213> ORGANISM: Human Papillomavirus

<400> SEQUENCE: 179
gactttatgg atatagttcg tttgc                                     25

<210> SEQ ID NO 180
<211> LENGTH: 20
<212> TYPE: DNA
<213> ORGANISM: Human Papillomavirus

<400> SEQUENCE: 180
gacagcgggt atggcaatac                                           20

<210> SEQ ID NO 181
<211> LENGTH: 22
<212> TYPE: DNA
<213> ORGANISM: Human Papillomavirus

<400> SEQUENCE: 181
gacagcggat atggcaatac tg                                         22

<210> SEQ ID NO 182
<211> LENGTH: 18
<212> TYPE: DNA
<213> ORGANISM: Human Papillomavirus

<400> SEQUENCE: 182
cgggtgtcta acgctgac                                             18

<210> SEQ ID NO 183
<211> LENGTH: 17
<212> TYPE: DNA
<213> ORGANISM: Human Papillomavirus

<400> SEQUENCE: 183
cggcactgta tacgccg                                              17

<210> SEQ ID NO 184
<211> LENGTH: 22
<212> TYPE: DNA
<213> ORGANISM: Human Papillomavirus

<400> SEQUENCE: 184
cgagtgctca ctacaattac tg                                         22

<210> SEQ ID NO 185
<211> LENGTH: 21
<212> TYPE: DNA
<213> ORGANISM: Human Papillomavirus

<400> SEQUENCE: 185
ccgaccgtgt taatgacaaa c                                          21

<210> SEQ ID NO 186
```

```
<211> LENGTH: 18
<212> TYPE: DNA
<213> ORGANISM: Human Papillomavirus

<400> SEQUENCE: 186 ccatttgta tggccggg                                                    18

<210> SEQ ID NO 187
<211> LENGTH: 20
<212> TYPE: DNA
<213> ORGANISM: Human Papillomavirus

<400> SEQUENCE: 187
ccactacggg taaacatggt                                                 20

<210> SEQ ID NO 188
<211> LENGTH: 15
<212> TYPE: DNA
<213> ORGANISM: Human Papillomavirus

<400> SEQUENCE: 188
ccaccaggtg gtgcc                                                      15

<210> SEQ ID NO 189
<211> LENGTH: 22
<212> TYPE: DNA
<213> ORGANISM: Human Papillomavirus

<400> SEQUENCE: 189
cagcaatgtc aaatattagt ga                                              22

<210> SEQ ID NO 190
<211> LENGTH: 21
<212> TYPE: DNA
<213> ORGANISM: Human Papillomavirus

<400> SEQUENCE: 190
cagacccgga ctttatggat a                                               21

<210> SEQ ID NO 191
<211> LENGTH: 23
<212> TYPE: DNA
<213> ORGANISM: Human Papillomavirus

<400> SEQUENCE: 191
caatttgttt accactacgg gta                                             23

<210> SEQ ID NO 192
<211> LENGTH: 22
<212> TYPE: DNA
<213> ORGANISM: Human Papillomavirus

<400> SEQUENCE: 192
caatttgttt accactacgg gt                                              22

<210> SEQ ID NO 193
<211> LENGTH: 18
<212> TYPE: DNA
<213> ORGANISM: Human Papillomavirus

<400> SEQUENCE: 193
caacaacaca ctaccgcc                                                   18
```

-continued

```
<210> SEQ ID NO 194
<211> LENGTH: 22
<212> TYPE: DNA
<213> ORGANISM: Human Papillomavirus

<400> SEQUENCE: 194
atagagaact gctgtgttca gc                                              22

<210> SEQ ID NO 195
<211> LENGTH: 25
<212> TYPE: DNA
<213> ORGANISM: Human Papillomavirus

<400> SEQUENCE: 195
agtatcttgt ttaaaaaag ggagt                                           25

<210> SEQ ID NO 196
<211> LENGTH: 19
<212> TYPE: DNA
<213> ORGANISM: Human Papillomavirus

<400> SEQUENCE: 196
agacagaaac tgtgactgc                                                 19

<210> SEQ ID NO 197
<211> LENGTH: 19
<212> TYPE: DNA
<213> ORGANISM: Human Papillomavirus

<400> SEQUENCE: 197
actaggtcaa agcctgctg                                                 19

<210> SEQ ID NO 198
<211> LENGTH: 24
<212> TYPE: DNA
<213> ORGANISM: Human Papillomavirus

<400> SEQUENCE: 198
acacagacaa acaacataca aaac                                           24

<210> SEQ ID NO 199
<211> LENGTH: 23
<212> TYPE: DNA
<213> ORGANISM: Human Papillomavirus

<400> SEQUENCE: 199
thhtcaaatg cccartgrac cat                                            23

<210> SEQ ID NO 200
<211> LENGTH: 24
<212> TYPE: DNA
<213> ORGANISM: Human Papillomavirus

<400> SEQUENCE: 200
gttttatcac ttttaaaatt tcta                                           24

<210> SEQ ID NO 201
<211> LENGTH: 21
<212> TYPE: DNA
<213> ORGANISM: Human Papillomavirus

<400> SEQUENCE: 201
gtttataatg tctacacatt g                                              21
```

```
<210> SEQ ID NO 202
<211> LENGTH: 16
<212> TYPE: DNA
<213> ORGANISM: Human Papillomavirus
<220> FEATURE:
<221> NAME/KEY: 202
<222> LOCATION: (10)..(10)
<223> OTHER INFORMATION: n is one of the following nucleotides: a or g
      or c or t
<220> FEATURE:
<221> NAME/KEY: misc_feature
<222> LOCATION: (10)..(10)
<223> OTHER INFORMATION: n is a, c, g, or t

<400> SEQUENCE: 202
ggacagcggn tatggc                                                    16

<210> SEQ ID NO 203
<211> LENGTH: 25
<212> TYPE: DNA
<213> ORGANISM: Human Papillomavirus

<400> SEQUENCE: 203
cttgttttat cacttttaaa tggtc                                          25

<210> SEQ ID NO 204
<211> LENGTH: 16
<212> TYPE: DNA
<213> ORGANISM: Human Papillomavirus
<220> FEATURE:
<221> NAME/KEY: 204
<222> LOCATION: (10)..(10)
<223> OTHER INFORMATION: n is one of the following nucleotides: a or g
      or c or t
<220> FEATURE:
<221> NAME/KEY: misc_feature
<222> LOCATION: (10)..(10)
<223> OTHER INFORMATION: n is a, c, g, or t

<400> SEQUENCE: 204
agatagtggn tatggc                                                    16

<210> SEQ ID NO 205
<211> LENGTH: 16
<212> TYPE: DNA
<213> ORGANISM: Human Papillomavirus
<220> FEATURE:
<221> NAME/KEY: 205
<222> LOCATION: (10)..(10)
<223> OTHER INFORMATION: n is one of the following nucleotides: a or g
      or c or t
<220> FEATURE:
<221> NAME/KEY: misc_feature
<222> LOCATION: (10)..(10)
<223> OTHER INFORMATION: n is a, c, g, or t

<400> SEQUENCE: 205
agacagcggn tatggc                                                    16

<210> SEQ ID NO 206
<211> LENGTH: 27
<212> TYPE: DNA
<213> ORGANISM: Human Papillomavirus

<400> SEQUENCE: 206
ttaaaaacag tacagacaca tggtgta                                        27

<210> SEQ ID NO 207
```

-continued

```
<211> LENGTH: 19
<212> TYPE: DNA
<213> ORGANISM: Human Papillomavirus

<400> SEQUENCE: 207
tgtttcttcc caggctgct                                                19

<210> SEQ ID NO 208
<211> LENGTH: 21
<212> TYPE: DNA
<213> ORGANISM: Human Papillomavirus

<400> SEQUENCE: 208
tcctcatcct ctgagctgtt c                                             21

<210> SEQ ID NO 209
<211> LENGTH: 23
<212> TYPE: DNA
<213> ORGANISM: Human Papillomavirus

<400> SEQUENCE: 209
tcccattttc cactagtccc ata                                           23

<210> SEQ ID NO 210
<211> LENGTH: 16
<212> TYPE: DNA
<213> ORGANISM: Human Papillomavirus

<400> SEQUENCE: 210
tatgggtcgc ggtggt                                                   16

<210> SEQ ID NO 211
<211> LENGTH: 24
<212> TYPE: DNA
<213> ORGANISM: Human Papillomavirus

<400> SEQUENCE: 211
taaatgcagt gttggcagta ctag                                          24

<210> SEQ ID NO 212
<211> LENGTH: 21
<212> TYPE: DNA
<213> ORGANISM: Human Papillomavirus

<400> SEQUENCE: 212
gtgggtccag tagcatttca a                                             21

<210> SEQ ID NO 213
<211> LENGTH: 17
<212> TYPE: DNA
<213> ORGANISM: Human Papillomavirus

<400> SEQUENCE: 213
gtcgcggtgg tgttctg                                                  17

<210> SEQ ID NO 214
<211> LENGTH: 19
<212> TYPE: DNA
<213> ORGANISM: Human Papillomavirus

<400> SEQUENCE: 214
gcaaccaaat tgtgtcgcc                                                19
```

-continued

```
<210> SEQ ID NO 215
<211> LENGTH: 19
<212> TYPE: DNA
<213> ORGANISM: Human Papillomavirus

<400> SEQUENCE: 215
gaaacagtgg aagcaacgc                                               19

<210> SEQ ID NO 216
<211> LENGTH: 21
<212> TYPE: DNA
<213> ORGANISM: Human Papillomavirus

<400> SEQUENCE: 216
ctctacctgc accattgtct c                                            21

<210> SEQ ID NO 217
<211> LENGTH: 24
<212> TYPE: DNA
<213> ORGANISM: Human Papillomavirus

<400> SEQUENCE: 217
cgcagaccca ggtataatat ttga                                         24

<210> SEQ ID NO 218
<211> LENGTH: 20
<212> TYPE: DNA
<213> ORGANISM: Human Papillomavirus

<400> SEQUENCE: 218
cctcatcctc tgagctgttc                                              20

<210> SEQ ID NO 219
<211> LENGTH: 23
<212> TYPE: DNA
<213> ORGANISM: Human Papillomavirus

<400> SEQUENCE: 219
caggacagtg gatatggcaa tac                                          23

<210> SEQ ID NO 220
<211> LENGTH: 20
<212> TYPE: DNA
<213> ORGANISM: Human Papillomavirus

<400> SEQUENCE: 220
cagcgggtat ggcaatacat                                              20

<210> SEQ ID NO 221
<211> LENGTH: 21
<212> TYPE: DNA
<213> ORGANISM: Human Papillomavirus

<400> SEQUENCE: 221
cacaacagca actgaatcag c                                            21

<210> SEQ ID NO 222
<211> LENGTH: 21
<212> TYPE: DNA
<213> ORGANISM: Human Papillomavirus

<400> SEQUENCE: 222
caacagcaac tgaatcagca g                                            21
```

-continued

```
<210> SEQ ID NO 223
<211> LENGTH: 23
<212> TYPE: DNA
<213> ORGANISM: Human Papillomavirus

<400> SEQUENCE: 223
atgaagaagg caaccaaatt gtg                                              23

<210> SEQ ID NO 224
<211> LENGTH: 24
<212> TYPE: DNA
<213> ORGANISM: Human Papillomavirus

<400> SEQUENCE: 224
atctctgcta cacacactat gttg                                            24

<210> SEQ ID NO 225
<211> LENGTH: 25
<212> TYPE: DNA
<213> ORGANISM: Human Papillomavirus

<400> SEQUENCE: 225
atatttgata ccgagtgctc actac                                           25

<210> SEQ ID NO 226
<211> LENGTH: 20
<212> TYPE: DNA
<213> ORGANISM: Human Papillomavirus

<400> SEQUENCE: 226
actaggtcaa agcctgctgt                                                 20

<210> SEQ ID NO 227
<211> LENGTH: 21
<212> TYPE: DNA
<213> ORGANISM: Human Papillomavirus

<400> SEQUENCE: 227
acagcggata tggcaataca c                                               21

<210> SEQ ID NO 228
<211> LENGTH: 21
<212> TYPE: DNA
<213> ORGANISM: Human Papillomavirus

<400> SEQUENCE: 228
acagcggata tggcaataca c                                               21

<210> SEQ ID NO 229
<211> LENGTH: 20
<212> TYPE: DNA
<213> ORGANISM: Human Papillomavirus

<400> SEQUENCE: 229
tcawatgccc aytgyaycat                                                 20

<210> SEQ ID NO 230
<211> LENGTH: 19
<212> TYPE: DNA
<213> ORGANISM: Human Papillomavirus

<400> SEQUENCE: 230
gtcatatgcc cattgtacc                                                  19
```

-continued

```
<210> SEQ ID NO 231
<211> LENGTH: 19
<212> TYPE: DNA
<213> ORGANISM: Human Papillomavirus

<400> SEQUENCE: 231
gtcatatgcc cattgcacc                                              19

<210> SEQ ID NO 232
<211> LENGTH: 19
<212> TYPE: DNA
<213> ORGANISM: Human Papillomavirus

<400> SEQUENCE: 232
gtcaaatgcc cattgtacc                                              19

<210> SEQ ID NO 233
<211> LENGTH: 19
<212> TYPE: DNA
<213> ORGANISM: Human Papillomavirus

<400> SEQUENCE: 233
gtcaaatgcc cattgcacc                                              19

<210> SEQ ID NO 234
<211> LENGTH: 19
<212> TYPE: DNA
<213> ORGANISM: Human Papillomavirus

<400> SEQUENCE: 234
gtcaaatgcc cactgcacc                                              19

<210> SEQ ID NO 235
<211> LENGTH: 19
<212> TYPE: DNA
<213> ORGANISM: Human Papillomavirus

<400> SEQUENCE: 235
ggacagtgga tatggcaat                                              19

<210> SEQ ID NO 236
<211> LENGTH: 19
<212> TYPE: DNA
<213> ORGANISM: Human Papillomavirus

<400> SEQUENCE: 236
ggacagcggg tatggctat                                              19

<210> SEQ ID NO 237
<211> LENGTH: 19
<212> TYPE: DNA
<213> ORGANISM: Human Papillomavirus

<400> SEQUENCE: 237
ggacagcggg tatggcaat                                              19

<210> SEQ ID NO 238
<211> LENGTH: 19
<212> TYPE: DNA
<213> ORGANISM: Human Papillomavirus

<400> SEQUENCE: 238
```
ggacagcggc tatggcaat                                                                  19

<210> SEQ ID NO 239
<211> LENGTH: 19
<212> TYPE: DNA
<213> ORGANISM: Human Papillomavirus

<400> SEQUENCE: 239
ggacagcgga tatggcaat                                                                  19

<210> SEQ ID NO 240
<211> LENGTH: 18
<212> TYPE: DNA
<213> ORGANISM: Human Papillomavirus
<220> FEATURE:
<221> NAME/KEY: 240
<222> LOCATION: (9)..(9)
<223> OTHER INFORMATION: n is one of the following nucleotides: a or g
      or c or t
<220> FEATURE:
<221> NAME/KEY: misc_feature
<222> LOCATION: (9)..(9)
<223> OTHER INFORMATION: n is a, c, g, or t

<400> SEQUENCE: 240
gacagyggnt atggcwat                                                                   18

<210> SEQ ID NO 241
<211> LENGTH: 18
<212> TYPE: DNA
<213> ORGANISM: Human Papillomavirus
<220> FEATURE:
<221> NAME/KEY: 241
<222> LOCATION: (9)..(9)
<223> OTHER INFORMATION: n is one of the following nucleotides: a or g
      or c or t
<220> FEATURE:
<221> NAME/KEY: misc_feature
<222> LOCATION: (9)..(9)
<223> OTHER INFORMATION: n is a, c, g, or t

<400> SEQUENCE: 241
gacagyggnt atggcwat                                                                   18

<210> SEQ ID NO 242
<211> LENGTH: 19
<212> TYPE: DNA
<213> ORGANISM: Human Papillomavirus

<400> SEQUENCE: 242
atcgtaggcc cattgtacc                                                                  19

<210> SEQ ID NO 243
<211> LENGTH: 19
<212> TYPE: DNA
<213> ORGANISM: Human Papillomavirus

<400> SEQUENCE: 243
atcgaacgcc cattgcacc                                                                  19

<210> SEQ ID NO 244
<211> LENGTH: 19
<212> TYPE: DNA
<213> ORGANISM: Human Papillomavirus

<400> SEQUENCE: 244
atcatatgcc cattgtatc                                                                  19

-continued

```
<210> SEQ ID NO 245
<211> LENGTH: 19
<212> TYPE: DNA
<213> ORGANISM: Human Papillomavirus

<400> SEQUENCE: 245
atcatatgcc cattgcacc                                              19

<210> SEQ ID NO 246
<211> LENGTH: 19
<212> TYPE: DNA
<213> ORGANISM: Human Papillomavirus

<400> SEQUENCE: 246
atcatatgcc cactgtacc                                              19

<210> SEQ ID NO 247
<211> LENGTH: 19
<212> TYPE: DNA
<213> ORGANISM: Human Papillomavirus

<400> SEQUENCE: 247
atcaaatgcc cattgtacc                                              19

<210> SEQ ID NO 248
<211> LENGTH: 19
<212> TYPE: DNA
<213> ORGANISM: Human Papillomavirus

<400> SEQUENCE: 248
atcaaatgcc cattgcacc                                              19

<210> SEQ ID NO 249
<211> LENGTH: 19
<212> TYPE: DNA
<213> ORGANISM: Human Papillomavirus

<400> SEQUENCE: 249
atcaaatgcc cactgtatc                                              19

<210> SEQ ID NO 250
<211> LENGTH: 19
<212> TYPE: DNA
<213> ORGANISM: Human Papillomavirus

<400> SEQUENCE: 250
atcaaatgcc cactgtacc                                              19

<210> SEQ ID NO 251
<211> LENGTH: 19
<212> TYPE: DNA
<213> ORGANISM: Human Papillomavirus

<400> SEQUENCE: 251
atcaaatgcc cactgcacc                                              19

<210> SEQ ID NO 252
<211> LENGTH: 19
<212> TYPE: DNA
<213> ORGANISM: Human Papillomavirus

<400> SEQUENCE: 252
```

-continued

```
atcaaacgcc cattgtatc                                          19

<210> SEQ ID NO 253
<211> LENGTH: 20
<212> TYPE: DNA
<213> ORGANISM: Human Papillomavirus

<400> SEQUENCE: 253
agatagtggc tatggctgtt                                         20

<210> SEQ ID NO 254
<211> LENGTH: 20
<212> TYPE: DNA
<213> ORGANISM: Human Papillomavirus

<400> SEQUENCE: 254
agatagtggc tatggctgtt                                         20

<210> SEQ ID NO 255
<211> LENGTH: 19
<212> TYPE: DNA
<213> ORGANISM: Human Papillomavirus

<400> SEQUENCE: 255
agacagcggt tatggcaat                                          19

<210> SEQ ID NO 256
<211> LENGTH: 19
<212> TYPE: DNA
<213> ORGANISM: Human Papillomavirus

<400> SEQUENCE: 256
agacagcggg tatggcaat                                          19

<210> SEQ ID NO 257
<211> LENGTH: 17
<212> TYPE: DNA
<213> ORGANISM: Human Papillomavirus

<400> SEQUENCE: 257
agacagcggg tatggca                                            17

<210> SEQ ID NO 258
<211> LENGTH: 19
<212> TYPE: DNA
<213> ORGANISM: Human Papillomavirus

<400> SEQUENCE: 258
agacagcggc tatggctat                                          19

<210> SEQ ID NO 259
<211> LENGTH: 19
<212> TYPE: DNA
<213> ORGANISM: Human Papillomavirus

<400> SEQUENCE: 259
agacagcggc tatggcaat                                          19

<210> SEQ ID NO 260
<211> LENGTH: 19
<212> TYPE: DNA
<213> ORGANISM: Human Papillomavirus

<400> SEQUENCE: 260
```

-continued

```
agacagcgga tatggcaat                                               19

<210> SEQ ID NO 261
<211> LENGTH: 22
<212> TYPE: DNA
<213> ORGANISM: Human Papillomavirus

<400> SEQUENCE: 261
cacagctttc tgttgtttcc ac                                           22

<210> SEQ ID NO 262
<211> LENGTH: 22
<212> TYPE: DNA
<213> ORGANISM: Human Papillomavirus

<400> SEQUENCE: 262
tccagtattc tccacggtta cc                                           22

<210> SEQ ID NO 263
<211> LENGTH: 21
<212> TYPE: DNA
<213> ORGANISM: Human Papillomavirus

<400> SEQUENCE: 263
ggtactgttt tgtgagcctc c                                            21

<210> SEQ ID NO 264
<211> LENGTH: 18
<212> TYPE: DNA
<213> ORGANISM: Human Papillomavirus

<400> SEQUENCE: 264
cagacagcgg ctatggct                                                18

<210> SEQ ID NO 265
<211> LENGTH: 18
<212> TYPE: DNA
<213> ORGANISM: Human Papillomavirus

<400> SEQUENCE: 265
caagacagcg ggtatggc                                                18

<210> SEQ ID NO 266
<211> LENGTH: 23
<212> TYPE: DNA
<213> ORGANISM: Human Papillomavirus

<400> SEQUENCE: 266
ctactatccc caccactact ttg                                          23

<210> SEQ ID NO 267
<211> LENGTH: 21
<212> TYPE: DNA
<213> ORGANISM: Human Papillomavirus

<400> SEQUENCE: 267
tttcaaaggt tgtggcaacg g                                            21

<210> SEQ ID NO 268
<211> LENGTH: 20
<212> TYPE: DNA
<213> ORGANISM: Human Papillomavirus
```

-continued

```
<400> SEQUENCE: 268
ttagcccagc acctaaaggc                                            20

<210> SEQ ID NO 269
<211> LENGTH: 23
<212> TYPE: DNA
<213> ORGANISM: Human Papillomavirus

<400> SEQUENCE: 269
tgtggataat acattatatt ttt                                        23

<210> SEQ ID NO 270
<211> LENGTH: 20
<212> TYPE: DNA
<213> ORGANISM: Human Papillomavirus

<400> SEQUENCE: 270
tgtatgacta acctttacac                                            20

<210> SEQ ID NO 271
<211> LENGTH: 20
<212> TYPE: DNA
<213> ORGANISM: Human Papillomavirus

<400> SEQUENCE: 271
tgtacaccgt atgcagcgtg                                            20

<210> SEQ ID NO 272
<211> LENGTH: 19
<212> TYPE: DNA
<213> ORGANISM: Human Papillomavirus

<400> SEQUENCE: 272
tgctggtgta gaggtggag                                             19

<210> SEQ ID NO 273
<211> LENGTH: 24
<212> TYPE: DNA
<213> ORGANISM: Human Papillomavirus

<400> SEQUENCE: 273
tctacaccag gtaatacagg ggat                                       24

<210> SEQ ID NO 274
<211> LENGTH: 21
<212> TYPE: DNA
<213> ORGANISM: Human Papillomavirus

<400> SEQUENCE: 274
tcgtgaactg cctgcatgat a                                          21

<210> SEQ ID NO 275
<211> LENGTH: 20
<212> TYPE: DNA
<213> ORGANISM: Human Papillomavirus

<400> SEQUENCE: 275
tcgcccacta tatcttctgc                                            20

<210> SEQ ID NO 276
<211> LENGTH: 26
<212> TYPE: DNA
<213> ORGANISM: Human Papillomavirus
```

-continued

<400> SEQUENCE: 276
tatattaata ctattatcat tactag                                          26

<210> SEQ ID NO 277
<211> LENGTH: 24
<212> TYPE: DNA
<213> ORGANISM: Human Papillomavirus

<400> SEQUENCE: 277
taggtcaaag cctgctgtag ctac                                            24

<210> SEQ ID NO 278
<211> LENGTH: 20
<212> TYPE: DNA
<213> ORGANISM: Human Papillomavirus

<400> SEQUENCE: 278
tagaccattt gcaggagcgg                                                 20

<210> SEQ ID NO 279
<211> LENGTH: 20
<212> TYPE: DNA
<213> ORGANISM: Human Papillomavirus

<400> SEQUENCE: 279
tagaacgcga tggtacaggc                                                 20

<210> SEQ ID NO 280
<211> LENGTH: 20
<212> TYPE: DNA
<213> ORGANISM: Human Papillomavirus

<400> SEQUENCE: 280
gtttttatgc aggtgtttgc                                                 20

<210> SEQ ID NO 281
<211> LENGTH: 18
<212> TYPE: DNA
<213> ORGANISM: Human Papillomavirus

<400> SEQUENCE: 281
gtgattcagt agttgcac                                                   18

<210> SEQ ID NO 282
<211> LENGTH: 20
<212> TYPE: DNA
<213> ORGANISM: Human Papillomavirus

<400> SEQUENCE: 282
gtcctcccgt atactgtcgc                                                 20

<210> SEQ ID NO 283
<211> LENGTH: 20
<212> TYPE: DNA
<213> ORGANISM: Human Papillomavirus

<400> SEQUENCE: 283
gtagctgcac cgagaagtgg                                                 20

<210> SEQ ID NO 284
<211> LENGTH: 22
<212> TYPE: DNA

-continued

```
<213> ORGANISM: Human Papillomavirus

<400> SEQUENCE: 284
gtaattgtgc agaaggtgta gc                                      22

<210> SEQ ID NO 285
<211> LENGTH: 17
<212> TYPE: DNA
<213> ORGANISM: Human Papillomavirus

<400> SEQUENCE: 285
ggctggattg cgtcgca                                            17

<210> SEQ ID NO 286
<211> LENGTH: 20
<212> TYPE: DNA
<213> ORGANISM: Human Papillomavirus

<400> SEQUENCE: 286
ggataacagc agcctctgcg                                         20

<210> SEQ ID NO 287
<211> LENGTH: 22
<212> TYPE: DNA
<213> ORGANISM: Human Papillomavirus

<400> SEQUENCE: 287
ggagaggata cttcgttgct gc                                      22

<210> SEQ ID NO 288
<211> LENGTH: 20
<212> TYPE: DNA
<213> ORGANISM: Human Papillomavirus

<400> SEQUENCE: 288
ggaagttcat gcgggtggtc                                         20

<210> SEQ ID NO 289
<211> LENGTH: 20
<212> TYPE: DNA
<213> ORGANISM: Human Papillomavirus

<400> SEQUENCE: 289
gctgcaccga gaagtgggtt                                         20

<210> SEQ ID NO 290
<211> LENGTH: 20
<212> TYPE: DNA
<213> ORGANISM: Human Papillomavirus

<400> SEQUENCE: 290
gcgtaggact ctctggagga                                         20

<210> SEQ ID NO 291
<211> LENGTH: 18
<212> TYPE: DNA
<213> ORGANISM: Human Papillomavirus

<400> SEQUENCE: 291
gcgccatgag actgaaac                                           18

<210> SEQ ID NO 292
<211> LENGTH: 21
```

```
<212> TYPE: DNA
<213> ORGANISM: Human Papillomavirus

<400> SEQUENCE: 292
gcctgtaggt gtagctgcac c                                              21

<210> SEQ ID NO 293
<211> LENGTH: 21
<212> TYPE: DNA
<213> ORGANISM: Human Papillomavirus

<400> SEQUENCE: 293
gcatccacaa cattactggc g                                              21

<210> SEQ ID NO 294
<211> LENGTH: 20
<212> TYPE: DNA
<213> ORGANISM: Human Papillomavirus

<400> SEQUENCE: 294
gcaccgagaa gtgggttgac                                                20

<210> SEQ ID NO 295
<211> LENGTH: 18
<212> TYPE: DNA
<213> ORGANISM: Human Papillomavirus

<400> SEQUENCE: 295
gatattagtg gatgtgta                                                  18

<210> SEQ ID NO 296
<211> LENGTH: 20
<212> TYPE: DNA
<213> ORGANISM: Human Papillomavirus

<400> SEQUENCE: 296
gacagcgggt atggcaatac                                                20

<210> SEQ ID NO 297
<211> LENGTH: 20
<212> TYPE: DNA
<213> ORGANISM: Human Papillomavirus

<400> SEQUENCE: 297
gacagcgggt atggcaatac                                                20

<210> SEQ ID NO 298
<211> LENGTH: 19
<212> TYPE: DNA
<213> ORGANISM: Human Papillomavirus

<400> SEQUENCE: 298
cttcctggca cgtacacgc                                                 19

<210> SEQ ID NO 299
<211> LENGTH: 20
<212> TYPE: DNA
<213> ORGANISM: Human Papillomavirus

<400> SEQUENCE: 299
ctgcaccgag aagtgggttg                                                20

<210> SEQ ID NO 300
```

-continued

```
<211> LENGTH: 25
<212> TYPE: DNA
<213> ORGANISM: Human Papillomavirus

<400> SEQUENCE: 300
ctcagccttt gattcctgta atagc                                        25

<210> SEQ ID NO 301
<211> LENGTH: 20
<212> TYPE: DNA
<213> ORGANISM: Human Papillomavirus

<400> SEQUENCE: 301
ctcagatggt gcaggcttcg                                              20

<210> SEQ ID NO 302
<211> LENGTH: 20
<212> TYPE: DNA
<213> ORGANISM: Human Papillomavirus

<400> SEQUENCE: 302
cgggcttcgg taactgactt                                              20

<210> SEQ ID NO 303
<211> LENGTH: 17
<212> TYPE: DNA
<213> ORGANISM: Human Papillomavirus

<400> SEQUENCE: 303
cggacagcgg ctatggc                                                 17

<210> SEQ ID NO 304
<211> LENGTH: 20
<212> TYPE: DNA
<213> ORGANISM: Human Papillomavirus

<400> SEQUENCE: 304
cgatgcacgt tttgtgcgtt                                              20

<210> SEQ ID NO 305
<211> LENGTH: 22
<212> TYPE: DNA
<213> ORGANISM: Human Papillomavirus

<400> SEQUENCE: 305
cctcttcatc tacctgttct gg                                           22

<210> SEQ ID NO 306
<211> LENGTH: 20
<212> TYPE: DNA
<213> ORGANISM: Human Papillomavirus

<400> SEQUENCE: 306
ccgagaagtg ggttgacagg                                              20

<210> SEQ ID NO 307
<211> LENGTH: 20
<212> TYPE: DNA
<213> ORGANISM: Human Papillomavirus

<400> SEQUENCE: 307
cccgaccctg ttccaattcc                                              20
```

-continued

<210> SEQ ID NO 308
<211> LENGTH: 20
<212> TYPE: DNA
<213> ORGANISM: Human Papillomavirus

<400> SEQUENCE: 308
ccagtgacga cacggtatcc                                                        20

<210> SEQ ID NO 309
<211> LENGTH: 21
<212> TYPE: DNA
<213> ORGANISM: Human Papillomavirus

<400> SEQUENCE: 309
cattccattg tttttttacac t                                                     21

<210> SEQ ID NO 310
<211> LENGTH: 26
<212> TYPE: DNA
<213> ORGANISM: Human Papillomavirus

<400> SEQUENCE: 310
caggaaacgt acaagtttaa accata                                                 26

<210> SEQ ID NO 311
<211> LENGTH: 20
<212> TYPE: DNA
<213> ORGANISM: Human Papillomavirus

<400> SEQUENCE: 311
cagagtgggc acgttactgt                                                        20

<210> SEQ ID NO 312
<211> LENGTH: 20
<212> TYPE: DNA
<213> ORGANISM: Human Papillomavirus

<400> SEQUENCE: 312
cactatactg actacatggt                                                        20

<210> SEQ ID NO 313
<211> LENGTH: 20
<212> TYPE: DNA
<213> ORGANISM: Human Papillomavirus

<400> SEQUENCE: 313 cacccctca ccgtattcca                                                         20

<210> SEQ ID NO 314
<211> LENGTH: 20
<212> TYPE: DNA
<213> ORGANISM: Human Papillomavirus

<400> SEQUENCE: 314 cacacccct caccgtattc                                                         20

<210> SEQ ID NO 315
<211> LENGTH: 21
<212> TYPE: DNA
<213> ORGANISM: Human Papillomavirus

<400> SEQUENCE: 315
caatgggcca tacagaggta g                                                      21

-continued

<210> SEQ ID NO 316
<211> LENGTH: 18
<212> TYPE: DNA
<213> ORGANISM: Human Papillomavirus

<400> SEQUENCE: 316
caataagggc tacacgcc                                                                18

<210> SEQ ID NO 317
<211> LENGTH: 20
<212> TYPE: DNA
<213> ORGANISM: Human Papillomavirus

<400> SEQUENCE: 317
atgtgtgttt gtatgtatgg                                                              20

<210> SEQ ID NO 318
<211> LENGTH: 23
<212> TYPE: DNA
<213> ORGANISM: Human Papillomavirus

<400> SEQUENCE: 318
atggcaatac attggaaact ctg                                                          23

<210> SEQ ID NO 319
<211> LENGTH: 22
<212> TYPE: DNA
<213> ORGANISM: Human Papillomavirus

<400> SEQUENCE: 319
atctaggact aatattattg tc                                                           22

<210> SEQ ID NO 320
<211> LENGTH: 19
<212> TYPE: DNA
<213> ORGANISM: Human Papillomavirus

<400> SEQUENCE: 320
atagttctat gtcagcaac                                                               19

<210> SEQ ID NO 321
<211> LENGTH: 20
<212> TYPE: DNA
<213> ORGANISM: Human Papillomavirus

<400> SEQUENCE: 321
aggcctacgt ttactggcac                                                              20

<210> SEQ ID NO 322
<211> LENGTH: 21
<212> TYPE: DNA
<213> ORGANISM: Human Papillomavirus

<400> SEQUENCE: 322
aggatccaac acggcgaccc t                                                            21

<210> SEQ ID NO 323
<211> LENGTH: 20
<212> TYPE: DNA
<213> ORGANISM: Human Papillomavirus

<400> SEQUENCE: 323
agccagtcag ttgctacacc                                                              20

-continued

```
<210> SEQ ID NO 324
<211> LENGTH: 20
<212> TYPE: DNA
<213> ORGANISM: Human Papillomavirus

<400> SEQUENCE: 324
agcaggccta tgtagacgga                                                        20

<210> SEQ ID NO 325
<211> LENGTH: 20
<212> TYPE: DNA
<213> ORGANISM: Human Papillomavirus

<400> SEQUENCE: 325
agcacacccc ctcaccgtat                                                        20

<210> SEQ ID NO 326
<211> LENGTH: 22
<212> TYPE: DNA
<213> ORGANISM: Human Papillomavirus

<400> SEQUENCE: 326
agcaatacac aggaacgtcc ac                                                     22

<210> SEQ ID NO 327
<211> LENGTH: 20
<212> TYPE: DNA
<213> ORGANISM: Human Papillomavirus

<400> SEQUENCE: 327
agcaacctag agctacctgc                                                        20

<210> SEQ ID NO 328
<211> LENGTH: 17
<212> TYPE: DNA
<213> ORGANISM: Human Papillomavirus

<400> SEQUENCE: 328
actgtccact gagtctc                                                           17

<210> SEQ ID NO 329
<211> LENGTH: 17
<212> TYPE: DNA
<213> ORGANISM: Human Papillomavirus

<400> SEQUENCE: 329
actaaatgtc accctag                                                           17

<210> SEQ ID NO 330
<211> LENGTH: 21
<212> TYPE: DNA
<213> ORGANISM: Human Papillomavirus

<400> SEQUENCE: 330
acgtccctgt acctcttcat c                                                      21

<210> SEQ ID NO 331
<211> LENGTH: 20
<212> TYPE: DNA
<213> ORGANISM: Human Papillomavirus

<400> SEQUENCE: 331
```

-continued acgtacccc tgttgagact                                                    20

<210> SEQ ID NO 332
<211> LENGTH: 20
<212> TYPE: DNA
<213> ORGANISM: Human Papillomavirus

<400> SEQUENCE: 332
acggtttctg gcaccgcagg                                                   20

<210> SEQ ID NO 333
<211> LENGTH: 23
<212> TYPE: DNA
<213> ORGANISM: Human Papillomavirus

<400> SEQUENCE: 333
acctcttcat ctacctgttc tgg                                               23

<210> SEQ ID NO 334
<211> LENGTH: 20
<212> TYPE: DNA
<213> ORGANISM: Human Papillomavirus

<400> SEQUENCE: 334 acccccctcac cgtattccag                                                  20

<210> SEQ ID NO 335
<211> LENGTH: 19
<212> TYPE: DNA
<213> ORGANISM: Human Papillomavirus

<400> SEQUENCE: 335
accactaagt tgttgcaca                                                    19

<210> SEQ ID NO 336
<211> LENGTH: 18
<212> TYPE: DNA
<213> ORGANISM: Human Papillomavirus

<400> SEQUENCE: 336
acatacacac gtgtttat                                                     18

<210> SEQ ID NO 337
<211> LENGTH: 21
<212> TYPE: DNA
<213> ORGANISM: Human Papillomavirus

<400> SEQUENCE: 337
aacggtgtct ggtttcagc c                                                  21

<210> SEQ ID NO 338
<211> LENGTH: 22
<212> TYPE: DNA
<213> ORGANISM: Human Papillomavirus

<400> SEQUENCE: 338
aaatattgat gatgaggcac cc                                                22

<210> SEQ ID NO 339
<211> LENGTH: 25
<212> TYPE: DNA
<213> ORGANISM: Human Papillomavirus

<400> SEQUENCE: 339

-continued tctctttttgg tgcataaaat gtctg                                        25

<210> SEQ ID NO 340
<211> LENGTH: 25
<212> TYPE: DNA
<213> ORGANISM: Human Papillomavirus

<400> SEQUENCE: 340
tccatatgta ttacagagtc ctcac                                        25

<210> SEQ ID NO 341
<211> LENGTH: 28
<212> TYPE: DNA
<213> ORGANISM: Human Papillomavirus

<400> SEQUENCE: 341
gtactatatc atatccattg ccagtcta                                     28

<210> SEQ ID NO 342
<211> LENGTH: 26
<212> TYPE: DNA
<213> ORGANISM: Human Papillomavirus

<400> SEQUENCE: 342
gtactatatc atatccattg ccagtc                                       26

<210> SEQ ID NO 343
<211> LENGTH: 20
<212> TYPE: DNA
<213> ORGANISM: Human Papillomavirus

<400> SEQUENCE: 343
ggtaagggaa ccaaaaacgc                                              20

<210> SEQ ID NO 344
<211> LENGTH: 20
<212> TYPE: DNA
<213> ORGANISM: Human Papillomavirus

<400> SEQUENCE: 344
ggggtttccg gtgtctggct                                              20

<210> SEQ ID NO 345
<211> LENGTH: 19
<212> TYPE: DNA
<213> ORGANISM: Human Papillomavirus

<400> SEQUENCE: 345
ggaatggttg gcaagcagt                                               19

<210> SEQ ID NO 346
<211> LENGTH: 22
<212> TYPE: DNA
<213> ORGANISM: Human Papillomavirus

<400> SEQUENCE: 346
gcagcttatt ctgtgtggac at                                           22

<210> SEQ ID NO 347
<211> LENGTH: 26
<212> TYPE: DNA
<213> ORGANISM: Human Papillomavirus -continued

<400> SEQUENCE: 347
ctatgtacag tagttatgca caatgc                                    26

<210> SEQ ID NO 348
<211> LENGTH: 20
<212> TYPE: DNA
<213> ORGANISM: Human Papillomavirus

<400> SEQUENCE: 348
cgcgacccat accaaagccg                                           20

<210> SEQ ID NO 349
<211> LENGTH: 27
<212> TYPE: DNA
<213> ORGANISM: Human Papillomavirus

<400> SEQUENCE: 349
catgtaaata tatacacagc acaggac                                   27

<210> SEQ ID NO 350
<211> LENGTH: 22
<212> TYPE: DNA
<213> ORGANISM: Human Papillomavirus

<400> SEQUENCE: 350
attgttgaat tgtggctcca tg                                        22

<210> SEQ ID NO 351
<211> LENGTH: 18
<212> TYPE: DNA
<213> ORGANISM: Human Papillomavirus

<400> SEQUENCE: 351
atgcgtgcca aatccctg                                             18

<210> SEQ ID NO 352
<211> LENGTH: 21
<212> TYPE: DNA
<213> ORGANISM: Human Papillomavirus

<400> SEQUENCE: 352
atctgcctct gtgttttcca g                                         21

<210> SEQ ID NO 353
<211> LENGTH: 23
<212> TYPE: DNA
<213> ORGANISM: Human Papillomavirus

<400> SEQUENCE: 353
agtgatatta gtggatgtgt aga                                       23

<210> SEQ ID NO 354
<211> LENGTH: 24
<212> TYPE: DNA
<213> ORGANISM: Human Papillomavirus

<400> SEQUENCE: 354
aggctcacaa aacagtacct atag                                      24

<210> SEQ ID NO 355
<211> LENGTH: 26
<212> TYPE: DNA
<213> ORGANISM: Human Papillomavirus -continued

<400> SEQUENCE: 355
actatatcat atccattgcc agtcta                                        26

<210> SEQ ID NO 356
<211> LENGTH: 19
<212> TYPE: DNA
<213> ORGANISM: Human Papillomavirus

<400> SEQUENCE: 356
accgaaatcg gttgaaccg                                                19

<210> SEQ ID NO 357
<211> LENGTH: 24
<212> TYPE: DNA
<213> ORGANISM: Human Papillomavirus

<400> SEQUENCE: 357
acatatagct tttaatctag gact                                          24

<210> SEQ ID NO 358
<211> LENGTH: 19
<212> TYPE: DNA
<213> ORGANISM: Human Papillomavirus

<400> SEQUENCE: 358
gtccaaggcg gggtctgca                                                19

<210> SEQ ID NO 359
<211> LENGTH: 23
<212> TYPE: DNA
<213> ORGANISM: Human Papillomavirus

<400> SEQUENCE: 359
ggtcaaagcc tgctgtagct acc                                           23

<210> SEQ ID NO 360
<211> LENGTH: 17
<212> TYPE: DNA
<213> ORGANISM: Human Papillomavirus

<400> SEQUENCE: 360
gggatgtgcc gtcgcgg                                                  17

<210> SEQ ID NO 361
<211> LENGTH: 26
<212> TYPE: DNA
<213> ORGANISM: Human Papillomavirus

<400> SEQUENCE: 361
ggcagtacta gtaggtgctt catctg                                        26

<210> SEQ ID NO 362
<211> LENGTH: 24
<212> TYPE: DNA
<213> ORGANISM: Human Papillomavirus

<400> SEQUENCE: 362
ggaggagtca aattctgatt cccg                                          24

<210> SEQ ID NO 363
<211> LENGTH: 20
<212> TYPE: DNA

<213> ORGANISM: Human Papillomavirus

<400> SEQUENCE: 363
gcgggttgtt gcctggatgc                                                    20

<210> SEQ ID NO 364
<211> LENGTH: 26
<212> TYPE: DNA
<213> ORGANISM: Human Papillomavirus

<400> SEQUENCE: 364
gcaaatgtaa cacaagccaa tactgc                                             26

<210> SEQ ID NO 365
<211> LENGTH: 22
<212> TYPE: DNA
<213> ORGANISM: Human Papillomavirus

<400> SEQUENCE: 365
gaccaccacc accacctcca cg                                                 22

<210> SEQ ID NO 366
<211> LENGTH: 23
<212> TYPE: DNA
<213> ORGANISM: Human Papillomavirus

<400> SEQUENCE: 366
gacattgcaa cacacacaca agc                                                23

<210> SEQ ID NO 367
<211> LENGTH: 21
<212> TYPE: DNA
<213> ORGANISM: Human Papillomavirus

<400> SEQUENCE: 367
cgtgctgttc tattgtccaa g                                                  21

<210> SEQ ID NO 368
<211> LENGTH: 22
<212> TYPE: DNA
<213> ORGANISM: Human Papillomavirus

<400> SEQUENCE: 368
cacagcaccc tcagtctacc ag                                                 22

<210> SEQ ID NO 369
<211> LENGTH: 22
<212> TYPE: DNA
<213> ORGANISM: Human Papillomavirus

<400> SEQUENCE: 369
cacacaacaa cacactaccg cc                                                 22

<210> SEQ ID NO 370
<211> LENGTH: 20
<212> TYPE: DNA
<213> ORGANISM: Human Papillomavirus

<400> SEQUENCE: 370
caagggatgt gccgtcgcgg                                                    20

<210> SEQ ID NO 371
<211> LENGTH: 20

<212> TYPE: DNA
<213> ORGANISM: Human Papillomavirus

<400> SEQUENCE: 371 atcataccccc tccgcaacgc                                    20

<210> SEQ ID NO 372
<211> LENGTH: 18
<212> TYPE: DNA
<213> ORGANISM: Human Papillomavirus

<400> SEQUENCE: 372
acttgggccc ccaaacgt                                       18

<210> SEQ ID NO 373
<211> LENGTH: 24
<212> TYPE: DNA
<213> ORGANISM: Human Papillomavirus

<400> SEQUENCE: 373
tccagtattc tccacggtta cctg                                24

<210> SEQ ID NO 374
<211> LENGTH: 24
<212> TYPE: DNA
<213> ORGANISM: Human Papillomavirus

<400> SEQUENCE: 374
cggctatggc tattctgaag tgga                                24

<210> SEQ ID NO 375
<211> LENGTH: 22
<212> TYPE: DNA
<213> ORGANISM: Human Papillomavirus

<400> SEQUENCE: 375
cacaacaaca cactaccgcc tt                                  22

<210> SEQ ID NO 376
<211> LENGTH: 23
<212> TYPE: DNA
<213> ORGANISM: Human Papillomavirus

<400> SEQUENCE: 376
actaggtcaa agcctgctgt agc                                 23

<210> SEQ ID NO 377
<211> LENGTH: 17
<212> TYPE: DNA
<213> ORGANISM: Human Papillomavirus

<400> SEQUENCE: 377
ttgcgacaca ctctgcg                                        17

<210> SEQ ID NO 378
<211> LENGTH: 21
<212> TYPE: DNA
<213> ORGANISM: Human Papillomavirus

<400> SEQUENCE: 378
ttgaaatgct actggaccca c                                   21

<210> SEQ ID NO 379

```
<211> LENGTH: 17
<212> TYPE: DNA
<213> ORGANISM: Human Papillomavirus

<400> SEQUENCE: 379
tgggcaaaat gacgggt                                                                17

<210> SEQ ID NO 380
<211> LENGTH: 16
<212> TYPE: DNA
<213> ORGANISM: Human Papillomavirus

<400> SEQUENCE: 380
tggaccggcc agatgg                                                                 16

<210> SEQ ID NO 381
<211> LENGTH: 20
<212> TYPE: DNA
<213> ORGANISM: Human Papillomavirus

<400> SEQUENCE: 381
tgcccatcta cctgtaaggg                                                             20

<210> SEQ ID NO 382
<211> LENGTH: 19
<212> TYPE: DNA
<213> ORGANISM: Human Papillomavirus

<400> SEQUENCE: 382 tgaggggtg gaacataga                                                               19

<210> SEQ ID NO 383
<211> LENGTH: 18
<212> TYPE: DNA
<213> ORGANISM: Human Papillomavirus

<400> SEQUENCE: 383
tccttgtgca aaaccgcc                                                               18

<210> SEQ ID NO 384
<211> LENGTH: 20
<212> TYPE: DNA
<213> ORGANISM: Human Papillomavirus

<400> SEQUENCE: 384
tccgttagtt ccctggtttg                                                             20

<210> SEQ ID NO 385
<211> LENGTH: 27
<212> TYPE: DNA
<213> ORGANISM: Human Papillomavirus

<400> SEQUENCE: 385
tatgtttgtg gtatgttatg taaggtg                                                     27

<210> SEQ ID NO 386
<211> LENGTH: 19
<212> TYPE: DNA
<213> ORGANISM: Human Papillomavirus

<400> SEQUENCE: 386
tatgctgccg ccattttcc                                                              19
```

```
<210> SEQ ID NO 387
<211> LENGTH: 22
<212> TYPE: DNA
<213> ORGANISM: Human Papillomavirus

<400> SEQUENCE: 387
tatctacctg tacgggcgta ag                                              22

<210> SEQ ID NO 388
<211> LENGTH: 18
<212> TYPE: DNA
<213> ORGANISM: Human Papillomavirus

<400> SEQUENCE: 388
tacttctgtc gctgctcc                                                   18

<210> SEQ ID NO 389
<211> LENGTH: 21
<212> TYPE: DNA
<213> ORGANISM: Human Papillomavirus

<400> SEQUENCE: 389
gttgtttgtt gccacttttg c                                               21

<210> SEQ ID NO 390
<211> LENGTH: 21
<212> TYPE: DNA
<213> ORGANISM: Human Papillomavirus

<400> SEQUENCE: 390
gttcctagca tacatacgcc g                                               21

<210> SEQ ID NO 391
<211> LENGTH: 21
<212> TYPE: DNA
<213> ORGANISM: Human Papillomavirus

<400> SEQUENCE: 391
gttccctggt ttgaaacagc c                                               21

<210> SEQ ID NO 392
<211> LENGTH: 16
<212> TYPE: DNA
<213> ORGANISM: Human Papillomavirus

<400> SEQUENCE: 392
gtgtgtcacg cttgcg                                                     16

<210> SEQ ID NO 393
<211> LENGTH: 21
<212> TYPE: DNA
<213> ORGANISM: Human Papillomavirus

<400> SEQUENCE: 393
gtccggcact tctgtatcaa t                                               21

<210> SEQ ID NO 394
<211> LENGTH: 27
<212> TYPE: DNA
<213> ORGANISM: Human Papillomavirus

<400> SEQUENCE: 394
gtaatggtat agaaaaccaa gcatgta                                         27
```

-continued

<210> SEQ ID NO 395
<211> LENGTH: 21
<212> TYPE: DNA
<213> ORGANISM: Human Papillomavirus

<400> SEQUENCE: 395
gtaatcagca aacagtgtgc c                                              21

<210> SEQ ID NO 396
<211> LENGTH: 20
<212> TYPE: DNA
<213> ORGANISM: Human Papillomavirus

<400> SEQUENCE: 396
ggtgttgtta gtggacggtc                                               20

<210> SEQ ID NO 397
<211> LENGTH: 19
<212> TYPE: DNA
<213> ORGANISM: Human Papillomavirus

<400> SEQUENCE: 397
ggcgacacaa tttggttgc                                                19

<210> SEQ ID NO 398
<211> LENGTH: 23
<212> TYPE: DNA
<213> ORGANISM: Human Papillomavirus

<400> SEQUENCE: 398
ggacagtgga tatggctatt ctg                                           23

<210> SEQ ID NO 399
<211> LENGTH: 20
<212> TYPE: DNA
<213> ORGANISM: Human Papillomavirus

<400> SEQUENCE: 399
ggacagcggg tatggctata                                               20

<210> SEQ ID NO 400
<211> LENGTH: 18
<212> TYPE: DNA
<213> ORGANISM: Human Papillomavirus

<400> SEQUENCE: 400
ggaaaacgtc ccagaacc                                                 18

<210> SEQ ID NO 401
<211> LENGTH: 19
<212> TYPE: DNA
<213> ORGANISM: Human Papillomavirus

<400> SEQUENCE: 401
gcttgcggcc accatttac                                                19

<210> SEQ ID NO 402
<211> LENGTH: 23
<212> TYPE: DNA
<213> ORGANISM: Human Papillomavirus

<400> SEQUENCE: 402
gctgtttacc actaccatac gta                                           23

-continued

```
<210> SEQ ID NO 403
<211> LENGTH: 26
<212> TYPE: DNA
<213> ORGANISM: Human Papillomavirus

<400> SEQUENCE: 403
gctgtatttc attgtatgga catagc                                        26

<210> SEQ ID NO 404
<211> LENGTH: 15
<212> TYPE: DNA
<213> ORGANISM: Human Papillomavirus

<400> SEQUENCE: 404
gcgagcacgt ggacc                                                    15

<210> SEQ ID NO 405
<211> LENGTH: 20
<212> TYPE: DNA
<213> ORGANISM: Human Papillomavirus

<400> SEQUENCE: 405
gccatgtttc tctacctgcg                                               20

<210> SEQ ID NO 406
<211> LENGTH: 24
<212> TYPE: DNA
<213> ORGANISM: Human Papillomavirus

<400> SEQUENCE: 406
gcatatctac actgtttccc gtac                                          24

<210> SEQ ID NO 407
<211> LENGTH: 25
<212> TYPE: DNA
<213> ORGANISM: Human Papillomavirus

<400> SEQUENCE: 407
gcaacataca catatacaca tacac                                         25

<210> SEQ ID NO 408
<211> LENGTH: 16
<212> TYPE: DNA
<213> ORGANISM: Human Papillomavirus

<400> SEQUENCE: 408
gagaggaccg cagacg                                                   16

<210> SEQ ID NO 409
<211> LENGTH: 19
<212> TYPE: DNA
<213> ORGANISM: Human Papillomavirus

<400> SEQUENCE: 409
gacccgtcat tttgcccat                                                19

<210> SEQ ID NO 410
<211> LENGTH: 20
<212> TYPE: DNA
<213> ORGANISM: Human Papillomavirus

<400> SEQUENCE: 410
```

-continued gacagcgggt atggcaatac                                                    20

<210> SEQ ID NO 411
<211> LENGTH: 20
<212> TYPE: DNA
<213> ORGANISM: Human Papillomavirus

<400> SEQUENCE: 411
gaatgcacaa acgcaaagtg                                                    20

<210> SEQ ID NO 412
<211> LENGTH: 24
<212> TYPE: DNA
<213> ORGANISM: Human Papillomavirus

<400> SEQUENCE: 412
cttacatttg gtgtgtttat cccc                                               24

<210> SEQ ID NO 413
<211> LENGTH: 25
<212> TYPE: DNA
<213> ORGANISM: Human Papillomavirus

<400> SEQUENCE: 413
ctgttatagg tgtgctctct gtttc                                              25

<210> SEQ ID NO 414
<211> LENGTH: 23
<212> TYPE: DNA
<213> ORGANISM: Human Papillomavirus

<400> SEQUENCE: 414
ctgcaaacac ataaatggaa agc                                                23

<210> SEQ ID NO 415
<211> LENGTH: 29
<212> TYPE: DNA
<213> ORGANISM: Human Papillomavirus

<400> SEQUENCE: 415
ctcactttct actgcattag ctacattgc                                          29

<210> SEQ ID NO 416
<211> LENGTH: 22
<212> TYPE: DNA
<213> ORGANISM: Human Papillomavirus

<400> SEQUENCE: 416
ctacagttac ctccacttca gc                                                 22

<210> SEQ ID NO 417
<211> LENGTH: 21
<212> TYPE: DNA
<213> ORGANISM: Human Papillomavirus

<400> SEQUENCE: 417
cgtgctgttc tattgtccaa g                                                  21

<210> SEQ ID NO 418
<211> LENGTH: 15
<212> TYPE: DNA
<213> ORGANISM: Human Papillomavirus

<400> SEQUENCE: 418

-continued cgggctcaga gggct                                                15

<210> SEQ ID NO 419
<211> LENGTH: 20
<212> TYPE: DNA
<213> ORGANISM: Human Papillomavirus

<400> SEQUENCE: 419
cggacagtgg atatggcaat                                           20

<210> SEQ ID NO 420
<211> LENGTH: 18
<212> TYPE: DNA
<213> ORGANISM: Human Papillomavirus

<400> SEQUENCE: 420
cctgaccatc tcccccat                                             18

<210> SEQ ID NO 421
<211> LENGTH: 22
<212> TYPE: DNA
<213> ORGANISM: Human Papillomavirus

<400> SEQUENCE: 421
cctatggcac ttgtacatta cc                                        22

<210> SEQ ID NO 422
<211> LENGTH: 21
<212> TYPE: DNA
<213> ORGANISM: Human Papillomavirus

<400> SEQUENCE: 422
cccgccacta cacatactat g                                         21

<210> SEQ ID NO 423
<211> LENGTH: 21
<212> TYPE: DNA
<213> ORGANISM: Human Papillomavirus

<400> SEQUENCE: 423
ccattttccc cttcctcttc c                                         21

<210> SEQ ID NO 424
<211> LENGTH: 21
<212> TYPE: DNA
<213> ORGANISM: Human Papillomavirus

<400> SEQUENCE: 424
ccacacagca atgatgctaa c                                         21

<210> SEQ ID NO 425
<211> LENGTH: 20
<212> TYPE: DNA
<213> ORGANISM: Human Papillomavirus

<400> SEQUENCE: 425
cataacaagg atggcggacg                                           20

<210> SEQ ID NO 426
<211> LENGTH: 25
<212> TYPE: DNA
<213> ORGANISM: Human Papillomavirus -continued

```
<400> SEQUENCE: 426
caggaaaaca cataaccatg catac                                              25

<210> SEQ ID NO 427
<211> LENGTH: 21
<212> TYPE: DNA
<213> ORGANISM: Human Papillomavirus

<400> SEQUENCE: 427
cacggtatcc gctactcagc t                                                  21

<210> SEQ ID NO 428
<211> LENGTH: 17
<212> TYPE: DNA
<213> ORGANISM: Human Papillomavirus

<400> SEQUENCE: 428
cacactaggc aacccgc                                                       17

<210> SEQ ID NO 429
<211> LENGTH: 23
<212> TYPE: DNA
<213> ORGANISM: Human Papillomavirus

<400> SEQUENCE: 429
cacaatttgg ttgccttctt cat                                                23

<210> SEQ ID NO 430
<211> LENGTH: 23
<212> TYPE: DNA
<213> ORGANISM: Human Papillomavirus

<400> SEQUENCE: 430
caacgcaggt agagaaacat ggc                                                23

<210> SEQ ID NO 431
<211> LENGTH: 20
<212> TYPE: DNA
<213> ORGANISM: Human Papillomavirus

<400> SEQUENCE: 431
caacgcaggt agagaaacat                                                    20

<210> SEQ ID NO 432
<211> LENGTH: 24
<212> TYPE: DNA
<213> ORGANISM: Human Papillomavirus

<400> SEQUENCE: 432
caacataatc cattgtcctg actc                                               24

<210> SEQ ID NO 433
<211> LENGTH: 20
<212> TYPE: DNA
<213> ORGANISM: Human Papillomavirus

<400> SEQUENCE: 433
attgcaggtt actgggttcc                                                    20

<210> SEQ ID NO 434
<211> LENGTH: 21
<212> TYPE: DNA
<213> ORGANISM: Human Papillomavirus
```

<400> SEQUENCE: 434
atgtttctct acctgcgttc c                                                     21

<210> SEQ ID NO 435
<211> LENGTH: 21
<212> TYPE: DNA
<213> ORGANISM: Human Papillomavirus

<400> SEQUENCE: 435
atgttggtgt tggtatgttg t                                                     21

<210> SEQ ID NO 436
<211> LENGTH: 20
<212> TYPE: DNA
<213> ORGANISM: Human Papillomavirus

<400> SEQUENCE: 436
atatcgccat tttgcccctc                                                       20

<210> SEQ ID NO 437
<211> LENGTH: 22
<212> TYPE: DNA
<213> ORGANISM: Human Papillomavirus

<400> SEQUENCE: 437
ataaacacta tagccgaggc ag                                                    22

<210> SEQ ID NO 438
<211> LENGTH: 22
<212> TYPE: DNA
<213> ORGANISM: Human Papillomavirus

<400> SEQUENCE: 438
ataaacacta tagccgaggc ag                                                    22

<210> SEQ ID NO 439
<211> LENGTH: 20
<212> TYPE: DNA
<213> ORGANISM: Human Papillomavirus

<400> SEQUENCE: 439
agacagcggc tatggcaata                                                       20

<210> SEQ ID NO 440
<211> LENGTH: 22
<212> TYPE: DNA
<213> ORGANISM: Human Papillomavirus

<400> SEQUENCE: 440
agacagcgga tatggcaata ct                                                    22

<210> SEQ ID NO 441
<211> LENGTH: 23
<212> TYPE: DNA
<213> ORGANISM: Human Papillomavirus

<400> SEQUENCE: 441
acttctcata caggttctac agg                                                   23

<210> SEQ ID NO 442
<211> LENGTH: 20
<212> TYPE: DNA

<213> ORGANISM: Human Papillomavirus

<400> SEQUENCE: 442
actgcatatc gccattttgc                                                                                              20

<210> SEQ ID NO 443
<211> LENGTH: 22
<212> TYPE: DNA
<213> ORGANISM: Human Papillomavirus

<400> SEQUENCE: 443
actacagtta cctccacttc ag                                                                                          22

<210> SEQ ID NO 444
<211> LENGTH: 22
<212> TYPE: DNA
<213> ORGANISM: Human Papillomavirus

<400> SEQUENCE: 444
accaacaaca actactagcc ag                                                                                          22

<210> SEQ ID NO 445
<211> LENGTH: 26
<212> TYPE: DNA
<213> ORGANISM: Human Papillomavirus

<400> SEQUENCE: 445
acattacaaa tcaaaacaca caaagc                                                                                      26

<210> SEQ ID NO 446
<211> LENGTH: 20
<212> TYPE: DNA
<213> ORGANISM: Human Papillomavirus

<400> SEQUENCE: 446
acacactagt ctgtgagcct                                                                                              20

<210> SEQ ID NO 447
<211> LENGTH: 19
<212> TYPE: DNA
<213> ORGANISM: Human Papillomavirus

<400> SEQUENCE: 447
aaccaaattg tgtcgccac                                                                                               19

<210> SEQ ID NO 448
<211> LENGTH: 23
<212> TYPE: DNA
<213> ORGANISM: Human Papillomavirus

<400> SEQUENCE: 448
aaacacattg gaggcatatc ttg                                                                                          23

<210> SEQ ID NO 449
<211> LENGTH: 21
<212> TYPE: DNA
<213> ORGANISM: Human Papillomavirus

<400> SEQUENCE: 449
aaaacctgtt gtaggtggga c                                                                                            21

<210> SEQ ID NO 450
<211> LENGTH: 20

-continued

<212> TYPE: DNA
<213> ORGANISM: Human Papillomavirus

<400> SEQUENCE: 450
ttactagccc ccacccccact                                                          20

<210> SEQ ID NO 451
<211> LENGTH: 20
<212> TYPE: DNA
<213> ORGANISM: Human Papillomavirus

<400> SEQUENCE: 451
gtgctgggca agatggtgta                                                           20

<210> SEQ ID NO 452
<211> LENGTH: 23
<212> TYPE: DNA
<213> ORGANISM: Human Papillomavirus

<400> SEQUENCE: 452
ggacaaccaa agttgtgcca aga                                                       23

<210> SEQ ID NO 453
<211> LENGTH: 18
<212> TYPE: DNA
<213> ORGANISM: Human Papillomavirus

<400> SEQUENCE: 453
gcgcagcaga tggcagac                                                             18

<210> SEQ ID NO 454
<211> LENGTH: 18
<212> TYPE: DNA
<213> ORGANISM: Human Papillomavirus

<400> SEQUENCE: 454
gcagtgacga gtccccgt                                                             18

<210> SEQ ID NO 455
<211> LENGTH: 18
<212> TYPE: DNA
<213> ORGANISM: Human Papillomavirus

<400> SEQUENCE: 455
gacctccgca gtgtccgt                                                             18

<210> SEQ ID NO 456
<211> LENGTH: 19
<212> TYPE: DNA
<213> ORGANISM: Human Papillomavirus

<400> SEQUENCE: 456
ctgccctacc ctgtgtccc                                                            19

<210> SEQ ID NO 457
<211> LENGTH: 19
<212> TYPE: DNA
<213> ORGANISM: Human Papillomavirus

<400> SEQUENCE: 457
cccgtctacc tggtctgcc                                                            19

<210> SEQ ID NO 458

-continued

```
<211> LENGTH: 20
<212> TYPE: DNA
<213> ORGANISM: Human Papillomavirus

<400> SEQUENCE: 458
cccgcaaaag gttgttgggg                                              20

<210> SEQ ID NO 459
<211> LENGTH: 19
<212> TYPE: DNA
<213> ORGANISM: Human Papillomavirus

<400> SEQUENCE: 459
cccgacctgt gacccaagt                                               19

<210> SEQ ID NO 460
<211> LENGTH: 18
<212> TYPE: DNA
<213> ORGANISM: Human Papillomavirus

<400> SEQUENCE: 460
cagtgtccgt gggtgcca                                                18

<210> SEQ ID NO 461
<211> LENGTH: 18
<212> TYPE: DNA
<213> ORGANISM: Human Papillomavirus

<400> SEQUENCE: 461
atctggccgg tccacacc                                                18

<210> SEQ ID NO 462
<211> LENGTH: 19
<212> TYPE: DNA
<213> ORGANISM: Human Papillomavirus

<400> SEQUENCE: 462
taggcagaaa taccagggg                                               19

<210> SEQ ID NO 463
<211> LENGTH: 20
<212> TYPE: DNA
<213> ORGANISM: Human Papillomavirus

<400> SEQUENCE: 463
caacaacaca ctaccgcctt                                              20

<210> SEQ ID NO 464
<211> LENGTH: 20
<212> TYPE: DNA
<213> ORGANISM: Human Papillomavirus

<400> SEQUENCE: 464
agcaacctag agctacctgc                                              20

<210> SEQ ID NO 465
<211> LENGTH: 21
<212> TYPE: DNA
<213> ORGANISM: Human Papillomavirus

<400> SEQUENCE: 465
aaaacctgtt gtaggtggga c                                            21
```

-continued

<210> SEQ ID NO 466
<211> LENGTH: 24
<212> TYPE: DNA
<213> ORGANISM: Human Papillomavirus

<400> SEQUENCE: 466
ttcctctgat agtaatcctg catc                                                      24

<210> SEQ ID NO 467
<211> LENGTH: 27
<212> TYPE: DNA
<213> ORGANISM: Human Papillomavirus

<400> SEQUENCE: 467
tgtttttttg aaaagacttg gtgcaga                                                   27

<210> SEQ ID NO 468
<211> LENGTH: 21
<212> TYPE: DNA
<213> ORGANISM: Human Papillomavirus

<400> SEQUENCE: 468
tgtattgcca tacccgctgt c                                                         21

<210> SEQ ID NO 469
<211> LENGTH: 20
<212> TYPE: DNA
<213> ORGANISM: Human Papillomavirus

<400> SEQUENCE: 469
tggaatgcac acccacaacg                                                           20

<210> SEQ ID NO 470
<211> LENGTH: 21
<212> TYPE: DNA
<213> ORGANISM: Human Papillomavirus

<400> SEQUENCE: 470
tgcgaaggta cagatgggga g                                                         21

<210> SEQ ID NO 471
<211> LENGTH: 21
<212> TYPE: DNA
<213> ORGANISM: Human Papillomavirus

<400> SEQUENCE: 471
tgaaacaatg cctgcgctac c                                                         21

<210> SEQ ID NO 472
<211> LENGTH: 19
<212> TYPE: DNA
<213> ORGANISM: Human Papillomavirus

<400> SEQUENCE: 472
tcttccggtt cgccatttc                                                            19

<210> SEQ ID NO 473
<211> LENGTH: 21
<212> TYPE: DNA
<213> ORGANISM: Human Papillomavirus

<400> SEQUENCE: 473
tctgtcccct cggtatttac c                                                         21

-continued

<210> SEQ ID NO 474
<211> LENGTH: 19
<212> TYPE: DNA
<213> ORGANISM: Human Papillomavirus

<400> SEQUENCE: 474
tcctgttctg tgtgcagcc                                                     19

<210> SEQ ID NO 475
<211> LENGTH: 18
<212> TYPE: DNA
<213> ORGANISM: Human Papillomavirus

<400> SEQUENCE: 475
tccccgtttg gacgctat                                                      18

<210> SEQ ID NO 476
<211> LENGTH: 23
<212> TYPE: DNA
<213> ORGANISM: Human Papillomavirus

<400> SEQUENCE: 476
tccattattg aacctccaca ggc                                                23

<210> SEQ ID NO 477
<211> LENGTH: 21
<212> TYPE: DNA
<213> ORGANISM: Human Papillomavirus

<400> SEQUENCE: 477
tagacaaaga gttaagcccg c                                                  21

<210> SEQ ID NO 478
<211> LENGTH: 21
<212> TYPE: DNA
<213> ORGANISM: Human Papillomavirus

<400> SEQUENCE: 478
tactttgtaa acatcccccc g                                                  21

<210> SEQ ID NO 479
<211> LENGTH: 22
<212> TYPE: DNA
<213> ORGANISM: Human Papillomavirus

<400> SEQUENCE: 479
tacttatggg ttctaggccc gt                                                 22

<210> SEQ ID NO 480
<211> LENGTH: 25
<212> TYPE: DNA
<213> ORGANISM: Human Papillomavirus

<400> SEQUENCE: 480
tactaattct gaaaaactca ccccg                                              25

<210> SEQ ID NO 481
<211> LENGTH: 22
<212> TYPE: DNA
<213> ORGANISM: Human Papillomavirus

<400> SEQUENCE: 481
taccaagtgt ggctacaatg cc                                                 22

<210> SEQ ID NO 482
<211> LENGTH: 19
<212> TYPE: DNA
<213> ORGANISM: Human Papillomavirus

<400> SEQUENCE: 482
taatccacac cccccgaca                                                          19

<210> SEQ ID NO 483
<211> LENGTH: 23
<212> TYPE: DNA
<213> ORGANISM: Human Papillomavirus

<400> SEQUENCE: 483
gttttataac caccgtcgac ttc                                                     23

<210> SEQ ID NO 484
<211> LENGTH: 19
<212> TYPE: DNA
<213> ORGANISM: Human Papillomavirus

<400> SEQUENCE: 484
gttgctctgc cccatcact                                                          19

<210> SEQ ID NO 485
<211> LENGTH: 25
<212> TYPE: DNA
<213> ORGANISM: Human Papillomavirus

<400> SEQUENCE: 485
gttgcaggta ctaacatact ttgac                                                   25

<210> SEQ ID NO 486
<211> LENGTH: 22
<212> TYPE: DNA
<213> ORGANISM: Human Papillomavirus

<400> SEQUENCE: 486
gttcgccatt tctctctacc tg                                                      22

<210> SEQ ID NO 487
<211> LENGTH: 23
<212> TYPE: DNA
<213> ORGANISM: Human Papillomavirus

<400> SEQUENCE: 487
gtgtttatct acctgtactg gcg                                                     23

<210> SEQ ID NO 488
<211> LENGTH: 21
<212> TYPE: DNA
<213> ORGANISM: Human Papillomavirus

<400> SEQUENCE: 488
gtgttctacc tgtgtctgct g                                                       21

<210> SEQ ID NO 489
<211> LENGTH: 18
<212> TYPE: DNA
<213> ORGANISM: Human Papillomavirus

<400> SEQUENCE: 489

-continued

```
gtggaagtgg acctgcgg                                                    18

<210> SEQ ID NO 490
<211> LENGTH: 20
<212> TYPE: DNA
<213> ORGANISM: Human Papillomavirus

<400> SEQUENCE: 490
gtctgccatt gttgtcactc                                                  20

<210> SEQ ID NO 491
<211> LENGTH: 22
<212> TYPE: DNA
<213> ORGANISM: Human Papillomavirus

<400> SEQUENCE: 491
gtctagtacc ctcagatcca ac                                               22

<210> SEQ ID NO 492
<211> LENGTH: 19
<212> TYPE: DNA
<213> ORGANISM: Human Papillomavirus

<400> SEQUENCE: 492
gtccgccata ttccacctc                                                   19

<210> SEQ ID NO 493
<211> LENGTH: 22
<212> TYPE: DNA
<213> ORGANISM: Human Papillomavirus

<400> SEQUENCE: 493
gtccactgct ctccttttag cc                                               22

<210> SEQ ID NO 494
<211> LENGTH: 23
<212> TYPE: DNA
<213> ORGANISM: Human Papillomavirus
<220> FEATURE:
<221> NAME/KEY: 494
<222> LOCATION: (6)..(16)
<223> OTHER INFORMATION: 6,16: n is one of the following nucleotides: a
      or g or c or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 494
gtcaantgcc cattgnacca att                                              23

<210> SEQ ID NO 495
<211> LENGTH: 22
<212> TYPE: DNA
<213> ORGANISM: Human Papillomavirus

<400> SEQUENCE: 495
gtattgccat atccactgtc cg                                               22

<210> SEQ ID NO 496
<211> LENGTH: 22
<212> TYPE: DNA
```

<213> ORGANISM: Human Papillomavirus

<400> SEQUENCE: 496
gtatggccat acccactgtc gc                                              22

<210> SEQ ID NO 497
<211> LENGTH: 20
<212> TYPE: DNA
<213> ORGANISM: Human Papillomavirus

<400> SEQUENCE: 497
gtatggccat acccactgtc                                                 20

<210> SEQ ID NO 498
<211> LENGTH: 20
<212> TYPE: DNA
<213> ORGANISM: Human Papillomavirus

<400> SEQUENCE: 498
gtacttctcg cacggtgtcc                                                 20

<210> SEQ ID NO 499
<211> LENGTH: 18
<212> TYPE: DNA
<213> ORGANISM: Human Papillomavirus

<400> SEQUENCE: 499
ggtttcctgc cgcttcag                                                   18

<210> SEQ ID NO 500
<211> LENGTH: 23
<212> TYPE: DNA
<213> ORGANISM: Human Papillomavirus

<400> SEQUENCE: 500
ggtctgtctc tgtttcatct gtc                                             23

<210> SEQ ID NO 501
<211> LENGTH: 18
<212> TYPE: DNA
<213> ORGANISM: Human Papillomavirus

<400> SEQUENCE: 501
ggtccgccat gttctgtc                                                   18

<210> SEQ ID NO 502
<211> LENGTH: 22
<212> TYPE: DNA
<213> ORGANISM: Human Papillomavirus

<400> SEQUENCE: 502
gggtatggct atactgaagt gg                                              22

<210> SEQ ID NO 503
<211> LENGTH: 22
<212> TYPE: DNA
<213> ORGANISM: Human Papillomavirus

<400> SEQUENCE: 503
gggtatggca atacgcaagt gg                                              22

<210> SEQ ID NO 504
<211> LENGTH: 15

<212> TYPE: DNA
<213> ORGANISM: Human Papillomavirus

<400> SEQUENCE: 504
ggccccggta cctgt                                              15

<210> SEQ ID NO 505
<211> LENGTH: 19
<212> TYPE: DNA
<213> ORGANISM: Human Papillomavirus

<400> SEQUENCE: 505
ggcaccacct ggtggttta                                         19

<210> SEQ ID NO 506
<211> LENGTH: 20
<212> TYPE: DNA
<213> ORGANISM: Human Papillomavirus

<400> SEQUENCE: 506
ggcaccacct ggtggttaat                                        20

<210> SEQ ID NO 507
<211> LENGTH: 16
<212> TYPE: DNA
<213> ORGANISM: Human Papillomavirus

<400> SEQUENCE: 507
ggcaccacct ggtggc                                            16

<210> SEQ ID NO 508
<211> LENGTH: 23
<212> TYPE: DNA
<213> ORGANISM: Human Papillomavirus

<400> SEQUENCE: 508
ggatatggca atactgaagt gga                                    23

<210> SEQ ID NO 509
<211> LENGTH: 23
<212> TYPE: DNA
<213> ORGANISM: Human Papillomavirus

<400> SEQUENCE: 509
ggatatggca atactgaagt gga                                    23

<210> SEQ ID NO 510
<211> LENGTH: 24
<212> TYPE: DNA
<213> ORGANISM: Human Papillomavirus

<400> SEQUENCE: 510
ggagacatta caaatcaaac cacg                                   24

<210> SEQ ID NO 511
<211> LENGTH: 23
<212> TYPE: DNA
<213> ORGANISM: Human Papillomavirus

<400> SEQUENCE: 511
ggaccatgcg ggcatatact att                                   23

<210> SEQ ID NO 512

-continued

<211> LENGTH: 24
<212> TYPE: DNA
<213> ORGANISM: Human Papillomavirus

<400> SEQUENCE: 512
ggacacgaag ccagaaaata tggg                                                24

<210> SEQ ID NO 513
<211> LENGTH: 27
<212> TYPE: DNA
<213> ORGANISM: Human Papillomavirus

<400> SEQUENCE: 513
ggaaatgttt ttttgaaagg acatggt                                             27

<210> SEQ ID NO 514
<211> LENGTH: 21
<212> TYPE: DNA
<213> ORGANISM: Human Papillomavirus

<400> SEQUENCE: 514
gcttacacag tagagagcgt g                                                   21

<210> SEQ ID NO 515
<211> LENGTH: 15
<212> TYPE: DNA
<213> ORGANISM: Human Papillomavirus

<400> SEQUENCE: 515
gcgtggaggt ggtgg                                                          15

<210> SEQ ID NO 516
<211> LENGTH: 16
<212> TYPE: DNA
<213> ORGANISM: Human Papillomavirus

<400> SEQUENCE: 516
gccgcctgtc aagcga                                                         16

<210> SEQ ID NO 517
<211> LENGTH: 17
<212> TYPE: DNA
<213> ORGANISM: Human Papillomavirus

<400> SEQUENCE: 517
gcccagcaac cagttcc                                                        17

<210> SEQ ID NO 518
<211> LENGTH: 22
<212> TYPE: DNA
<213> ORGANISM: Human Papillomavirus

<400> SEQUENCE: 518
gccatccagt gatgaggatg ag                                                  22

<210> SEQ ID NO 519
<211> LENGTH: 22
<212> TYPE: DNA
<213> ORGANISM: Human Papillomavirus

<400> SEQUENCE: 519
gcagactcag gtaaccctag at                                                  22

-continued

```
<210> SEQ ID NO 520
<211> LENGTH: 20
<212> TYPE: DNA
<213> ORGANISM: Human Papillomavirus

<400> SEQUENCE: 520
gcagacacag gtagaacacg                                                    20

<210> SEQ ID NO 521
<211> LENGTH: 19
<212> TYPE: DNA
<213> ORGANISM: Human Papillomavirus

<400> SEQUENCE: 521
gcaccacctg gtggtcaat                                                     19

<210> SEQ ID NO 522
<211> LENGTH: 19
<212> TYPE: DNA
<213> ORGANISM: Human Papillomavirus

<400> SEQUENCE: 522
gcacagtagg tgcaggctc                                                     19

<210> SEQ ID NO 523
<211> LENGTH: 18
<212> TYPE: DNA
<213> ORGANISM: Human Papillomavirus

<400> SEQUENCE: 523
gcacacaaag aggctgca                                                      18

<210> SEQ ID NO 524
<211> LENGTH: 19
<212> TYPE: DNA
<213> ORGANISM: Human Papillomavirus

<400> SEQUENCE: 524
gaggtggaat atggcggac                                                     19

<210> SEQ ID NO 525
<211> LENGTH: 24
<212> TYPE: DNA
<213> ORGANISM: Human Papillomavirus

<400> SEQUENCE: 525
gagacagtgg atatggctat tctg                                               24

<210> SEQ ID NO 526
<211> LENGTH: 22
<212> TYPE: DNA
<213> ORGANISM: Human Papillomavirus

<400> SEQUENCE: 526
gacagtggct atggctattc tg                                                 22

<210> SEQ ID NO 527
<211> LENGTH: 20
<212> TYPE: DNA
<213> ORGANISM: Human Papillomavirus

<400> SEQUENCE: 527
gacagcggct atggcaatac                                                    20
```

-continued

```
<210> SEQ ID NO 528
<211> LENGTH: 22
<212> TYPE: DNA
<213> ORGANISM: Human Papillomavirus

<400> SEQUENCE: 528
gacagcggat atggcaatac tg                                          22

<210> SEQ ID NO 529
<211> LENGTH: 18
<212> TYPE: DNA
<213> ORGANISM: Human Papillomavirus

<400> SEQUENCE: 529
gacaccacca gacagtcc                                               18

<210> SEQ ID NO 530
<211> LENGTH: 26
<212> TYPE: DNA
<213> ORGANISM: Human Papillomavirus

<400> SEQUENCE: 530
gaaatccttt ttctcaagga cgtggt                                      26

<210> SEQ ID NO 531
<211> LENGTH: 24
<212> TYPE: DNA
<213> ORGANISM: Human Papillomavirus

<400> SEQUENCE: 531
ctgttcgtcc tctgtacttt gcac                                        24

<210> SEQ ID NO 532
<211> LENGTH: 20
<212> TYPE: DNA
<213> ORGANISM: Human Papillomavirus

<400> SEQUENCE: 532
ctccgtctag ccttttcctg                                             20

<210> SEQ ID NO 533
<211> LENGTH: 22
<212> TYPE: DNA
<213> ORGANISM: Human Papillomavirus

<400> SEQUENCE: 533
ctcactattt aaaccgtcgc ca                                          22

<210> SEQ ID NO 534
<211> LENGTH: 19
<212> TYPE: DNA
<213> ORGANISM: Human Papillomavirus

<400> SEQUENCE: 534
ctatttgttt cccctggcg                                              19

<210> SEQ ID NO 535
<211> LENGTH: 24
<212> TYPE: DNA
<213> ORGANISM: Human Papillomavirus

<400> SEQUENCE: 535
ctatgtcttg gctactgttt gttg                                        24
```

-continued

```
<210> SEQ ID NO 536
<211> LENGTH: 20
<212> TYPE: DNA
<213> ORGANISM: Human Papillomavirus

<400> SEQUENCE: 536
ctatggccat acgcaagtgg                                                      20

<210> SEQ ID NO 537
<211> LENGTH: 20
<212> TYPE: DNA
<213> ORGANISM: Human Papillomavirus
<220> FEATURE:
<221> NAME/KEY: 537
<222> LOCATION: (2)..(11)
<223> OTHER INFORMATION: 2,11: n is one of the following nucleotides: a
      or g or c or t
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 537
cngacagcgg ntatggcaat                                                      20

<210> SEQ ID NO 538
<211> LENGTH: 17
<212> TYPE: DNA
<213> ORGANISM: Human Papillomavirus

<400> SEQUENCE: 538
cgtcccctgc atgcctg                                                         17

<210> SEQ ID NO 539
<211> LENGTH: 21
<212> TYPE: DNA
<213> ORGANISM: Human Papillomavirus

<400> SEQUENCE: 539
cgtattgcca tacccactgt c                                                    21

<210> SEQ ID NO 540
<211> LENGTH: 21
<212> TYPE: DNA
<213> ORGANISM: Human Papillomavirus

<400> SEQUENCE: 540
cgtattgcca tacccactgt c                                                    21

<210> SEQ ID NO 541
<211> LENGTH: 21
<212> TYPE: DNA
<213> ORGANISM: Human Papillomavirus

<400> SEQUENCE: 541
cgtattgcca tacccactgt c                                                    21

<210> SEQ ID NO 542
<211> LENGTH: 21
<212> TYPE: DNA
<213> ORGANISM: Human Papillomavirus
```

-continued

<400> SEQUENCE: 542
cgtattgcca tacccactgt c                                            21

<210> SEQ ID NO 543
<211> LENGTH: 21
<212> TYPE: DNA
<213> ORGANISM: Human Papillomavirus

<400> SEQUENCE: 543
cgtattgcca tacccactgt c                                            21

<210> SEQ ID NO 544
<211> LENGTH: 20
<212> TYPE: DNA
<213> ORGANISM: Human Papillomavirus

<400> SEQUENCE: 544
cggttggatg ccataaacct                                             20

<210> SEQ ID NO 545
<211> LENGTH: 19
<212> TYPE: DNA
<213> ORGANISM: Human Papillomavirus

<400> SEQUENCE: 545
cggttgaacg caataagcc                                              19

<210> SEQ ID NO 546
<211> LENGTH: 17
<212> TYPE: DNA
<213> ORGANISM: Human Papillomavirus

<400> SEQUENCE: 546
cggtccgcca tgttctg                                                17

<210> SEQ ID NO 547
<211> LENGTH: 21
<212> TYPE: DNA
<213> ORGANISM: Human Papillomavirus

<400> SEQUENCE: 547
cggggggatg tttacaaagt a                                           21

<210> SEQ ID NO 548
<211> LENGTH: 23
<212> TYPE: DNA
<213> ORGANISM: Human Papillomavirus

<400> SEQUENCE: 548
cgggctgttc tgactaccta gta                                         23

<210> SEQ ID NO 549
<211> LENGTH: 18
<212> TYPE: DNA
<213> ORGANISM: Human Papillomavirus

<400> SEQUENCE: 549
cgacggctgt ttgacaga                                               18

<210> SEQ ID NO 550
<211> LENGTH: 25
<212> TYPE: DNA

-continued

<213> ORGANISM: Human Papillomavirus

<400> SEQUENCE: 550 cctttttttct tccagcatcc ctttg                                    25

<210> SEQ ID NO 551
<211> LENGTH: 25
<212> TYPE: DNA
<213> ORGANISM: Human Papillomavirus

<400> SEQUENCE: 551 cctttttttct tccagcatcc ctttg                                    25

<210> SEQ ID NO 552
<211> LENGTH: 17
<212> TYPE: DNA
<213> ORGANISM: Human Papillomavirus

<400> SEQUENCE: 552
cctttggccc agtgctc                                              17

<210> SEQ ID NO 553
<211> LENGTH: 21
<212> TYPE: DNA
<213> ORGANISM: Human Papillomavirus

<400> SEQUENCE: 553
ccttcttcat tttcctgcac c                                         21

<210> SEQ ID NO 554
<211> LENGTH: 25
<212> TYPE: DNA
<213> ORGANISM: Human Papillomavirus

<400> SEQUENCE: 554
ccttagtaga attctgtagg gacac                                     25

<210> SEQ ID NO 555
<211> LENGTH: 23
<212> TYPE: DNA
<213> ORGANISM: Human Papillomavirus

<400> SEQUENCE: 555
ccgttttcct ctaataaaaa tcc                                       23

<210> SEQ ID NO 556
<211> LENGTH: 23
<212> TYPE: DNA
<213> ORGANISM: Human Papillomavirus

<400> SEQUENCE: 556
ccgctgttta ctgagccttc tat                                       23

<210> SEQ ID NO 557
<211> LENGTH: 18
<212> TYPE: DNA
<213> ORGANISM: Human Papillomavirus

<400> SEQUENCE: 557
ccgccaaatg gccatact                                            18

<210> SEQ ID NO 558
<211> LENGTH: 19

-continued

<212> TYPE: DNA
<213> ORGANISM: Human Papillomavirus

<400> SEQUENCE: 558
ccccggtacc tgactttct                                                            19

<210> SEQ ID NO 559
<211> LENGTH: 19
<212> TYPE: DNA
<213> ORGANISM: Human Papillomavirus

<400> SEQUENCE: 559
ccccacaatc ttccggttc                                                            19

<210> SEQ ID NO 560
<211> LENGTH: 22
<212> TYPE: DNA
<213> ORGANISM: Human Papillomavirus

<400> SEQUENCE: 560
cccacgctta ggtttatatt cc                                                        22

<210> SEQ ID NO 561
<211> LENGTH: 20
<212> TYPE: DNA
<213> ORGANISM: Human Papillomavirus

<400> SEQUENCE: 561
ccatggacac tgcaggacac                                                           20

<210> SEQ ID NO 562
<211> LENGTH: 22
<212> TYPE: DNA
<213> ORGANISM: Human Papillomavirus

<400> SEQUENCE: 562
ccagtccttt cctactgttt ct                                                        22

<210> SEQ ID NO 563
<211> LENGTH: 24
<212> TYPE: DNA
<213> ORGANISM: Human Papillomavirus

<400> SEQUENCE: 563
ccaggcaaag gggtactact aaag                                                      24

<210> SEQ ID NO 564
<211> LENGTH: 18
<212> TYPE: DNA
<213> ORGANISM: Human Papillomavirus

<400> SEQUENCE: 564
ccagcgtgtg gagcaaag                                                             18

<210> SEQ ID NO 565
<211> LENGTH: 20
<212> TYPE: DNA
<213> ORGANISM: Human Papillomavirus

<400> SEQUENCE: 565
ccacttgcgt atggccatag                                                           20

<210> SEQ ID NO 566

-continued

```
<211> LENGTH: 22
<212> TYPE: DNA
<213> ORGANISM: Human Papillomavirus

<400> SEQUENCE: 566
ccactgaaac attgtcccta ct                                          22

<210> SEQ ID NO 567
<211> LENGTH: 21
<212> TYPE: DNA
<213> ORGANISM: Human Papillomavirus

<400> SEQUENCE: 567
ccacctccat gtctgataca g                                           21

<210> SEQ ID NO 568
<211> LENGTH: 18
<212> TYPE: DNA
<213> ORGANISM: Human Papillomavirus

<400> SEQUENCE: 568
ccaaccgccg ccaaatgg                                               18

<210> SEQ ID NO 569
<211> LENGTH: 23
<212> TYPE: DNA
<213> ORGANISM: Human Papillomavirus

<400> SEQUENCE: 569
catattccac ctctacctgt gtc                                         23

<210> SEQ ID NO 570
<211> LENGTH: 20
<212> TYPE: DNA
<213> ORGANISM: Human Papillomavirus

<400> SEQUENCE: 570
caggacaggg ctaggagaag                                             20

<210> SEQ ID NO 571
<211> LENGTH: 20
<212> TYPE: DNA
<213> ORGANISM: Human Papillomavirus

<400> SEQUENCE: 571
caggaaaagg ctagacggag                                             20

<210> SEQ ID NO 572
<211> LENGTH: 27
<212> TYPE: DNA
<213> ORGANISM: Human Papillomavirus

<400> SEQUENCE: 572
cagacgttgc aaaaactaaa acgaaag                                     27

<210> SEQ ID NO 573
<211> LENGTH: 15
<212> TYPE: DNA
<213> ORGANISM: Human Papillomavirus

<400> SEQUENCE: 573
cacggacatg gcgcc                                                  15
```

-continued

```
<210> SEQ ID NO 574
<211> LENGTH: 18
<212> TYPE: DNA
<213> ORGANISM: Human Papillomavirus

<400> SEQUENCE: 574
cacgaaaggg ccagaagg                                            18

<210> SEQ ID NO 575
<211> LENGTH: 23
<212> TYPE: DNA
<213> ORGANISM: Human Papillomavirus

<400> SEQUENCE: 575
caatggcaat actgaagtgg aag                                      23

<210> SEQ ID NO 576
<211> LENGTH: 21
<212> TYPE: DNA
<213> ORGANISM: Human Papillomavirus

<400> SEQUENCE: 576
caatacacca atcgcaacac g                                        21

<210> SEQ ID NO 577
<211> LENGTH: 25
<212> TYPE: DNA
<213> ORGANISM: Human Papillomavirus

<400> SEQUENCE: 577
attatcaaat gttattaggc gctgg                                    25

<210> SEQ ID NO 578
<211> LENGTH: 22
<212> TYPE: DNA
<213> ORGANISM: Human Papillomavirus

<400> SEQUENCE: 578
atctagggtt acctgagtct gc                                       22

<210> SEQ ID NO 579
<211> LENGTH: 24
<212> TYPE: DNA
<213> ORGANISM: Human Papillomavirus

<400> SEQUENCE: 579
atacaatacc acaccacata caac                                     24

<210> SEQ ID NO 580
<211> LENGTH: 21
<212> TYPE: DNA
<213> ORGANISM: Human Papillomavirus

<400> SEQUENCE: 580
agcacctaag aaaaaacgtg c                                        21

<210> SEQ ID NO 581
<211> LENGTH: 18
<212> TYPE: DNA
<213> ORGANISM: Human Papillomavirus

<400> SEQUENCE: 581
actgtctgca cctggtct                                            18
```

-continued

<210> SEQ ID NO 582
<211> LENGTH: 19
<212> TYPE: DNA
<213> ORGANISM: Human Papillomavirus

<400> SEQUENCE: 582
actgctgtgt ccgtaggca                                                          19

<210> SEQ ID NO 583
<211> LENGTH: 18
<212> TYPE: DNA
<213> ORGANISM: Human Papillomavirus

<400> SEQUENCE: 583
acgaaaaagc caggcgac                                                           18

<210> SEQ ID NO 584
<211> LENGTH: 18
<212> TYPE: DNA
<213> ORGANISM: Human Papillomavirus

<400> SEQUENCE: 584 acccccacg gtatcttc                                                            18

<210> SEQ ID NO 585
<211> LENGTH: 22
<212> TYPE: DNA
<213> ORGANISM: Human Papillomavirus

<400> SEQUENCE: 585
accatgtaca aatcacatgc ac                                                      22

<210> SEQ ID NO 586
<211> LENGTH: 19
<212> TYPE: DNA
<213> ORGANISM: Human Papillomavirus

<400> SEQUENCE: 586
acaaccttct cctggcctt                                                          19

<210> SEQ ID NO 587
<211> LENGTH: 26
<212> TYPE: DNA
<213> ORGANISM: Human Papillomavirus

<400> SEQUENCE: 587
aatgcatcat aaatcaccct tgaacc                                                  26

<210> SEQ ID NO 588
<211> LENGTH: 19
<212> TYPE: DNA
<213> ORGANISM: Human Papillomavirus

<400> SEQUENCE: 588
aaggccagga gaaggttgt                                                          19

<210> SEQ ID NO 589
<211> LENGTH: 22
<212> TYPE: DNA
<213> ORGANISM: Human Papillomavirus

<400> SEQUENCE: 589
aactagtaat gcaaaggcag ca                                                      22

```
<210> SEQ ID NO 590
<211> LENGTH: 22
<212> TYPE: DNA
<213> ORGANISM: Human Papillomavirus

<400> SEQUENCE: 590
aaagtgtagg gtaacatctg gg                                                   22

<210> SEQ ID NO 591
<211> LENGTH: 20
<212> TYPE: DNA
<213> ORGANISM: Human Papillomavirus

<400> SEQUENCE: 591
gacagcggct atggcaatag                                                      20

<210> SEQ ID NO 592
<211> LENGTH: 20
<212> TYPE: DNA
<213> ORGANISM: Human Papillomavirus

<400> SEQUENCE: 592
ctcgttcact atgtgtcccg                                                      20

<210> SEQ ID NO 593
<211> LENGTH: 25
<212> TYPE: DNA
<213> ORGANISM: Human Papillomavirus

<400> SEQUENCE: 593
cctgtaactg tggaaagtat accat                                                25

<210> SEQ ID NO 594
<211> LENGTH: 26
<212> TYPE: DNA
<213> ORGANISM: Human Papillomavirus

<400> SEQUENCE: 594
acaacttaca tctgaattac tagccc                                               26

<210> SEQ ID NO 595
<211> LENGTH: 24
<212> TYPE: DNA
<213> ORGANISM: Human Papillomavirus

<400> SEQUENCE: 595
aacagtagag atcagttgtc tctg                                                 24

<210> SEQ ID NO 596
<211> LENGTH: 20
<212> TYPE: DNA
<213> ORGANISM: Human Papillomavirus

<400> SEQUENCE: 596
aacacgtaga gaaacccagc                                                      20

<210> SEQ ID NO 597
<211> LENGTH: 22
<212> TYPE: DNA
<213> ORGANISM: Human Papillomavirus

<400> SEQUENCE: 597
```

-continued

```
ctgcttacat ctgaactagc cc                                    22

<210> SEQ ID NO 598
<211> LENGTH: 21
<212> TYPE: DNA
<213> ORGANISM: Human Papillomavirus

<400> SEQUENCE: 598
acagcggata tggcaatact g                                     21

<210> SEQ ID NO 599
<211> LENGTH: 21
<212> TYPE: DNA
<213> ORGANISM: Human Papillomavirus

<400> SEQUENCE: 599
acagcggata tggcaataca c                                     21

<210> SEQ ID NO 600
<211> LENGTH: 19
<212> TYPE: DNA
<213> ORGANISM: Human Papillomavirus

<400> SEQUENCE: 600
taggcaggaa taccagggg                                        19

<210> SEQ ID NO 601
<211> LENGTH: 21
<212> TYPE: DNA
<213> ORGANISM: Human Papillomavirus

<400> SEQUENCE: 601
gctacagtta cctcctccac t                                     21

<210> SEQ ID NO 602
<211> LENGTH: 20
<212> TYPE: DNA
<213> ORGANISM: Human Papillomavirus

<400> SEQUENCE: 602
caacaacaca ctaccgcctt                                       20

<210> SEQ ID NO 603
<211> LENGTH: 21
<212> TYPE: DNA
<213> ORGANISM: Human Papillomavirus

<400> SEQUENCE: 603
aaaacctgtt gtaggtggga c                                     21

<210> SEQ ID NO 604
<211> LENGTH: 22
<212> TYPE: DNA
<213> ORGANISM: Human Papillomavirus

<400> SEQUENCE: 604
cacagctttc tgttgtttcc ac                                    22

<210> SEQ ID NO 605
<211> LENGTH: 21
<212> TYPE: DNA
<213> ORGANISM: Human Papillomavirus

<400> SEQUENCE: 605
```

-continued

```
cacggtatcc gctactcagc t                                        21

<210> SEQ ID NO 606
<211> LENGTH: 21
<212> TYPE: DNA
<213> ORGANISM: Human Papillomavirus

<400> SEQUENCE: 606
gcatcttctg ggtcaggtac g                                        21

<210> SEQ ID NO 607
<211> LENGTH: 22
<212> TYPE: DNA
<213> ORGANISM: Human Papillomavirus

<400> SEQUENCE: 607
ctcttgtttc ttcccaggct gc                                       22

<210> SEQ ID NO 608
<211> LENGTH: 20
<212> TYPE: DNA
<213> ORGANISM: Human Papillomavirus

<400> SEQUENCE: 608
actgtgaggt ggacacacgg                                          20

<210> SEQ ID NO 609
<211> LENGTH: 20
<212> TYPE: DNA
<213> ORGANISM: Human Papillomavirus

<400> SEQUENCE: 609
tcaaaggttg tggcaacgga                                          20

<210> SEQ ID NO 610
<211> LENGTH: 26
<212> TYPE: DNA
<213> ORGANISM: Human Papillomavirus

<400> SEQUENCE: 610
ggcagtacta gtaggtgctt catctg                                   26

<210> SEQ ID NO 611
<211> LENGTH: 21
<212> TYPE: DNA
<213> ORGANISM: Human Papillomavirus

<400> SEQUENCE: 611
gcctgtaggt gtagctgcac c                                        21

<210> SEQ ID NO 612
<211> LENGTH: 24
<212> TYPE: DNA
<213> ORGANISM: Human Papillomavirus

<400> SEQUENCE: 612
catacagaca gacaacgata accg                                     24

<210> SEQ ID NO 613
<211> LENGTH: 20
<212> TYPE: DNA
<213> ORGANISM: Human Papillomavirus
```

-continued

```
<400> SEQUENCE: 613
agcaacctag agctacctgc                                          20

<210> SEQ ID NO 614
<211> LENGTH: 20
<212> TYPE: DNA
<213> ORGANISM: Human Papillomavirus

<400> SEQUENCE: 614
gacagcgggt atggcaatac                                          20

<210> SEQ ID NO 615
<211> LENGTH: 21
<212> TYPE: DNA
<213> ORGANISM: Human Papillomavirus

<400> SEQUENCE: 615
cgtgctgttc tattgtccaa g                                        21

<210> SEQ ID NO 616
<211> LENGTH: 20
<212> TYPE: DNA
<213> ORGANISM: Human Papillomavirus

<400> SEQUENCE: 616
actaggtcaa agcctgctgt                                          20

<210> SEQ ID NO 617
<211> LENGTH: 15
<212> TYPE: DNA
<213> ORGANISM: Homo Sapiens

<400> SEQUENCE: 617
ttggattaaa acctt                                               15

<210> SEQ ID NO 618
<211> LENGTH: 15
<212> TYPE: DNA
<213> ORGANISM: Homo Sapiens

<400> SEQUENCE: 618
atatatattt ttttt                                               15

<210> SEQ ID NO 619
<211> LENGTH: 23
<212> TYPE: DNA
<213> ORGANISM: Homo Sapiens

<400> SEQUENCE: 619
ttcctttcag ctctaacact ctg                                      23

<210> SEQ ID NO 620
<211> LENGTH: 24
<212> TYPE: DNA
<213> ORGANISM: Homo Sapiens

<400> SEQUENCE: 620
tggatcctga gaacttcagg gtga                                     24

<210> SEQ ID NO 621
<211> LENGTH: 24
<212> TYPE: DNA
<213> ORGANISM: Homo Sapiens
```

-continued

<400> SEQUENCE: 621
ggggaaagaa aacatcaagc gtcc                                                  24

<210> SEQ ID NO 622
<211> LENGTH: 21
<212> TYPE: DNA
<213> ORGANISM: Homo Sapiens

<400> SEQUENCE: 622
gctgcacgtg gatcctgaga a                                                     21

<210> SEQ ID NO 623
<211> LENGTH: 22
<212> TYPE: DNA
<213> ORGANISM: Homo Sapiens

<400> SEQUENCE: 623
gcgtcccata gactcaccct ga                                                    22

<210> SEQ ID NO 624
<211> LENGTH: 29
<212> TYPE: DNA
<213> ORGANISM: Homo Sapiens

<400> SEQUENCE: 624
gataactaga aatagaggat ccagtttct                                             29

<210> SEQ ID NO 625
<211> LENGTH: 23
<212> TYPE: DNA
<213> ORGANISM: Homo Sapiens

<400> SEQUENCE: 625
ctgcacgtgg atcctgagaa ctt                                                   23

<210> SEQ ID NO 626
<211> LENGTH: 24
<212> TYPE: DNA
<213> ORGANISM: Homo Sapiens

<400> SEQUENCE: 626
catcaagcgt cccatagact cacc                                                  24

<210> SEQ ID NO 627
<211> LENGTH: 24
<212> TYPE: DNA
<213> ORGANISM: Homo Sapiens

<400> SEQUENCE: 627
acactctgaa actacgatta caca                                                  24

<210> SEQ ID NO 628
<211> LENGTH: 20
<212> TYPE: DNA
<213> ORGANISM: Homo Sapiens

<400> SEQUENCE: 628
gaagagccaa ggacaggtac                                                       20

<210> SEQ ID NO 629
<211> LENGTH: 20
<212> TYPE: DNA

```
<213> ORGANISM: Homo Sapiens

<400> SEQUENCE: 629
caacttcatc cacgttcacc                                              20

<210> SEQ ID NO 630
<211> LENGTH: 20
<212> TYPE: DNA
<213> ORGANISM: Homo Sapiens

<400> SEQUENCE: 630
ctgggactca atggcgctaa                                              20

<210> SEQ ID NO 631
<211> LENGTH: 18
<212> TYPE: DNA
<213> ORGANISM: Homo Sapiens

<400> SEQUENCE: 631
cggttcaaac agcgaccg                                                18

<210> SEQ ID NO 632
<211> LENGTH: 20
<212> TYPE: DNA
<213> ORGANISM: Homo Sapiens

<400> SEQUENCE: 632
ggactcaatg gcgctaatcg                                              20

<210> SEQ ID NO 633
<211> LENGTH: 19
<212> TYPE: DNA
<213> ORGANISM: Homo Sapiens

<400> SEQUENCE: 633
ggttcaaaca gcgaccggg                                               19

<210> SEQ ID NO 634
<211> LENGTH: 19
<212> TYPE: DNA
<213> ORGANISM: Homo Sapiens

<400> SEQUENCE: 634
ggtcctttgg gcgctaact                                               19

<210> SEQ ID NO 635
<211> LENGTH: 19
<212> TYPE: DNA
<213> ORGANISM: Homo Sapiens

<400> SEQUENCE: 635
cccggttcaa acagcgacc                                               19

<210> SEQ ID NO 636
<211> LENGTH: 23
<212> TYPE: DNA
<213> ORGANISM: Neisseria gonorrhoeae

<400> SEQUENCE: 636
ttcaatggat cggtatcact cgc                                          23

<210> SEQ ID NO 637
<211> LENGTH: 24
```

-continued

```
<212> TYPE: DNA
<213> ORGANISM: Neisseria gonorrhoeae

<400> SEQUENCE: 637
gtcaaactca aacgcccgat aaac                                        24

<210> SEQ ID NO 638
<211> LENGTH: 23
<212> TYPE: DNA
<213> ORGANISM: Neisseria gonorrhoeae

<400> SEQUENCE: 638
gaaacacctt cacgacttac cgg                                         23

<210> SEQ ID NO 639
<211> LENGTH: 22
<212> TYPE: DNA
<213> ORGANISM: Neisseria gonorrhoeae

<400> SEQUENCE: 639
ctccgccgtg ttctttaatc ca                                          22

<210> SEQ ID NO 640
<211> LENGTH: 23
<212> TYPE: DNA
<213> ORGANISM: Neisseria gonorrhoeae

<400> SEQUENCE: 640
ccaactcgaa cagtagggac atg                                         23

<210> SEQ ID NO 641
<211> LENGTH: 22
<212> TYPE: DNA
<213> ORGANISM: Neisseria gonorrhoeae

<400> SEQUENCE: 641
cagcggcagc attcaatttg tt                                          22

<210> SEQ ID NO 642
<211> LENGTH: 17
<212> TYPE: DNA
<213> ORGANISM: Treponema pallidum

<400> SEQUENCE: 642
tcgcggcgct tgtatcg                                                17

<210> SEQ ID NO 643
<211> LENGTH: 18
<212> TYPE: DNA
<213> ORGANISM: Treponema pallidum

<400> SEQUENCE: 643
tcctccacct cacgctcc                                               18

<210> SEQ ID NO 644
<211> LENGTH: 16
<212> TYPE: DNA
<213> ORGANISM: Treponema pallidum

<400> SEQUENCE: 644
tacgtggagc cggcct                                                 16

<210> SEQ ID NO 645
```

-continued

```
<211> LENGTH: 17
<212> TYPE: DNA
<213> ORGANISM: Treponema pallidum

<400> SEQUENCE: 645
ggttgtgccg agcacgg                                                  17

<210> SEQ ID NO 646
<211> LENGTH: 24
<212> TYPE: DNA
<213> ORGANISM: Treponema pallidum

<400> SEQUENCE: 646
gagtcaactc agtgtacatg tgca                                          24

<210> SEQ ID NO 647
<211> LENGTH: 22
<212> TYPE: DNA
<213> ORGANISM: Treponema pallidum

<400> SEQUENCE: 647
cgtctggtcg atgtgcaaat ga                                            22

<210> SEQ ID NO 648
<211> LENGTH: 22
<212> TYPE: DNA
<213> ORGANISM: Treponema pallidum

<400> SEQUENCE: 648
cgtctggtcg atgtgcaaat ga                                            22

<210> SEQ ID NO 649
<211> LENGTH: 21
<212> TYPE: DNA
<213> ORGANISM: Treponema pallidum

<400> SEQUENCE: 649
cgctcaagga aagcgagaag t                                             21

<210> SEQ ID NO 650
<211> LENGTH: 18
<212> TYPE: DNA
<213> ORGANISM: Treponema pallidum

<400> SEQUENCE: 650
cgcgtgtgcg aatggtgt                                                 18

<210> SEQ ID NO 651
<211> LENGTH: 18
<212> TYPE: DNA
<213> ORGANISM: Treponema pallidum

<400> SEQUENCE: 651
cctcacgctc ccctcctt                                                 18

<210> SEQ ID NO 652
<211> LENGTH: 24
<212> TYPE: DNA
<213> ORGANISM: Treponema pallidum

<400> SEQUENCE: 652
ccgagtcaac tcagtgtaca tgtg                                          24
```

```
<210> SEQ ID NO 653
<211> LENGTH: 21
<212> TYPE: DNA
<213> ORGANISM: Treponema pallidum

<400> SEQUENCE: 653
caggcgtttt tgagcactgt g                                                   21

<210> SEQ ID NO 654
<211> LENGTH: 19
<212> TYPE: DNA
<213> ORGANISM: Treponema pallidum

<400> SEQUENCE: 654
actgaatgga gctgtgccc                                                      19

<210> SEQ ID NO 655
<211> LENGTH: 100
<212> TYPE: DNA
<213> ORGANISM: Human Papillomavirus

<400> SEQUENCE: 655
aacacgtaga gaaacccagc tgtaatcatg catggagata cacctacatt gcatgaatat        60
atgttagatt tgcaaccaga gacaactgat ctctactgtt                              100

<210> SEQ ID NO 656
<211> LENGTH: 100
<212> TYPE: DNA
<213> ORGANISM: Human Papillomavirus

<400> SEQUENCE: 656
aacagtagag atcagttgtc tctggttgca aatctaacat atattcatgc aatgtaggtg        60
tatctccatg catgattaca gctgggtttc tctacgtgtt                              100

<210> SEQ ID NO 657
<211> LENGTH: 193
<212> TYPE: DNA
<213> ORGANISM: Human Papillomavirus

<400> SEQUENCE: 657
cacggtatcc gctactcagc ttgttaaaca gctacagcac acccctcac cgtattccag         60 caccgtgtcc gtgggcaccg caaagaccta cggccgacg tcggctgcta cacgacctgg         120
acactgtgga ctcgcggaga agcagcattg tggacctgtc aacccacttc tcggtgcagc        180
tacacctaca ggc                                                           193

<210> SEQ ID NO 658
<211> LENGTH: 193
<212> TYPE: DNA
<213> ORGANISM: Human Papillomavirus

<400> SEQUENCE: 658
gcctgtaggt gtagctgcac cgagaagtgg gttgacaggt ccacaatgct gcttctccgc        60
gagtccacag tgtccaggtc gtgtagcagc cgacgtctgg ccgtaggtct ttgcggtgcc        120
cacggacacg gtgctggaat acggtgaggg ggtgtgctgt agctgtttaa caagctgagt        180
agcggatacc gtg                                                           193

<210> SEQ ID NO 659
<211> LENGTH: 109
<212> TYPE: DNA
```

<213> ORGANISM: Human Papillomavirus

<400> SEQUENCE: 659
gacagcgggt atggcaatac tgaagtggaa acgcagcaga tggtacaggt agaggagcaa        60
caaacaacat taagttgtaa tggtagtgac gggacacata gtgaacgag                    109

<210> SEQ ID NO 660
<211> LENGTH: 109
<212> TYPE: DNA
<213> ORGANISM: Human Papillomavirus

<400> SEQUENCE: 660
ctcgttcact atgtgtcccg tcactaccat tacaacttaa tgttgtttgt tgctcctcta        60
cctgtaccat ctgctgcgtt tccacttcag tattgccata cccgctgtc                    109

<210> SEQ ID NO 661
<211> LENGTH: 135
<212> TYPE: DNA
<213> ORGANISM: Human Papillomavirus

<400> SEQUENCE: 661
catacagaca gacaacgata accgaccacc acaagcagcg gccaaacgac gacgacctgc        60
agacaccaca gacaccgccc agccccttac aaagctgttc tgtgcagacc ccgccttgga        120
caatagaaca gcacg                                                         135

<210> SEQ ID NO 662
<211> LENGTH: 135
<212> TYPE: DNA
<213> ORGANISM: Human Papillomavirus

<400> SEQUENCE: 662
cgtgctgttc tattgtccaa ggcggggtct gcacagaaca gctttgtaag gggctgggcg        60
gtgtctgtgg tgtctgcagg tcgtcgtcgt ttggccgctg cttgtggtgg tcggttatcg        120
ttgtctgtct gtatg                                                         135

<210> SEQ ID NO 663
<211> LENGTH: 138
<212> TYPE: DNA
<213> ORGANISM: Human Papillomavirus

<400> SEQUENCE: 663
cctgtaactg tggaaagtat accattagac acaattggcc ctttagattc ttctatagtg        60
tcattagtag aggaaactag ttttattgag tctggtgccc ctgttgttac accaagggtc        120
ccacctacaa caggtttt                                                      138

<210> SEQ ID NO 664
<211> LENGTH: 138
<212> TYPE: DNA
<213> ORGANISM: Human Papillomavirus

<400> SEQUENCE: 664
aaaacctgtt gtaggtggga cccttggtgt aacaacaggg gcaccagact caataaaact        60
agtttcctct actaatgaca ctatagaaga atctaaaggg ccaattgtgt ctaatggtat        120
actttccaca gttacagg                                                      138

<210> SEQ ID NO 665
<211> LENGTH: 145

-continued

```
<212> TYPE: DNA
<213> ORGANISM: Human Papillomavirus

<400> SEQUENCE: 665
taggcaggaa taccagggga acactacagg aaatttcatt aaatgtaagc agtacgcagg      60
caacacaaac ggtgtattcc gtgccagaca gcggatatgg caatatggaa gtggaaacag     120
ctgaagtgga ggaggtaact gtagc                                          145

<210> SEQ ID NO 666
<211> LENGTH: 145
<212> TYPE: DNA
<213> ORGANISM: Human Papillomavirus

<400> SEQUENCE: 666
gctacagtta cctcctccac ttcagctgtt tccacttcca tattgccata tccgctgtct      60
ggcacggaat acaccgtttg tgttgcctgc gtactgctta catttaatga aatttcctgt     120
agtgttcccc tggtattcct gccta                                          145

<210> SEQ ID NO 667
<211> LENGTH: 121
<212> TYPE: DNA
<213> ORGANISM: Human Papillomavirus

<400> SEQUENCE: 667
gcatcttctg ggtcaggtac ggaacccatt agtagtaccc ccctccctac tgtgcggcgg      60
gtacggggtc cccgcctgta tagtagggct aatcaacagg tccgtgtgtc cacctcacag     120
t                                                                    121

<210> SEQ ID NO 668
<211> LENGTH: 121
<212> TYPE: DNA
<213> ORGANISM: Human Papillomavirus

<400> SEQUENCE: 668
actgtgaggt ggacacacgg acctgttgat tagccctact atacaggcgg ggaccccgta      60
cccgccgcac agtagggagg ggggtactac taatgggttc cgtacctgac ccagaagatg     120
c                                                                    121

<210> SEQ ID NO 669
<211> LENGTH: 138
<212> TYPE: DNA
<213> ORGANISM: Human Papillomavirus

<400> SEQUENCE: 669
acagcggata tggcaataca caagtggaaa ctgtggaagc aacgttgcag gtagatgggc      60
aacatggcgg ttcacagaac agtgtgtgta gtagcggggg gggcagtgtt atggatgtgg     120
aaacaacaga aagctgtg                                                  138

<210> SEQ ID NO 670
<211> LENGTH: 138
<212> TYPE: DNA
<213> ORGANISM: Human Papillomavirus

<400> SEQUENCE: 670
cacagctttc tgttgtttcc acatccataa cactgccccc cccgctacta cacacactgt      60
tctgtgaacc gccatgttgc ccatctacct gcaacgttgc ttccacagtt tccacttgtg     120
```

-continued

```
tattgccata tccgctgt                                           138

<210> SEQ ID NO 671
<211> LENGTH: 159
<212> TYPE: DNA
<213> ORGANISM: Human Papillomavirus

<400> SEQUENCE: 671
cccgacctgt gacccaagtg taacgtcatg cgtggagaca aagcaactat aaaagattat    60
atattagatc tgcaacctga aacaactgac ctacactgct atgagcaatt aggtgacagc   120
tcagatgagg aggatacaga tggtgtggac cggccagat                          159

<210> SEQ ID NO 672
<211> LENGTH: 159
<212> TYPE: DNA
<213> ORGANISM: Human Papillomavirus

<400> SEQUENCE: 672
atctggccgg tccacaccat ctgtatcctc ctcatctgag ctgtcaccta attgctcata    60
gcagtgtagg tcagttgttt caggttgcag atctaatata taatctttta tagttgcttt   120
gtctccacgc atgacgttac acttgggtca caggtcggg                          159

<210> SEQ ID NO 673
<211> LENGTH: 99
<212> TYPE: DNA
<213> ORGANISM: Human Papillomavirus

<400> SEQUENCE: 673
cacaacaaca cactaccgcc ttttacgttt tgctggtgta gaggtggagg taggagcaga    60
tcgcttttta gaggtagcta cagcaggctt tgacctagt                           99

<210> SEQ ID NO 674
<211> LENGTH: 99
<212> TYPE: DNA
<213> ORGANISM: Human Papillomavirus

<400> SEQUENCE: 674
actaggtcaa agcctgctgt agctacctct aaaaagcgat ctgctcctac ctccacctct    60
acaccagcaa aacgtaaaag gcggtagtgt gttgttgtg                           99

<210> SEQ ID NO 675
<211> LENGTH: 127
<212> TYPE: DNA
<213> ORGANISM: Human Papillomavirus

<400> SEQUENCE: 675
acagcggata tggcaatact gaagtggaaa ctgagcagat ggcacaccag gtagaaagcc    60
aaaatggcga cgcagactta aatgactcgg agtctagtgg ggtgggggct agttcagatg   120
taagcag                                                             127

<210> SEQ ID NO 676
<211> LENGTH: 127
<212> TYPE: DNA
<213> ORGANISM: Human Papillomavirus

<400> SEQUENCE: 676
ctgcttacat ctgaactagc ccccacccca ctagactccg agtcatttaa gtctgcgtcg    60
ccattttggc tttctacctg gtgtgccatc tgctcagttt ccacttcagt attgccatat   120
```

-continued

```
ccgctgt                                                                     127

<210> SEQ ID NO 677
<211> LENGTH: 83
<212> TYPE: DNA
<213> ORGANISM: Human Papillomavirus

<400> SEQUENCE: 677
ctcttgtttc ttcccaggct gctactgatg atatatatga tatatatgca gatattacag        60
atgaagcacc tactagtact gcc                                                  83

<210> SEQ ID NO 678
<211> LENGTH: 83
<212> TYPE: DNA
<213> ORGANISM: Human Papillomavirus

<400> SEQUENCE: 678
ggcagtacta gtaggtgctt catctgtaat atctgcatat atatcatata tatcatcagt        60
agcagcctgg gaagaaacaa gag                                                  83

<210> SEQ ID NO 679
<211> LENGTH: 74
<212> TYPE: DNA
<213> ORGANISM: Human Papillomavirus

<400> SEQUENCE: 679
tcaaaggttg tggcaacgga tacatatgta aaacgtacca gtatatttta tcatgcaggt        60
agctctaggt tgct                                                            74

<210> SEQ ID NO 680
<211> LENGTH: 74
<212> TYPE: DNA
<213> ORGANISM: Human Papillomavirus

<400> SEQUENCE: 680
agcaacctag agctacctgc atgataaaat atactggtac gttttacata tgtatccgtt        60
gccacaacct ttga                                                            74

<210> SEQ ID NO 681
<211> LENGTH: 19
<212> TYPE: DNA
<213> ORGANISM: Human Papillomavirus

<400> SEQUENCE: 681
ctgggtttct ctacgtgtt                                                       19

<210> SEQ ID NO 682
<211> LENGTH: 23
<212> TYPE: DNA
<213> ORGANISM: Human Papillomavirus

<400> SEQUENCE: 682
agagacaact gatctctact gtt                                                  23

<210> SEQ ID NO 683
<211> LENGTH: 20
<212> TYPE: DNA
<213> ORGANISM: Human Papillomavirus

<400> SEQUENCE: 683
```

-continued

```
gctgagtagc ggataccgtg                                          20

<210> SEQ ID NO 684
<211> LENGTH: 20
<212> TYPE: DNA
<213> ORGANISM: Human Papillomavirus

<400> SEQUENCE: 684
gtgcagctac acctacaggc                                          20

<210> SEQ ID NO 685
<211> LENGTH: 19
<212> TYPE: DNA
<213> ORGANISM: Human Papillomavirus

<400> SEQUENCE: 685
tattgccata cccgctgtc                                           19

<210> SEQ ID NO 686
<211> LENGTH: 19
<212> TYPE: DNA
<213> ORGANISM: Human Papillomavirus

<400> SEQUENCE: 686
gggacacata gtgaacgag                                           19

<210> SEQ ID NO 687
<211> LENGTH: 18
<212> TYPE: DNA
<213> ORGANISM: Human Papillomavirus

<400> SEQUENCE: 687
cttgggtcac aggtcggg                                            18

<210> SEQ ID NO 688
<211> LENGTH: 17
<212> TYPE: DNA
<213> ORGANISM: Human Papillomavirus

<400> SEQUENCE: 688
gtgtggaccg gccagat                                             17

<210> SEQ ID NO 689
<211> LENGTH: 24
<212> TYPE: DNA
<213> ORGANISM: Human Papillomavirus

<400> SEQUENCE: 689
tggtatactt tccacagtta cagg                                     24

<210> SEQ ID NO 690
<211> LENGTH: 20
<212> TYPE: DNA
<213> ORGANISM: Human Papillomavirus

<400> SEQUENCE: 690
tcccacctac aacaggtttt                                          20

<210> SEQ ID NO 691
<211> LENGTH: 20
<212> TYPE: DNA
<213> ORGANISM: Human Papillomavirus

<400> SEQUENCE: 691
```

-continued

```
agtattgcca tatccgctgt                                          20

<210> SEQ ID NO 692
<211> LENGTH: 21
<212> TYPE: DNA
<213> ORGANISM: Human Papillomavirus

<400> SEQUENCE: 692
ggctagttca gatgtaagca g                                        21

<210> SEQ ID NO 693
<211> LENGTH: 23
<212> TYPE: DNA
<213> ORGANISM: Human Papillomavirus

<400> SEQUENCE: 693
ggttatcgtt gtctgtctgt atg                                      23

<210> SEQ ID NO 694
<211> LENGTH: 20
<212> TYPE: DNA
<213> ORGANISM: Human Papillomavirus

<400> SEQUENCE: 694
ttggacaata gaacagcacg                                          20

<210> SEQ ID NO 695
<211> LENGTH: 20
<212> TYPE: DNA
<213> ORGANISM: Human Papillomavirus

<400> SEQUENCE: 695
gtacctgacc cagaagatgc                                          20

<210> SEQ ID NO 696
<211> LENGTH: 19
<212> TYPE: DNA
<213> ORGANISM: Human Papillomavirus

<400> SEQUENCE: 696
cgtgtgtcca cctcacagt                                           19

<210> SEQ ID NO 697
<211> LENGTH: 18
<212> TYPE: DNA
<213> ORGANISM: Human Papillomavirus

<400> SEQUENCE: 697
ccctggtatt cctgccta                                            18

<210> SEQ ID NO 698
<211> LENGTH: 20
<212> TYPE: DNA
<213> ORGANISM: Human Papillomavirus

<400> SEQUENCE: 698
gtggaggagg taactgtagc                                          20

<210> SEQ ID NO 699
<211> LENGTH: 19
<212> TYPE: DNA
<213> ORGANISM: Human Papillomavirus
```

-continued

```
<400> SEQUENCE: 699
ccgttgccac aacctttga                                      19

<210> SEQ ID NO 700
<211> LENGTH: 19
<212> TYPE: DNA
<213> ORGANISM: Human Papillomavirus

<400> SEQUENCE: 700
caggtagctc taggttgct                                      19

<210> SEQ ID NO 701
<211> LENGTH: 20
<212> TYPE: DNA
<213> ORGANISM: Human Papillomavirus

<400> SEQUENCE: 701
tgtattgcca tatccgctgt                                     20

<210> SEQ ID NO 702
<211> LENGTH: 21
<212> TYPE: DNA
<213> ORGANISM: Human Papillomavirus

<400> SEQUENCE: 702
tggaaacaac agaaagctgt g                                   21

<210> SEQ ID NO 703
<211> LENGTH: 21
<212> TYPE: DNA
<213> ORGANISM: Human Papillomavirus

<400> SEQUENCE: 703
aggcggtagt gtgttgttgt g                                   21

<210> SEQ ID NO 704
<211> LENGTH: 22
<212> TYPE: DNA
<213> ORGANISM: Human Papillomavirus

<400> SEQUENCE: 704
ctacagcagg ctttgaccta gt                                  22

<210> SEQ ID NO 705
<211> LENGTH: 21
<212> TYPE: DNA
<213> ORGANISM: Human Papillomavirus

<400> SEQUENCE: 705
cagcctggga agaaacaaga g                                   21

<210> SEQ ID NO 706
<211> LENGTH: 25
<212> TYPE: DNA
<213> ORGANISM: Human Papillomavirus

<400> SEQUENCE: 706
agatgaagca cctactagta ctgcc                               25
```